(12) United States Patent
Hamdy et al.

(10) Patent No.: US 11,771,696 B2
(45) Date of Patent: *Oct. 3, 2023

(54) METHODS OF TREATING CHRONIC LYMPHOCYTIC LEUKEMIA AND SMALL LYMPHOCYTIC LEUKEMIA USING A BTK INHIBITOR

(71) Applicant: Acerta Pharma B.V., Oss (NL)

(72) Inventors: Ahmed Hamdy, Santa Cruz, CA (US); Wayne Rothbaum, New York, NY (US); Raquel Izumi, San Carlos, CA (US); Brian Lannutti, Solana Beach, CA (US); Todd Covey, San Carlos, CA (US); Roger Ulrich, Sammamish, WA (US); Dave Johnson, Aptos, CA (US); Tjeerd Barf, Ravenstein (NL); Allard Kaptein, Zaltbommel (NL)

(73) Assignee: Acerta Pharma B.V., Oss (NL)

( * ) Notice: Subject to any disclaimer, the term of this patent is extended or adjusted under 35 U.S.C. 154(b) by 41 days.

This patent is subject to a terminal disclaimer.

(21) Appl. No.: 17/370,778

(22) Filed: Jul. 8, 2021

(65) Prior Publication Data

US 2021/0401835 A1 Dec. 30, 2021

Related U.S. Application Data

(63) Continuation of application No. 16/298,094, filed on Mar. 11, 2019, now Pat. No. 11,090,302, which is a continuation of application No. 15/112,968, filed as application No. PCT/IB2015/000645 on Jan. 21, 2015, now Pat. No. 10,272,083.

(60) Provisional application No. 62/035,777, filed on Aug. 11, 2014, provisional application No. 61/974,665, filed on Apr. 3, 2014, provisional application No. 61/929,742, filed on Jan. 21, 2014.

(51) Int. Cl.
| | |
|---|---|
| *A61K 31/4985* | (2006.01) |
| *A61K 39/395* | (2006.01) |
| *A61K 45/06* | (2006.01) |
| *C07K 16/28* | (2006.01) |

(52) U.S. Cl.
CPC .... *A61K 31/4985* (2013.01); *A61K 39/39558* (2013.01); *A61K 45/06* (2013.01); *C07K 16/2887* (2013.01); *C07K 2317/24* (2013.01); *C07K 2317/732* (2013.01)

(58) Field of Classification Search
CPC ............. A61K 31/498; A61K 31/4985; A61K 31/499; A61K 31/4995
See application file for complete search history.

(56) References Cited

U.S. PATENT DOCUMENTS

| | | | |
|---|---|---|---|
| 7,459,554 B2 | 12/2008 | Dong et al. | |
| 7,732,454 B2 | 6/2010 | Verner | |
| 7,825,118 B2 | 11/2010 | Honigberg et al. | |
| 7,960,396 B2 | 6/2011 | Honigberg et al. | |
| 8,377,946 B1 | 2/2013 | Chen et al. | |
| 8,658,794 B2 | 2/2014 | deMan et al. | |
| 9,290,504 B2 | 3/2016 | Barf et al. | |
| 9,758,524 B2 | 9/2017 | Barf et al. | |
| 10,272,083 B2 * | 4/2019 | Hamdy ................. A61P 35/00 |
| 11,090,302 B2 * | 8/2021 | Hamdy ............. C07K 16/2809 |
| 2006/0084654 A1 | 4/2006 | Beck et al. | |
| 2008/0076921 A1 | 3/2008 | Honigberg et al. | |
| 2011/0257203 A1 | 10/2011 | Honigberg et al. | |
| 2012/0053189 A1 | 3/2012 | Loury | |
| 2012/0071497 A1 | 3/2012 | Buggy et al. | |
| 2012/0095026 A1 | 4/2012 | Honigberg et al. | |
| 2012/0129821 A1 | 5/2012 | Honigberg et al. | |
| 2012/0135944 A1 | 5/2012 | Honigberg et al. | |
| 2012/0165328 A1 | 6/2012 | Honigberg et al. | |
| 2013/0018032 A1 | 1/2013 | Chen et al. | |
| 2013/0079327 A1 | 3/2013 | Yamamoto et al. | |
| 2013/0338172 A1 * | 12/2013 | Smyth ................... A61K 45/06 514/262.1 |
| 2014/0073593 A1 | 3/2014 | Conklin et al. | |
| 2014/0179673 A1 | 3/2014 | Evarts et al. | |

(Continued)

FOREIGN PATENT DOCUMENTS

| | | |
|---|---|---|
| EP | 2548877 | 1/2013 |
| WO | 2001019828 | 3/2001 |

(Continued)

OTHER PUBLICATIONS

Berge et al., "Pharmaceutical salts" 66(1) J. Pharm. Sci. 1-19 (1977).

(Continued)

*Primary Examiner* — Micah Paul Young
(74) *Attorney, Agent, or Firm* — Morgan, Lewis & Bockius, LLP

(57) ABSTRACT

Therapeutic methods of treating chronic lymphocytic leukemia (CLL) and small lymphocytic leukemia (SLL) are described. In certain embodiments, the invention includes therapeutic methods of treating CLL and SLL using a BTK inhibitor. In certain embodiments, the invention includes therapeutic methods of treating subtypes of CLL and SLL using a BTK inhibitor, including subtypes of CLL in patients sensitive to thrombosis and subtypes of CLL that increase monocytes and NK cells in peripheral blood after treatment with a BTK inhibitor. In certain embodiments, the invention includes therapeutic methods of treating CLL and SLL using a combination of a BTK inhibitor and an anti-CD20 antibody.

12 Claims, 17 Drawing Sheets

Specification includes a Sequence Listing.

(56) References Cited

U.S. PATENT DOCUMENTS

| | | | |
|---|---|---|---|
| 2014/0206681 | A1 | 7/2014 | Kim et al. |
| 2014/0212425 | A1 | 7/2014 | Chang et al. |
| 2014/0328832 | A1* | 11/2014 | Chopra ............... A61K 31/505 |
| | | | 514/266.22 |

FOREIGN PATENT DOCUMENTS

| | | |
|---|---|---|
| WO | 2007064993 | 6/2001 |
| WO | 2002080926 | 10/2002 |
| WO | 2003065995 | 8/2003 |
| WO | 2005037836 | 4/2005 |
| WO | 2005097800 | 10/2005 |
| WO | 2007061737 | 5/2007 |
| WO | 20070648 | 6/2007 |
| WO | 2007106503 | 9/2007 |
| WO | 2008121742 | 10/2008 |
| WO | 2009076170 | 6/2009 |
| WO | 2010126960 | 11/2010 |
| WO | 2011095556 | 8/2011 |
| WO | 2011119663 | 9/2011 |
| WO | 2011152351 | 12/2011 |
| WO | 2011153514 | 12/2011 |
| WO | 2012158843 | 11/2012 |
| WO | 2013003629 | 1/2013 |
| WO | 2013010380 | 1/2013 |
| WO | 2013010868 | 1/2013 |
| WO | 2013010868 A1 | 1/2013 |
| WO | 2013010869 | 1/2013 |
| WO | 2013059738 | 4/2013 |
| WO | 2015057992 A1 | 4/2014 |
| WO | 2014130856 A2 | 8/2014 |
| WO | 2014143807 | 9/2014 |
| WO | 2014159745 | 10/2014 |
| WO | 2014159745 | 2/2015 |
| WO | 2015083008 A1 | 6/2015 |

OTHER PUBLICATIONS

Bingham et al., "Over one hundred solvates of sulfathlazole" Chem. Commun. 603-04 (2001).

Caira et al., "Preparation and Crystal Characterization of a Polymorph, a Monohydrate, and an Ethyl Acetate Solvate of the Antifungal Fluconazole," 93(3) J. Pharma. Sci. 601-11 (2004).

Davis et al., "Chronic active B-cell-receptor signaling in diffuse large B-cell lymphoma," 463 Nature 88-92 (2010).

Dhar et al., "Synthesis and SAR of p38a MAP kinase inhibitors based on heterobicyclic scaffolds," 17 Bioorg. & Med. Chem. Lett. 5019-24 (2007).

Gaudet et al., "A Homogeneous Fluorescence Polarization Assay Adaptable for a Range of Protein Serine/Threonine and Tyrosine Kinases," 8(2) J. Biomol. Screening 164-75 (2003).

Gennaro et al., Remington: The Science and Practice of Pharmacy 20th edition (2000).

Gilfillan et al., "The tyrosine kinase network regulating mast cell activation," 288 Immun. Rev. 149-69 (2009).

Gould, "Salt selection for basic drugs" 33 Int'l J. Pharmaceutics 201-217 (1986).

Greene & Wuts, Protective Groups in Organic Synthesis, 2d Edition (1991).

Harder et al., "Gain- and Loss-of-Function Lyn Mutant Mice Define a Critical Inhibitory Role for Lyn in the Myeloid Lineage" 15 immunity 603-15 (2001).

Hartz et al., "Synthesis and Evaluation of imidazo[1,5•a]pyrazines as Corticotrophin Releasing Hormone Receptor Ligands," 12 Bioorg. & Med. Chem. Lett. 291-94 (2002).

Higuchi et al. (eds.), Pro-drugs as Novel Delivery Systems. 14 A.C.S. Symposium Series (1975).

Ji et al., "A novel, potent, and selective insulin-like growth factor-I receptor kinase inhibitor blocks insulin-like growth factor-I receptor signaling in vitro and inhibits insulin-like growth factor-I receptor-dependent tumor growth in vivo," 6(8) Mol Cancer Ther. 2158-67 (2007).

King et al., "Nucleofugallty effects in the pyridine promoted formation of esters from 2-substituted ethanesulfonyl chlorides," 66 Can. J. Chem. 1109-16 (1988).

Klinghoffer et al., "Src family kinases are required for integrin but not PDGFR signal transduction," 18(9) EMBO J. 2459-71 (1999).

Lim et al., "Anti-CD20 monoclonal antibodies: historical and future perspectives," 95(1) Hematological 135-43 (2010).

Lowell et al., "Deficiency of the Hck and Src Tyrosine Kinases Results in Extreme Levels of Extramedullary Hematopoiesis," 87(5) Blood 1780-92 (1996).

Mitchell et al., Synthesis of C-nucleoside isosteres of 9-(2-hydroxyethoxymethyl)guanine (acyclovir), 21 (3) J. Heterocyclic Chem. 697-99 (1984).

Mukaiyama et al., "Synthesis and c-Src inhibitory activity of imidazo[1,5-a]pyrazine derivatives as an agent for treatment of acute ischemic stroke," 15 Bioorg Med. Chem. 868-85 (2007).

Mulvihill et al., "1,3-Disubstituted-imidazo[1,5-a]pyrazines as insulin-like growth-factor-I receptor (IGF-IR) inhibitors", 17 Bioorg. & Med. Chem. Lett. 1091-97 (2007).

Mulvihill et al., "Novel 2-phenylquinolin 7-yl-derived imidazo[1,5-a]pyrazines as potent insulin-growth factor-I receptor (IGF-IR) inhibitors", 16 Bioorg. & Med. Chem. 1359-75 (2008).

Odom et al., "Negative Regulation of immunoglobulin E-dependent Allergic Responses by Lyn Kinase," 199(11) J. Exp. Med. 1491-1502 (2004).

Pan et al., "Discovery of Selective Irreversible Inhibitors for Bruton's Tyrosine Kinase," 2 ChemMedChem 58-61 (2007).

Roby et al., "Alterations in Reproductive Function in Src Tyrosine Kinase Knockout Mice", 26 Endocrine 169-76 (2005).

Roche, Bioreversible Carriers in Drug Design, Pergamon Press (1987).

Shinohara et al., "Tyrosine Kinases Btk and Tec Regulate Osteoclast Differentiation by Linking RANK and ITAM Signals" 132 Cell 794-806 (2008).

Van Tonder et al., "Preparation and Physicochemical Characterization of 5 Niclosamide Solvates and 1 Hemisolvate", 5(1) AAPS PharmSciTech Article 12 (2004).

Written Opinion dated Aug. 10, 2016 relating to PCT/IB2016/053988.

International Search Report dated Aug. 10, 2016 relating to PCT/IB2016/053988.

Byrd et al., "Acalabrutinib (ACP-196) in Relapsed Chronic Lymphocytic Leukemia", N Engl J Med, vol. 374, No. 5, pp. 323-332 (2016).

International Search Report for PCT/IB2015/000645, dated Aug. 31, 2015.

Written Opinion for PCT/IB2015/000645.

International Search Report for PCT/IB2015/002140, dated Feb. 28, 2016.

Written Opinion for PCT/IB2015/002140.

Calquence Prescribing Information dated Oct. 2017.

Imbruvica Prescribing Information dated Nov. 2013.

Imbruvica Prescribing Information dated Feb. 2014.

Bruce D. Cheson, et al., Advancements in the Treatment of B-Cell Malignancies (International Conference on Malignant Lymphoma), Clinical Advances in Hematology & Oncology, vol. 11, Issue 9, Supplement 12 (Sep. 2013).

Ranjana H. Advani, et al., Bruton Tyrosine Kinase Inhibitor Ibrutinib (PCI-32765) Has Significant Activity in Patients With Relapsed/Refractory B-Cell Malignancies, J. Clinical Oncology31(1):88-94 (Jan. 2013).

Stefano A. Pileri, et al., Mantle cell lymphoma, Haematololgica 94(11):1488-92 (2009).

M. Dreyling, et al., Howto manage mantle cell lymphoma, Leukemia 28:2117-31 (2014).

Akintunde Akinleye, et al., Ibrutinib and novel BTK inhibitors in clinical development, J. of Hematology & Oncology 6:59 (2013).

Claire V. Hutchinson, et al., Breaking good: the inexorable rise of BTK inhibitors in the treatment of chronic lymphocytic leukaemia, British J. of Haematology 166:12-22 (2014).

Jennifer R. Brown, et al., Phase 1 Study of Single Agent CC-292, a Highly Selective Bruton's Tyrosine Kinase (BTK) Inhibitor, in Relapsed/Refractory Chronic Lymphocytic Leukemia (CLL), Blood 122(21):1630 (2013).

(56) References Cited

OTHER PUBLICATIONS

Daniel W. Pierce, et al., Target Engagement, Pathway Inhibition, and Efficacy of the Bruton's Tyrosine Kinase (Btk) Inhibitor CC-292, Blood 122(21):4169 (2013).

Simon Rule, et al., A Phase I Study of the Oral Btk Inhibitor ONO-4059 in Patients With Relapsed/Refractory B-Cell Lymphoma, Blood 122(21):4397 (2013).

International Conference on Harmonisation; Dose-Response Information to Support Drug Registration; Guideline; Availability, 59 Fed. Reg. 55,972 (Nov. 9, 1994).

U.S. Food and Drug Administration, Guidance for Industry—S9 Nonclinical Evaluation for Anticancer Pharmaceuticals (Mar. 2010) ("S9 Guidance").

U.S. Food and Drug Administration, Guidance for Industry—Estimating the Maximum Safe Starting Dose in Initial Clinical Trials for Therapeutics in Adult Healthy Volunteers (Jul. 2005) ("MSSD Guidance").

Erica K. Evans, et al., Inhibition of Btk with CC-292 Provides Early Pharmacodynamic Assessment of Activity in Mice and Humans, J. Pharmacology and Experimental Therapeutics 346:219-228 (Aug. 2013) ("Evans").

Tjeerd Barf, et al., Irreversible Protein Kinase Inhibitors: Balancing the Benefits and Risks, J. Med. Chem. 55:6243-62 (2012) ("Barf 2012").

Amit Mahipal, et al., Risks and Benefits of Phase 1 Clinical Trial Participation, Cancer Control 21:193-99 (Jul. 2014).

Sarah Brumskill, et al., Conference Scene: Recent developments in the understanding and treatment of hematological malignancies, Int'l J. Hematologic Oncology, vol. 2, No. 5, published online at https://doi.org/10.2217/jh.13.52 (Oct. 8, 2013).

Toshio Yoshizawa, et al., ONO-4059—a Potent and Selective Reversible Bruton's Tyrosine Kinase (Btk) Inhibitor: Single Agent, Twice Daily (BD) Dosing and Dosing with Food Results in Sustained, High Trough Levels of ONO-4059, Translating into 100% Tumour Remission in a TMD-8 Xenograft Model, Blood, 124(21):4502 (2014).

JP2023-00478 against U.S. Pat. No. 10,272,083, filed on Feb. 3, 2023.

Jan de Jong, et al., Effect of CYP3A perpetrators on ibrutinib exposure in healthy participants, Pharmacology Research & Perspectives, vol. 3, Issue 4 (2015).

Dominique Levêque, Evaluation of Fixed Dosing of New Anticancer Agents in Phase I Studies, Anticancer Research 28:3075-78 (2008).

Betty Y. Chang, et al., Egress of CD19\CD5\ cells into peripheral blood following treatment with the Bruton tyrosine kinase inhibitor ibrutinib in mantle cell lymphoma patients, Blood 122(14):2142 (2013).

Yan Bao, et al., Tyrosine Kinase Btk Is Required for NK Cell Activation, J. Biological Chemistry 287(28):123769 (2012).

\* cited by examiner

METHODS OF TREATING CHRONIC LYMPHOCYTIC LEUKEMIA AND SMALL LYMPHOCYTIC LEUKEMIA USING A BTK INHIBITOR

The subject matter disclosed herein was developed and the claimed invention was made by or on behalf of one or more of the following parties to a joint research agreement: Covalution Pharma B.V. (a/k/a Acerta Pharma B.V.) and MSD Oss B.V. (a predecessor-in-interest to Merck Sharp & Dohme B.V.). The joint research agreement was in effect on and before the effective filing date of the claimed invention and the date the claimed invention was made, and the claimed invention was made as a result of activities undertaken within the scope of the joint research agreement.

FIELD OF THE INVENTION

Therapeutic methods of treating chronic lymphocytic leukemia using a Bruton's tyrosine kinase (BTK) inhibitor are disclosed herein.

BACKGROUND OF THE INVENTION

Bruton's Tyrosine Kinase (BTK or Btk) is a TEC family non-receptor protein kinase expressed in B cells and myeloid cells. The function of BTK in signaling pathways activated by the engagement of the B cell receptor (BCR) and FCER1 on mast cells is well established. Functional mutations in BTK in humans result in a primary immunodeficiency disease characterized by a defect in B cell development with a block between pro- and pre-B cell stages. The result is an almost complete absence of B lymphocytes, causing a pronounced reduction of serum immunoglobulin of all classes. These findings support a key role for BTK in the regulation of the production of auto-antibodies in auto-immune diseases.

Other diseases with an important role for dysfunctional B cells are B cell malignancies. The reported role for BTK in the regulation of proliferation and apoptosis of B cells indicates the potential for BTK inhibitors in the treatment of B cell lymphomas. BTK inhibitors have thus been developed as potential therapies, as described in O. J. D'Cruz and F. M. Uckun, *OncoTargets and Therapy* 2013, 6, 161-176.

B cell chronic lymphocytic leukemia (CLL) is one of the most prevalent B cell malignancies in adults. CLL is characterized by an expansion of monoclonal mature B cells. CLL patients who relapsed after standard treatments generally experience poor outcomes. Although survival has been improved by the addition of immunotherapies such as rituximab to standard chemotherapies such as fludarabine and cyclophosphamide, as described in M. Hallek, et al., *Lancet*, 2010, 76, 1164-74, many standard treatments are associated with toxicities and immunosuppression. There is therefore a significant need to identify less toxic and highly efficacious treatments for CLL. Small lymphocytic leukemia (SLL) is closely related to CLL, and differs only in that a lower level of monoclonal lymphocytes is observed in blood than in CLL, along with an enlarged spleen or lymph nodes. There is also a significant need to identify less toxic and highly efficacious treatments for SLL.

CLL (and SLL) cells rapidly accumulate and are resistant to apoptosis in vivo, but are known to die rapidly in vitro. M. Buchner, et al., *Blood* 2010, 115, 4497-506. One cause of this effect is from nonmalignant accessory cells in the tumor microenvironment, such as stromal cell contact mediated cell survival. Stromal cells in the bone marrow and lymph nodes are known to have an antiapoptotic and protective effect on CLL cells, protecting them from both chemotherapeutic and spontaneous apoptosis. R. E. Mudry, et al., *Blood* 2000, 96, 1926-32. The chemokine SDF1α (CXCL12) directs homing of CLL cells towards protective niches. M. Burger, et al., *Blood* 2005, 106, 1824-30. Existing drugs that target the BCR pathway in B cell malignancies can lead to some lymphocytosis, i.e. lymphocyte egress from nodal compartments, through disruption of CXCR4-SDF1α signaling and other adhesion factors in bone marrow and the resulting mobilization of cells. However, existing therapies may not eradicate residual malignant B cell populations in the microenvironment of the bone marrow and lymph nodes, where protective stromal cells prevent apoptosis. There is thus an urgent need for treatments that reduce or overcome the protective effect of the microenvironment on CLL cells to enable superior clinical responses in patients.

SUMMARY OF THE INVENTION

In an embodiment, the invention includes a method of treating CLL and/or SLL, comprising the step of orally administering, to a human in need thereof, a Bruton's tyrosine kinase (BTK) inhibitor, wherein the BTK inhibitor is (S)-4-(8-amino-3-(1-(but-2-ynoyl)pyrrolidin-2-yl)imidazo[1,5-a]pyrazin-1-yl)-N-(pyridin-2-yl)benzamide or a pharmaceutically acceptable salt, solvate, hydrate, cocrystal, or prodrug thereof.

In an embodiment, the invention includes a method of treating CLL and/or SLL, comprising the step of orally administering, to a human in need thereof, a Bruton's tyrosine kinase (BTK) inhibitor, wherein the BTK inhibitor is (S)-4-(8-amino-3-(1-(but-2-ynoyl)pyrrolidin-2-yl)imidazo[1,5-a]pyrazin-1-yl)-N-(pyridin-2-yl)benzamide or a pharmaceutically acceptable salt, solvate, hydrate, cocrystal, or prodrug thereof, wherein the BTK inhibitor is administered once daily at a dose selected from the group consisting of 100 mg, 175 mg, 250 mg, and 400 mg.

In an embodiment, the invention includes a method of treating CLL and/or SLL, comprising the step of orally administering, to a human in need thereof, a Bruton's tyrosine kinase (BTK) inhibitor, wherein the BTK inhibitor is (S)-4-(8-amino-3-(1-(but-2-ynoyl)pyrrolidin-2-yl)imidazo[1,5-a]pyrazin-1-yl)-N-(pyridin-2-yl)benzamide or a pharmaceutically acceptable salt, solvate, hydrate, cocrystal, or prodrug thereof, wherein the BTK inhibitor is administered twice daily at a dose of 100 mg.

In an embodiment, the invention includes a method of treating CLL and/or SLL, comprising the step of orally administering, to a human in need thereof, a Bruton's tyrosine kinase (BTK) inhibitor, wherein the BTK inhibitor is (S)-4-(8-amino-3-(1-(but-2-ynoyl)pyrrolidin-2-yl)imidazo[1,5-a]pyrazin-1-yl)-N-(pyridin-2-yl)benzamide or a pharmaceutically acceptable salt, solvate, hydrate, cocrystal, or prodrug thereof, wherein the CLL increases monocytes and NK cells in peripheral blood after treatment with Formula (II) for a period selected from the group consisting of about 14 days, about 28 days, or about 56 days.

In an embodiment, the invention includes a method of treating CLL and/or SLL, comprising the step of orally administering, to a human in need thereof, a Bruton's tyrosine kinase (BTK) inhibitor, wherein the BTK inhibitor is (S)-4-(8-amino-3-(1-(but-2-ynoyl)pyrrolidin-2-yl)imidazo[1,5-a]pyrazin-1-yl)-N-(pyridin-2-yl)benzamide or a pharmaceutically acceptable salt, solvate, hydrate, cocrystal, or prodrug thereof, wherein the CLL is selected from the group consisting of IgVH mutation negative CLL, ZAP-70 positive CLL, ZAP-70 methylated at CpG3 CLL, CD38 positive CLL, CLL with a 17p13.1 (17p) deletion, CLL with a 11q22.3 (11 q) deletion, CLL in a human sensitive to platelet-mediated thrombosis, CLL in a human presently suffering from platelet-mediated thrombosis, CLL in a human previously suffering from platelet-mediated thrombosis, or combinations thereof.

In an embodiment, the invention includes a method of treating CLL and/or SLL, comprising the step of orally administering, to a human in need thereof, a Bruton's tyrosine kinase (BTK) inhibitor, wherein the BTK inhibitor is (S)-4-(8-amino-3-(1-(but-2-ynoyl)pyrrolidin-2-yl)imidazo[1,5-a]pyrazin-1-yl)-N-(pyridin-2-yl)benzamide or a pharmaceutically acceptable salt, solvate, hydrate, cocrystal, or prodrug thereof, further comprising the step of administering a therapeutically effective dose of an anti-CD20 antibody selected from the group consisting of rituximab, obinutuzumab, ofatumumab, veltuzumab, tositumomab, ibritumomab, and fragments, derivatives, conjugates, variants, radioisotope-labeled complexes, and biosimilars thereof.

In an embodiment, the invention includes a method of treating CLL and/or SLL, comprising the step of orally administering, to a human in need thereof, a Bruton's tyrosine kinase (BTK) inhibitor, wherein the BTK inhibitor is (S)-4-(8-amino-3-(1-(but-2-ynoyl)pyrrolidin-2-yl)imidazo[1,5-a]pyrazin-1-yl)-N-(pyridin-2-yl)benzamide or a pharmaceutically acceptable salt, solvate, hydrate, cocrystal, or prodrug thereof, further comprising the step of administering a therapeutically effective dose of an anticoagulant or antiplatelet active pharmaceutical ingredient.

In an embodiment, the invention includes a method of treating CLL and/or SLL, comprising the step of orally administering, to a human in need thereof, a Bruton's tyrosine kinase (BTK) inhibitor, wherein the BTK inhibitor is (S)-4-(8-amino-3-(1-(but-2-ynoyl)pyrrolidin-2-yl)imidazo[1,5-a]pyrazin-1-yl)-N-(pyridin-2-yl)benzamide or a pharmaceutically acceptable salt, solvate, hydrate, cocrystal, or prodrug thereof, further comprising the step of administering a therapeutically effective dose of an anticoagulant or antiplatelet active pharmaceutical ingredient, wherein the anticoagulant or antiplatelet active pharmaceutical ingredient is selected from the group consisting of acenocoumarol, anagrelide, anagrelide hydrochloride, abciximab, aloxiprin, antithrombin, apixaban, argatroban, aspirin, aspirin with extended-release dipyridamole, beraprost, betrixaban, bivalirudin, carbasalate calcium, cilostazol, clopidogrel, clopidogrel bisulfate, cloricromen, dabigatran etexilate, darexaban, dalteparin, dalteparin sodium, defibrotide, dicumarol, diphenadione, dipyridamole, ditazole, desirudin, edoxaban, enoxaparin, enoxaparin sodium, eptifibatide, fondaparinux, fondaparinux sodium, heparin, heparin sodium, heparin calcium, idraparinux, idraparinux sodium, iloprost, indobufen, lepirudin, low molecular weight heparin, melagatran, nadroparin, otamixaban, parnaparin, phenindione, phenprocoumon, prasugrel, picotamide, prostacyclin, ramatroban, reviparin, rivaroxaban, sulodexide, terutroban, terutroban sodium, ticagrelor, ticlopidine, ticlopidine hydrochloride, tinzaparin, tinzaparin sodium, tirofiban, tirofiban hydrochloride, treprostinil, treprostinil sodium, triflusal, vorapaxar, warfarin, warfarin sodium, ximelagatran, salts thereof, solvates thereof, hydrates thereof, and combinations thereof.

In an embodiment, the invention includes a method of treating a hematological malignancy in a human comprising the step of administering a therapeutically effective dose of a BTK inhibitor, wherein the BTK inhibitor is (S)-4-(8-amino-3-(1-(but-2-ynoyl)pyrrolidin-2-yl)imidazo[1,5-a]pyrazin-1-yl)-N-(pyridin-2-yl)benzamide or a pharmaceutically acceptable salt, solvate, hydrate, cocrystal, or prodrug thereof, and wherein the hematological malignancy is selected from the group consisting of non-Hodgkin's lymphoma (NHL), diffuse large B cell lymphoma (DLBCL), follicular lymphoma (FL), mantle cell lymphoma (MCL), Hodgkin's lymphoma, B cell acute lymphoblastic leukemia (B-ALL), Burkitt's lymphoma, Waldenström's macroglobulinemia (WM), Burkitt's lymphoma, multiple myeloma, or myelofibrosis.

In an embodiment, the invention includes a method of treating a hematological malignancy in a human comprising the step of administering a therapeutically effective dose of a BTK inhibitor, wherein the BTK inhibitor is (S)-4-(8-amino-3-(1-(but-2-ynoyl)pyrrolidin-2-yl)imidazo[1,5-a]pyrazin-1-yl)-N-(pyridin-2-yl)benzamide or a pharmaceutically acceptable salt, solvate, hydrate, cocrystal, or prodrug thereof, and wherein the hematological malignancy is selected from the group consisting of non-Hodgkin's lymphoma (NHL), diffuse large B cell lymphoma (DLBCL), follicular lymphoma (FL), mantle cell lymphoma (MCL), Hodgkin's lymphoma, B cell acute lymphoblastic leukemia (B-ALL), Burkitt's lymphoma, Waldenström's macroglobulinemia (WM), Burkitt's lymphoma, multiple myeloma, or myelofibrosis, wherein the BTK inhibitor is administered once daily at a dose selected from the group consisting of 100 mg, 175 mg, 250 mg, and 400 mg.

In an embodiment, the invention includes a method of treating a hematological malignancy in a human comprising the step of administering a therapeutically effective dose of a BTK inhibitor, wherein the BTK inhibitor is (S)-4-(8-amino-3-(1-(but-2-ynoyl)pyrrolidin-2-yl)imidazo[1,5-a]pyrazin-1-yl)-N-(pyridin-2-yl)benzamide or a pharmaceutically acceptable salt, solvate, hydrate, cocrystal, or prodrug thereof, and wherein the hematological malignancy is selected from the group consisting of non-Hodgkin's lymphoma (NHL), diffuse large B cell lymphoma (DLBCL), follicular lymphoma (FL), mantle cell lymphoma (MCL), Hodgkin's lymphoma, B cell acute lymphoblastic leukemia (B-ALL), Burkitt's lymphoma, Waldenström's macroglobulinemia (WM), Burkitt's lymphoma, multiple myeloma, or myelofibrosis, wherein the BTK inhibitor is administered twice daily at a dose of 100 mg.

In an embodiment, the invention includes a method of treating a hematological malignancy in a human comprising the step of administering a therapeutically effective dose of a BTK inhibitor, wherein the BTK inhibitor is (S)-4-(8-amino-3-(1-(but-2-ynoyl)pyrrolidin-2-yl)imidazo[1,5-a]pyrazin-1-yl)-N-(pyridin-2-yl)benzamide or a pharmaceutically acceptable salt, solvate, hydrate, cocrystal, or prodrug thereof, and wherein the hematological malignancy is selected from the group consisting of non-Hodgkin's lymphoma (NHL), diffuse large B cell lymphoma (DLBCL), follicular lymphoma (FL), mantle cell lymphoma (MCL), Hodgkin's lymphoma, B cell acute lymphoblastic leukemia (B-ALL), Burkitt's lymphoma, Waldenström's macroglobulinemia (WM), Burkitt's lymphoma, multiple myeloma, or myelofibrosis, wherein the hematological malignancy increases monocytes and NK cells in peripheral blood after treatment with Formula (II) for a period selected from the group consisting of about 14 days, about 28 days, or about 56 days.

In an embodiment, the invention includes a method of treating a hematological malignancy in a human comprising the step of administering a therapeutically effective dose of a BTK inhibitor, wherein the BTK inhibitor is (S)-4-(8-amino-3-(1-(but-2-ynoyl)pyrrolidin-2-yl)imidazo[1,5-a]

pyrazin-1-yl)-N-(pyridin-2-yl)benzamide or a pharmaceutically acceptable salt, solvate, hydrate, cocrystal, or prodrug thereof, and wherein the hematological malignancy is non-Hodgkin's lymphoma (NHL), wherein the NHL is selected from the group consisting of indolent NHL and aggressive NHL.

In an embodiment, the invention includes a method of treating a hematological malignancy in a human comprising the step of administering a therapeutically effective dose of a BTK inhibitor, wherein the BTK inhibitor is (S)-4-(8-amino-3-(1-(but-2-ynoyl)pyrrolidin-2-yl)imidazo[1,5-a]pyrazin-1-yl)-N-(pyridin-2-yl)benzamide or a pharmaceutically acceptable salt, solvate, hydrate, cocrystal, or prodrug thereof, and wherein the hematological malignancy is diffuse large B cell lymphoma (DLBCL), wherein the DLBCL is selected from the group consisting of activated B-cell like diffuse large B-cell lymphoma (DLBCL-ABC) and germinal center B-cell like diffuse large B-cell lymphoma (DLBCL-GCB).

In an embodiment, the invention includes a method of treating a hematological malignancy in a human comprising the step of administering a therapeutically effective dose of a BTK inhibitor, wherein the BTK inhibitor is (S)-4-(8-amino-3-(1-(but-2-ynoyl)pyrrolidin-2-yl)imidazo[1,5-a]pyrazin-1-yl)-N-(pyridin-2-yl)benzamide or a pharmaceutically acceptable salt, solvate, hydrate, cocrystal, or prodrug thereof, and wherein the hematological malignancy is mantle cell lymphoma (MCL), wherein the MCL is selected from the group consisting of mantle zone MCL, nodular MCL, diffuse MCL, and blastoid MCL.

In an embodiment, the invention includes a method of treating a hematological malignancy in a human comprising the step of administering a therapeutically effective dose of a BTK inhibitor, wherein the BTK inhibitor is (S)-4-(8-amino-3-(1-(but-2-ynoyl)pyrrolidin-2-yl)imidazo[1,5-a]pyrazin-1-yl)-N-(pyridin-2-yl)benzamide or a pharmaceutically acceptable salt, solvate, hydrate, cocrystal, or prodrug thereof, and wherein the hematological malignancy is B cell acute lymphoblastic leukemia (B-ALL), wherein the B-ALL is selected from the group consisting of early pre-B cell B-ALL, pre-B cell B-ALL, and mature B cell B-ALL.

In an embodiment, the invention includes a method of treating a hematological malignancy in a human comprising the step of administering a therapeutically effective dose of a BTK inhibitor, wherein the BTK inhibitor is (S)-4-(8-amino-3-(1-(but-2-ynoyl)pyrrolidin-2-yl)imidazo[1,5-a]pyrazin-1-yl)-N-(pyridin-2-yl)benzamide or a pharmaceutically acceptable salt, solvate, hydrate, cocrystal, or prodrug thereof, and wherein the hematological malignancy is Burkitt's lymphoma, wherein the Burkitt's lymphoma is selected from the group consisting of sporadic Burkitt's lymphoma, endemic Burkitt's lymphoma, and human immunodeficiency virus-associated Burkitt's lymphoma.

In an embodiment, the invention includes a method of treating a hematological malignancy in a human comprising the step of administering a therapeutically effective dose of a BTK inhibitor, wherein the BTK inhibitor is (S)-4-(8-amino-3-(1-(but-2-ynoyl)pyrrolidin-2-yl)imidazo[1,5-a]pyrazin-1-yl)-N-(pyridin-2-yl)benzamide or a pharmaceutically acceptable salt, solvate, hydrate, cocrystal, or prodrug thereof, and wherein the hematological malignancy is multiple myeloma, wherein the multiple myeloma is selected from the group consisting of hyperdiploid multiple myeloma and non-hyperdiploid multiple myeloma.

In an embodiment, the invention includes a method of treating a hematological malignancy in a human comprising the step of administering a therapeutically effective dose of a BTK inhibitor, wherein the BTK inhibitor is (S)-4-(8-amino-3-(1-(but-2-ynoyl)pyrrolidin-2-yl)imidazo[1,5-a]pyrazin-1-yl)-N-(pyridin-2-yl)benzamide or a pharmaceutically acceptable salt, solvate, hydrate, cocrystal, or prodrug thereof, and wherein the hematological malignancy is myelofibrosis, wherein the myelofibrosis is selected from the group consisting of primary myelofibrosis, myelofibrosis secondary to polycythemia vera, and myelofibrosis secondary to essential thrombocythaemia.

In an embodiment, the invention includes a method of treating a hematological malignancy in a human comprising the step of administering a therapeutically effective dose of a BTK inhibitor, wherein the BTK inhibitor is (S)-4-(8-amino-3-(1-(but-2-ynoyl)pyrrolidin-2-yl)imidazo[1,5-a]pyrazin-1-yl)-N-(pyridin-2-yl)benzamide or a pharmaceutically acceptable salt, solvate, hydrate, cocrystal, or prodrug thereof, and wherein the hematological malignancy is selected from the group consisting of non-Hodgkin's lymphoma (NHL), diffuse large B cell lymphoma (DLBCL), follicular lymphoma (FL), mantle cell lymphoma (MCL), Hodgkin's lymphoma, B cell acute lymphoblastic leukemia (B-ALL), Burkitt's lymphoma, Waldenström's macroglobulinemia (WM), Burkitt's lymphoma, multiple myeloma, or myelofibrosis, further comprising the step of administering a therapeutically effective dose of an anti-CD20 antibody selected from the group consisting of rituximab, obinutuzumab, ofatumumab, veltuzumab, tositumomab, ibritumomab, and fragments, derivatives, conjugates, variants, radioisotope-labeled complexes, and biosimilars thereof.

In an embodiment, the invention includes a method of treating a hematological malignancy in a human comprising the step of administering a therapeutically effective dose of a BTK inhibitor, wherein the BTK inhibitor is (S)-4-(8-amino-3-(1-(but-2-ynoyl)pyrrolidin-2-yl)imidazo[1,5-a]pyrazin-1-yl)-N-(pyridin-2-yl)benzamide or a pharmaceutically acceptable salt, solvate, hydrate, cocrystal, or prodrug thereof, and wherein the hematological malignancy is selected from the group consisting of non-Hodgkin's lymphoma (NHL), diffuse large B cell lymphoma (DLBCL), follicular lymphoma (FL), mantle cell lymphoma (MCL), Hodgkin's lymphoma, B cell acute lymphoblastic leukemia (B-ALL), Burkitt's lymphoma, Waldenström's macroglobulinemia (WM), Burkitt's lymphoma, multiple myeloma, or myelofibrosis, further comprising the step of administering a therapeutically effective dose of an anticoagulant or antiplatelet active pharmaceutical ingredient.

In an embodiment, the invention includes a method of treating a hematological malignancy in a human comprising the step of administering a therapeutically effective dose of a BTK inhibitor, wherein the BTK inhibitor is (S)-4-(8-amino-3-(1-(but-2-ynoyl)pyrrolidin-2-yl)imidazo[1,5-a]pyrazin-1-yl)-N-(pyridin-2-yl)benzamide or a pharmaceutically acceptable salt, solvate, hydrate, cocrystal, or prodrug thereof, and wherein the hematological malignancy is selected from the group consisting of non-Hodgkin's lymphoma (NHL), diffuse large B cell lymphoma (DLBCL), follicular lymphoma (FL), mantle cell lymphoma (MCL), Hodgkin's lymphoma, B cell acute lymphoblastic leukemia (B-ALL), Burkitt's lymphoma, Waldenström's macroglobulinemia (WM), Burkitt's lymphoma, multiple myeloma, or myelofibrosis, further comprising the step of administering a therapeutically effective dose of an anticoagulant or antiplatelet active pharmaceutical ingredient, wherein the anticoagulant or antiplatelet active pharmaceutical ingredient is selected from the group consisting of acenocoumarol, anagrelide, anagrelide hydrochloride, abciximab, aloxiprin, antithrombin, apixaban, argatroban, aspirin, aspirin with extended-release dipyridamole, beraprost, betrixaban, bivalirudin, carbasalate calcium, cilostazol, clopidogrel, clopidogrel bisulfate, cloricromen, dabigatran etexilate, darexaban, dalteparin, dalteparin sodium, defibrotide, dicumarol, diphenadione, dipyridamole, ditazole, desirudin, edoxaban, enoxaparin, enoxaparin sodium, eptifibatide, fondaparinux, fondaparinux sodium, heparin, heparin sodium, heparin calcium, idraparinux, idraparinux sodium, iloprost, indobufen, lepirudin, low molecular weight heparin, melagatran, nadroparin, otamixaban, parnaparin, phenindione, phenprocoumon, prasugrel, picotamide, prostacyclin, ramatroban, reviparin, rivaroxaban, sulodexide, terutroban, terutroban sodium, ticagrelor, ticlopidine, ticlopidine hydrochloride, tinzaparin, tinzaparin sodium, tirofiban, tirofiban hydrochloride, treprostinil, treprostinil sodium, triflusal, vorapaxar, warfarin, warfarin sodium, ximelagatran, salts thereof, solvates thereof, hydrates thereof, and combinations thereof.

BRIEF DESCRIPTION OF THE DRAWINGS

The foregoing summary, as well as the following detailed description of the invention, will be better understood when read in conjunction with the appended drawings.

BRIEF DESCRIPTION OF THE SEQUENCE LISTINGS

Figure 1:
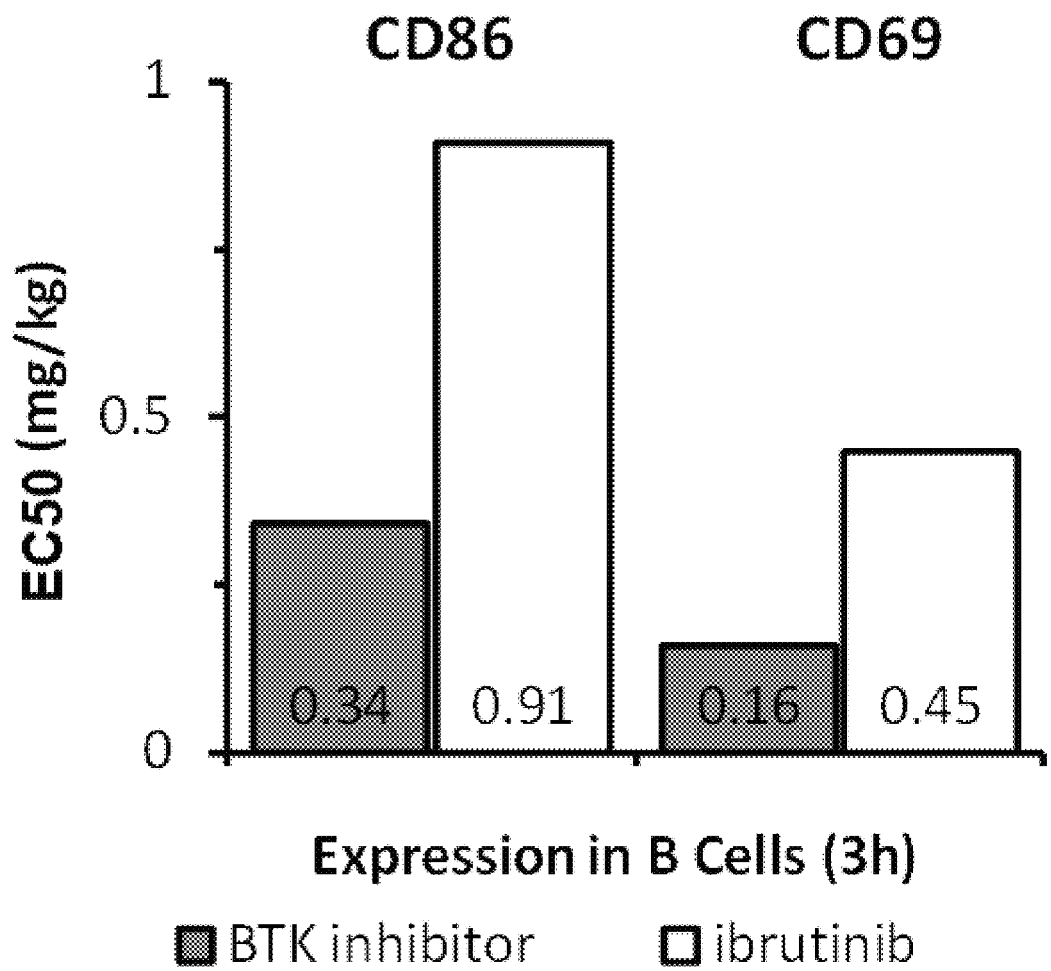
FIG. 1 illustrates in vivo potency of Formula (II) (labeled "BTK inhibitor") and ibrutinib. Mice were gavaged at increasing drug concentration and sacrificed at one time point (3 h post-dose). BCR is stimulated with IgM and the expression of activation markers CD69 and CD86 are monitored by flow cytometry to determine $EC_{50}$'s. The results show that Formula (II) is more potent at inhibiting expression of activation makers than ibrutinib.

SEQ ID NO:1 is the heavy chain amino acid sequence of the anti-CD20 monoclonal antibody rituximab.

SEQ ID NO:2 is the light chain amino acid sequence of the anti-CD20 monoclonal antibody rituximab.

SEQ ID NO:3 is the heavy chain amino acid sequence of the anti-CD20 monoclonal antibody obinutuzumab.

SEQ ID NO:4 is the light chain amino acid sequence of the anti-CD20 monoclonal antibody obinutuzumab.

SEQ ID NO:5 is the variable heavy chain amino acid sequence of the anti-CD20 monoclonal antibody ofatumumab.

SEQ ID NO:6 is the variable light chain amino acid sequence of the anti-CD20 monoclonal antibody ofatumumab.

SEQ ID NO:7 is the Fab fragment heavy chain amino acid sequence of the anti-CD20 monoclonal antibody ofatumumab.

SEQ ID NO:8 is the Fab fragment light chain amino acid sequence of the anti-CD20 monoclonal antibody ofatumumab.

SEQ ID NO:9 is the heavy chain amino acid sequence of the anti-CD20 monoclonal antibody veltuzumab.

SEQ ID NO:10 is the light chain amino acid sequence of the anti-CD20 monoclonal antibody veltuzumab.

SEQ ID NO:11 is the heavy chain amino acid sequence of the anti-CD20 monoclonal antibody tositumomab.

SEQ ID NO:12 is the light chain amino acid sequence of the anti-CD20 monoclonal antibody tositumomab.

SEQ ID NO:13 is the heavy chain amino acid sequence of the anti-CD20 monoclonal antibody ibritumomab.

SEQ ID NO:14 is the light chain amino acid sequence of the anti-CD20 monoclonal antibody ibritumomab.

DETAILED DESCRIPTION OF THE INVENTION

While preferred embodiments of the invention are shown and described herein, such embodiments are provided by way of example only and are not intended to otherwise limit the scope of the invention. Various alternatives to the described embodiments of the invention may be employed in practicing the invention.

Unless defined otherwise, all technical and scientific terms used herein have the same meaning as is commonly understood by one of skill in the art to which this invention belongs.

The terms "co-administration" and "administered in combination with" as used herein, encompass administration of two or more active pharmaceutical ingredients to a subject so that both agents and/or their metabolites are present in the subject at the same time. Co-administration includes simultaneous administration in separate compositions, administration at different times in separate compositions, or administration in a composition in which two or more agents are present.

The term "in vivo" refers to an event that takes place in a subject's body.

The term "in vitro" refers to an event that takes places outside of a subject's body. In vitro assays encompass cell-based assays in which cells alive or dead are employed and may also encompass a cell-free assay in which no intact cells are employed.

The term "$IC_{50}$" refers to the half maximal inhibitory concentration, i.e. inhibition of 50% of the desired activity. The term "$EC_{50}$" refers to the drug concentration at which one-half the maximum response is achieved.

The term "effective amount" or "therapeutically effective amount" refers to that amount of an active pharmaceutical ingredient or combination of active pharmaceutical ingredients as described herein that is sufficient to effect the intended application including, but not limited to, disease treatment. A therapeutically effective amount may vary depending upon the intended application (in vitro or in vivo), or the subject and disease condition being treated (e.g., the weight, age and gender of the subject), the severity of the disease condition, the manner of administration, and other factors which can readily be determined by one of ordinary skill in the art. The term also applies to a dose that will induce a particular response in target cells, (e.g., the reduction of platelet adhesion and/or cell migration). The specific dose will vary depending on the particular compounds chosen, the dosing regimen to be followed, whether the compound is administered in combination with other compounds, timing of administration, the tissue to which it is administered, and the physical delivery system in which the compound is carried.

A "therapeutic effect" as that term is used herein, encompasses a therapeutic benefit and/or a prophylactic benefit as described above. A prophylactic effect includes delaying or eliminating the appearance of a disease or condition, delaying or eliminating the onset of symptoms of a disease or condition, slowing, halting, or reversing the progression of a disease or condition, or any combination thereof.

The terms "QD," "qd," or "q.d." means quaque die, once a day, or once daily. The terms "BID," "bid," or "b.i.d." mean bis in die, twice a day, or twice daily. The terms "TID," "tid," or "t.i.d." mean ter in die, three times a day, or three times daily. The terms "QID," "qid," or "q.i.d." mean quater in die, four times a day, or four times daily.

The term "pharmaceutically acceptable salt" refers to salts derived from a variety of organic and inorganic counter ions known in the art. Pharmaceutically acceptable acid addition salts can be formed with inorganic acids and organic acids. Inorganic acids from which salts can be derived include, for example, hydrochloric acid, hydrobromic acid, sulfuric acid, nitric acid and phosphoric acid. Organic acids from which salts can be derived include, for example, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid and salicylic acid. Pharmaceutically acceptable base addition salts can be formed with inorganic and organic bases. Inorganic bases from which salts can be derived include, for example, sodium, potassium, lithium, ammonium, calcium, magnesium, iron, zinc, copper, manganese and aluminum. Organic bases from which salts can be derived include, for example, primary, secondary, and tertiary amines, substituted amines including naturally occurring substituted amines, cyclic amines and basic ion exchange resins. Specific examples include isopropylamine, trimethylamine, diethylamine, triethylamine, tripropylamine, and ethanolamine. In selected embodiments, the pharmaceutically acceptable base addition salt is chosen from ammonium, potassium, sodium, calcium, and magnesium salts. The term "cocrystal" refers to a molecular complex derived from a number of cocrystal formers known in the art. Unlike a salt, a cocrystal typically does not involve proton transfer between the cocrystal and the drug, and instead involves intermolecular interactions, such as hydrogen bonding, aromatic ring stacking, or dispersive forces, between the cocrystal former and the drug in the crystal structure.

"Pharmaceutically acceptable carrier" or "pharmaceutically acceptable excipient" is intended to include any and all solvents, dispersion media, coatings, antibacterial and antifungal agents, isotonic, and absorption delaying agents. The use of such media and agents for active pharmaceutical ingredients is well known in the art. Except insofar as any conventional media or agent is incompatible with the active pharmaceutical ingredient, its use in the therapeutic compositions of the invention is contemplated. Supplementary active ingredients can also be incorporated into the described compositions.

"Prodrug" is intended to describe a substance that may be converted under physiological conditions or by solvolysis to a biologically active pharmaceutical ingredient described herein. Thus, the term "prodrug" refers to a precursor of a biologically active compound that is pharmaceutically acceptable. A prodrug may be inactive when administered to a subject, but is converted in vivo to an active pharmaceutical ingredient, for example, by hydrolysis. The prodrug compound often offers the advantages of solubility, tissue compatibility or delayed release in a mammalian organism (see, e.g., H. Bundgaard, *Design of Prodrugs*, Elsevier, Amsterdam (1985)). The term "prodrug" is also intended to include any covalently bonded carriers, which release the active pharmaceutical ingredient in vivo when administered to a subject. Prodrugs of an active pharmaceutical ingredient, as described herein, may be prepared by modifying functional groups present in the active pharmaceutical ingredient in such a way that the modifications are cleaved, either in routine manipulation or in vivo, to yield the active pharmaceutical ingredient. Prodrugs include, for example, compounds wherein a hydroxy, amino or mercapto group is bonded to any group that, when the prodrug of the active pharmaceutical ingredient is administered to a mammalian subject, cleaves to form a free hydroxy, free amino or free mercapto group, respectively. Examples of prodrugs include, but are not limited to, acetates, formates and benzoate derivatives of an alcohol, various ester derivatives of a carboxylic acid, or acetamide, formamide and benzamide derivatives of an amine functional group in the active pharmaceutical ingredient.

When ranges are used herein to describe, for example, physical or chemical properties such as molecular weight or chemical formulae, all combinations and subcombinations of ranges and specific embodiments therein are intended to be included. Use of the term "about" when referring to a number or a numerical range means that the number or numerical range referred to is an approximation within experimental variability (or within statistical experimental error), and thus the number or numerical range may vary from, for example, between 1% and 15% of the stated number or numerical range. The term "comprising" (and related terms such as "comprise" or "comprises" or "having" or "including") includes those embodiments such as, for example, an embodiment of any composition of matter, method or process that "consist of" or "consist essentially of" the described features.

"Alkyl" refers to a straight or branched hydrocarbon chain radical consisting solely of carbon and hydrogen atoms, containing no unsaturation, having from one to ten carbon atoms (e.g., $C_1$-$C_{10}$ alkyl). Whenever it appears herein, a numerical range such as "1 to 10" refers to each integer in the given range—e.g., "1 to 10 carbon atoms" means that the alkyl group may consist of 1 carbon atom, 2 carbon atoms, 3 carbon atoms, etc., up to and including 10 carbon atoms, although the definition is also intended to cover the occurrence of the term "alkyl" where no numerical range is specifically designated. Typical alkyl groups include, but are in no way limited to, methyl, ethyl, propyl, isopropyl, n-butyl, isobutyl, sec-butyl isobutyl, tertiary butyl, pentyl, isopentyl, neopentyl, hexyl, septyl, octyl, nonyl and decyl. The alkyl moiety may be attached to the rest of the molecule by a single bond, such as for example, methyl (Me), ethyl (Et), n-propyl (Pr), 1-methylethyl (isopropyl), n-butyl, n-pentyl, 1,1-dimethylethyl (t-butyl) and 3-methylhexyl. Unless stated otherwise specifically in the specification, an alkyl group is optionally substituted by one or more of substituents which are independently alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, trimethylsilanyl, —OR$^a$, —SR$^a$, —OC(O)—R$^a$, —N(R$^a$)$_2$, —C(O)R$^a$, —C(O)OR$^a$, —OC(O)N(R$^a$)$_2$, —C(O)N(R$^a$)$_2$, —N(R$^a$)C(O)OR$^a$, —N(R$^a$)C(O)R$^a$, —N(R$^a$)C(O)N(R$^a$)$_2$, N(R$^a$)C(NR$^a$)N(R$^a$)$_2$, —N(R$^a$)S(O)$_t$R$^a$ (where t is 1 or 2), —S(O)$_t$OR$^a$ (where t is 1 or 2), —S(O)$_t$N(R$^a$)$_2$ (where t is 1 or 2), or PO$_3$(R$^a$)$_2$ where each R$^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

"Alkylaryl" refers to an -(alkyl)aryl radical where aryl and alkyl are as disclosed herein and which are optionally substituted by one or more of the substituents described as suitable substituents for aryl and alkyl respectively.

"Alkylhetaryl" refers to an -(alkyl)hetaryl radical where hetaryl and alkyl are as disclosed herein and which are optionally substituted by one or more of the substituents described as suitable substituents for aryl and alkyl respectively.

"Alkylheterocycloalkyl" refers to an -(alkyl) heterocycyl radical where alkyl and heterocycloalkyl are as disclosed herein and which are optionally substituted by one or more of the substituents described as suitable substituents for heterocycloalkyl and alkyl respectively.

An "alkene" moiety refers to a group consisting of at least two carbon atoms and at least one carbon-carbon double bond, and an "alkyne" moiety refers to a group consisting of at least two carbon atoms and at least one carbon-carbon triple bond. The alkyl moiety, whether saturated or unsaturated, may be branched, straight chain, or cyclic.

"Alkenyl" refers to a straight or branched hydrocarbon chain radical group consisting solely of carbon and hydrogen atoms, containing at least one double bond, and having from two to ten carbon atoms (i.e., $C_2$-$C_{10}$ alkenyl). Whenever it appears herein, a numerical range such as "2 to 10" refers to each integer in the given range—e.g., "2 to 10 carbon atoms" means that the alkenyl group may consist of 2 carbon atoms, 3 carbon atoms, etc., up to and including 10 carbon atoms. The alkenyl moiety may be attached to the rest of the molecule by a single bond, such as for example, ethenyl (i.e., vinyl), prop-1-enyl (i.e., allyl), but-1-enyl, pent-1-enyl and penta-1,4-dienyl. Unless stated otherwise specifically in the specification, an alkenyl group is optionally substituted by one or more substituents which are independently alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, trimethylsilanyl, —OR$^a$, —SR$^a$, —OC(O)—R$^a$, —N(R$^a$)$_2$, —C(O)R$^a$, —C(O)OR$^a$, —OC(O)N(R$^a$)$_2$, —C(O)N(R$^a$)$_2$, —N(R$^a$)C(O)OR$^a$, —N(R$^a$)C(O)R$^a$, —N(R$^a$)C(O)N(R$^a$)$_2$, N(R$^a$)C(NR$^a$)N(R$^a$)$_2$, —N(R$^a$)S(O)$_t$R$^a$ (where t is 1 or 2), —S(O)$_t$OR$^a$ (where t is 1 or 2), —S(O)$_t$N(R$^a$)$_2$ (where t is 1 or 2), or PO$_3$(R$^a$)$_2$, where each R$^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

"Alkenyl-cycloalkyl" refers to an -(alkenyl)cycloalkyl radical where alkenyl and cycloalkyl are as disclosed herein and which are optionally substituted by one or more of the substituents described as suitable substituents for alkenyl and cycloalkyl respectively.

"Alkynyl" refers to a straight or branched hydrocarbon chain radical group consisting solely of carbon and hydrogen atoms, containing at least one triple bond, having from two to ten carbon atoms (i.e. $C_2$-$C_{10}$ alkynyl). Whenever it appears herein, a numerical range such as "2 to 10" refers to each integer in the given range—e.g., "2 to 10 carbon atoms" means that the alkynyl group may consist of 2 carbon atoms, 3 carbon atoms, etc., up to and including 10 carbon atoms. The alkynyl may be attached to the rest of the molecule by a single bond, for example, ethynyl, propynyl, butynyl, pentynyl and hexynyl. Unless stated otherwise specifically in the specification, an alkynyl group is optionally substituted by one or more substituents which independently are: alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, trimethylsilanyl, —OR$^a$, —SR$^a$, —OC(O)—R$^a$, —N(R$^a$)$_2$, —C(O)R$^a$, —C(O)OR$^a$, —OC(O)N(R$^a$)$_2$, —C(O)N(R$^a$)$_2$, —N(R$^a$)C(O)OR$^a$, —N(R$^a$)C(O)R$^a$, —N(R$^a$)C(O)N(R$^a$)$_2$, N(R$^a$)C(NR$^a$)N(R$^a$)$_2$, —N(R$^a$)S(O)$_t$R$^a$ (where t is 1 or 2), —S(O)$_t$OR$^a$ (where t is 1 or 2), —S(O)$_t$N(R$^a$)$_2$ (where t is 1 or 2), or PO$_3$(R$^a$)$_2$, where each R$^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

"Alkynyl-cycloalkyl" refers to an -(alkynyl)cycloalkyl radical where alkynyl and cycloalkyl are as disclosed herein and which are optionally substituted by one or more of the substituents described as suitable substituents for alkynyl and cycloalkyl respectively.

"Carboxaldehyde" refers to a —(C=O)H radical.

"Carboxyl" refers to a —(C=O)OH radical.

"Cyano" refers to a —CN radical.

"Cycloalkyl" refers to a monocyclic or polycyclic radical that contains only carbon and hydrogen, and may be saturated, or partially unsaturated. Cycloalkyl groups include groups having from 3 to 10 ring atoms (i.e. C$_2$-C$_{10}$ cycloalkyl). Whenever it appears herein, a numerical range such as "3 to 10" refers to each integer in the given range—e.g., "3 to 10 carbon atoms" means that the cycloalkyl group may consist of 3 carbon atoms, etc., up to and including 10 carbon atoms. Illustrative examples of cycloalkyl groups include, but are not limited to the following moieties: cyclopropyl, cyclobutyl, cyclopentyl, cyclopentenyl, cyclohexyl, cyclohexenyl, cycloseptyl, cyclooctyl, cyclononyl, cyclodecyl, norbornyl, and the like. Unless stated otherwise specifically in the specification, a cycloalkyl group is optionally substituted by one or more substituents which independently are: alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, trimethylsilanyl, —OR$^a$, —SR$^a$, —OC(O)—R$^a$, —N(R$^a$)$_2$, —C(O)R$^a$, —C(O)OR$^a$, —OC(O)N(R$^a$)$_2$, —C(O)N(R$^a$)$_2$, —N(R$^a$)C(O)OR$^a$, —N(R$^a$)C(O)R$^a$, —N(R$^a$)C(O)N(R$^a$)$_2$, N(R$^a$)C(NR$^a$)N(R$^a$)$_2$, —N(R$^a$)S(O)$_t$R$^a$ (where t is 1 or 2), —S(O)$_t$OR$^a$ (where t is 1 or 2), —S(O)$_t$N(R$^a$)$_2$ (where t is 1 or 2), or PO$_3$(R$^a$)$_2$, where each R$^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

"Cycloalkyl-alkenyl" refers to a -(cycloalkyl)alkenyl radical where cycloalkyl and alkenyl are as disclosed herein and which are optionally substituted by one or more of the substituents described as suitable substituents for cycloalkyl and alkenyl, respectively.

"Cycloalkyl-heterocycloalkyl" refers to a -(cycloalkyl)heterocycloalkyl radical where cycloalkyl and heterocycloalkyl are as disclosed herein and which are optionally substituted by one or more of the substituents described as suitable substituents for cycloalkyl and heterocycloalkyl, respectively.

"Cycloalkyl-heteroaryl" refers to a -(cycloalkyl)heteroaryl radical where cycloalkyl and heteroaryl are as disclosed herein and which are optionally substituted by one or more of the substituents described as suitable substituents for cycloalkyl and heteroaryl, respectively.

The term "alkoxy" refers to the group —O-alkyl, including from 1 to 8 carbon atoms of a straight, branched, cyclic configuration and combinations thereof attached to the parent structure through an oxygen. Examples include, but are not limited to, methoxy, ethoxy, propoxy, isopropoxy, cyclopropyloxy and cyclohexyloxy. "Lower alkoxy" refers to alkoxy groups containing one to six carbons.

The term "substituted alkoxy" refers to alkoxy wherein the alkyl constituent is substituted (i.e., —O-(substituted alkyl)). Unless stated otherwise specifically in the specification, the alkyl moiety of an alkoxy group is optionally substituted by one or more substituents which independently are: alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, trimethylsilanyl, —OR$^a$, —SR$^a$, —OC(O)—R$^a$, —N(R$^a$)$_2$, —C(O)R$^a$, —C(O)OR$^a$, —OC(O)N(R$^a$)$_2$, —C(O)N(R$^a$)$_2$, —N(R$^a$)C(O)OR$^a$, —N(R$^a$)C(O)R$^a$, —N(R$^a$)C(O)N(R$^a$)$_2$, N(R$^a$)C(NR$^a$)N(R$^a$)$_2$, —N(R$^a$)S(O)$_t$R$^a$ (where t is 1 or 2), —S(O)$_t$OR$^a$ (where t is 1 or 2), —S(O)$_t$N(R$^a$)$_2$ (where t is 1 or 2), or PO$_3$(R$^a$)$_2$, where each R$^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

The term "alkoxycarbonyl" refers to a group of the formula (alkoxy)(C=O)— attached through the carbonyl carbon wherein the alkoxy group has the indicated number of carbon atoms. Thus a C$_1$-C$_6$ alkoxycarbonyl group is an alkoxy group having from 1 to 6 carbon atoms attached through its oxygen to a carbonyl linker. "Lower alkoxycarbonyl" refers to an alkoxycarbonyl group wherein the alkoxy group is a lower alkoxy group.

The term "substituted alkoxycarbonyl" refers to the group (substituted alkyl)-O—C(O)— wherein the group is attached to the parent structure through the carbonyl functionality. Unless stated otherwise specifically in the specification, the alkyl moiety of an alkoxycarbonyl group is optionally substituted by one or more substituents which independently are: alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, trimethylsilanyl, —OR$^a$, —SR$^a$, —OC(O)—R$^a$, —N(R$^a$)$_2$, —C(O)R$^a$, —C(O)OR$^a$, —OC(O)N(R$^a$)$_2$, —C(O)N(R$^a$)$_2$, —N(R$^a$)C(O)OR$^a$, —N(R$^a$)C(O)R$^a$, —N(R$^a$)C(O)N(R$^a$)$_2$, N(R$^a$)C(NR$^a$)N(R$^a$)$_2$, —N(R$^a$)S(O)$_t$R$^a$ (where t is 1 or 2), —S(O)$_t$OR$^a$ (where t is 1 or 2), —S(O)$_t$N(R$^a$)$_2$ (where t is 1 or 2), or PO$_3$(R$^a$)$_2$, where each R$^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

"Acyl" refers to the groups (alkyl)-C(O)—, (aryl)-C(O)—, (heteroaryl)-C(O)—, (heteroalkyl)-C(O)— and (heterocycloalkyl)-C(O)—, wherein the group is attached to the parent structure through the carbonyl functionality. If the R radical is heteroaryl or heterocycloalkyl, the hetero ring or chain atoms contribute to the total number of chain or ring atoms. Unless stated otherwise specifically in the specification, the alkyl, aryl or heteroaryl moiety of the acyl group is optionally substituted by one or more substituents which are independently alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, trimethylsilanyl, —OR$^a$, —SR$^a$, —OC(O)—R$^a$, —N(R$^a$)$_2$, —C(O)R$^a$, —C(O)OR$^a$, —OC(O)N(R$^a$)$_2$, —C(O)N(R$^a$)$_2$, —N(R$^a$)C(O)OR$^a$, —N(R$^a$)C(O)R$^a$, —N(R$^a$)C(O)N(R$^a$)$_2$, N(R$^a$)C(NR$^a$)N(R$^a$)$_2$, —N(R$^a$)S(O)$_t$R$^a$ (where t is 1 or 2), —S(O)$_t$OR$^a$ (where t is 1 or 2), —S(O)$_t$N(R$^a$)$_2$ (where t is 1 or 2), or PO$_3$(R$^a$)$_2$, where each R$^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

"Acyloxy" refers to a R(C=O)O— radical wherein R is alkyl, aryl, heteroaryl, heteroalkyl or heterocycloalkyl, which are as described herein. If the R radical is heteroaryl or heterocycloalkyl, the hetero ring or chain atoms contribute to the total number of chain or ring atoms. Unless stated otherwise specifically in the specification, the R of an acyloxy group is optionally substituted by one or more substituents which independently are: alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, trimethylsilanyl, —$OR^a$, —$SR^a$, —$OC(O)$—$R^a$, —$N(R^a)_2$, —$C(O)R^a$, —$C(O)OR^a$, —$OC(O)N(R^a)_2$, —$C(O)N(R^a)_2$, —$N(R^a)C(O)OR^a$, —$N(R^a)C(O)R^a$, —$N(R^a)C(O)N(R^a)_2$, $N(R^a)C(NR^a)N(R^a)_2$, —$N(R^a)S(O)_tR^a$ (where t is 1 or 2), —$S(O)_tOR^a$ (where t is 1 or 2), —$S(O)_tN(R^a)_2$ (where t is 1 or 2), or $PO_3(R^a)_2$, where each $R^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

"Amino" or "amine" refers to a —$N(R^a)_2$ radical group, where each $R^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl, unless stated otherwise specifically in the specification. When a —$N(R^a)_2$ group has two $R^a$ substituents other than hydrogen, they can be combined with the nitrogen atom to form a 4-, 5-, 6- or 7-membered ring. For example, —$N(R^a)_2$ is intended to include, but is not limited to, 1-pyrrolidinyl and 4-morpholinyl. Unless stated otherwise specifically in the specification, an amino group is optionally substituted by one or more substituents which independently are: alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, trimethylsilanyl, —$OR^a$, —$SR^a$, —$OC(O)$—$R^a$, —$N(R^a)_2$, —$C(O)R^a$, —$C(O)OR^a$, —$OC(O)N(R^a)_2$, —$C(O)N(R^a)_2$, —$N(R^a)C(O)OR^a$, —$N(R^a)C(O)R^a$, —$N(R^a)C(O)N(R^a)_2$, $N(R^a)C(NR^a)N(R^a)_2$, —$N(R^a)S(O)_tR^a$ (where t is 1 or 2), —$S(O)_tOR^a$ (where t is 1 or 2), —$S(O)_tN(R^a)_2$ (where t is 1 or 2), or $PO_3(R^a)_2$, where each $R^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

The term "substituted amino" also refers to N-oxides of the groups —$NHR^d$, and $NR^dR^d$ each as described above. N-oxides can be prepared by treatment of the corresponding amino group with, for example, hydrogen peroxide or m-chloroperoxybenzoic acid.

"Amide" or "amido" refers to a chemical moiety with formula —$C(O)N(R)_2$ or —$NHC(O)R$, where R is selected from the group consisting of hydrogen, alkyl, cycloalkyl, aryl, heteroaryl (bonded through a ring carbon) and heteroalicyclic (bonded through a ring carbon), each of which moiety may itself be optionally substituted. The $R_2$ of —$N(R)_2$ of the amide may optionally be taken together with the nitrogen to which it is attached to form a 4-, 5-, 6- or 7-membered ring. Unless stated otherwise specifically in the specification, an amido group is optionally substituted independently by one or more of the substituents as described herein for alkyl, cycloalkyl, aryl, heteroaryl, or heterocycloalkyl. An amide may be an amino acid or a peptide molecule attached to a compound of Formula (I), thereby forming a prodrug. The procedures and specific groups to make such amides are known to those of skill in the art and can readily be found in seminal sources such as T. H. Greene and P. G. M. Wuts, *Protective Groups in Organic Synthesis*, $3^{rd}$ Ed., John Wiley & Sons, New York (1999).

"Aromatic" or "aryl" or "Ar" refers to an aromatic radical with six to ten ring atoms (e.g., $C_6$-$C_{10}$ aromatic or $C_6$-$C_{10}$ aryl) which has at least one ring having a conjugated pi electron system which is carbocyclic (e.g., phenyl, fluorenyl, and naphthyl). Bivalent radicals formed from substituted benzene derivatives and having the free valences at ring atoms are named as substituted phenylene radicals. Bivalent radicals derived from univalent polycyclic hydrocarbon radicals whose names end in "-yl" by removal of one hydrogen atom from the carbon atom with the free valence are named by adding "-idene" to the name of the corresponding univalent radical, e.g., a naphthyl group with two points of attachment is termed naphthylidene. Whenever it appears herein, a numerical range such as "6 to 10" refers to each integer in the given range; e.g., "6 to 10 ring atoms" means that the aryl group may consist of 6 ring atoms, 7 ring atoms, etc., up to and including 10 ring atoms. The term includes monocyclic or fused-ring polycyclic (i.e., rings which share adjacent pairs of ring atoms) groups. Unless stated otherwise specifically in the specification, an aryl moiety is optionally substituted by one or more substituents which are independently alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, trimethylsilanyl, —$OR^a$, —$SR^a$, —$OC(O)$—$R^a$, —$N(R^a)_2$, —$C(O)R^a$, —$C(O)OR^a$, —$OC(O)N(R^a)_2$, —$C(O)N(R^a)_2$, —$N(R^a)C(O)OR^a$, —$N(R^a)C(O)R^a$, —$N(R^a)C(O)N(R^a)_2$, $N(R^a)C(NR^a)N(R^a)_2$, —$N(R^a)S(O)_tR^a$ (where t is 1 or 2), —$S(O)_tOR^a$ (where t is 1 or 2), —$S(O)_tN(R^a)_2$ (where t is 1 or 2), or $PO_3(R^a)_2$, where each $R^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

"Aralkyl" or "arylalkyl" refers to an (aryl)alkyl-radical where aryl and alkyl are as disclosed herein and which are optionally substituted by one or more of the substituents described as suitable substituents for aryl and alkyl respectively.

"Ester" refers to a chemical radical of formula —COOR, where R is selected from the group consisting of alkyl, cycloalkyl, aryl, heteroaryl (bonded through a ring carbon) and heteroalicyclic (bonded through a ring carbon). The procedures and specific groups to make esters are known to those of skill in the art and can readily be found in seminal sources such as T. H. Greene and P. G. M. Wuts, *Protective Groups in Organic Synthesis*, $3^{rd}$ Ed., John Wiley & Sons, New York (1999). Unless stated otherwise specifically in the specification, an ester group is optionally substituted by one or more substituents which independently are: alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, trimethylsilanyl, —$OR^a$, —$SR^a$, —$OC(O)$—$R^a$, —$N(R^a)_2$, —$C(O)R^a$, —$C(O)OR^a$, —$OC(O)N(R^a)_2$, —$C(O)N(R^a)_2$, —$N(R^a)C(O)OR^a$, —$N(R^a)C(O)R^a$, —$N(R^a)C(O)N(R^a)_2$, $N(R^a)C(NR^a)N(R^a)_2$, —$N(R^a)S(O)_tR^a$ (where t is 1 or 2), —$S(O)_tOR^a$ (where t is 1 or 2), —$S(O)_tN(R^a)_2$ (where t is 1 or 2), or $PO_3(R^a)_2$, where each $R^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

"Fluoroalkyl" refers to an alkyl radical, as defined above, that is substituted by one or more fluoro radicals, as defined above, for example, trifluoromethyl, difluoromethyl, 2,2,2-trifluoroethyl, 1-fluoromethyl-2-fluoroethyl, and the like. The alkyl part of the fluoroalkyl radical may be optionally substituted as defined above for an alkyl group.

"Halo," "halide," or, alternatively, "halogen" is intended to mean fluoro, chloro, bromo or iodo. The terms "haloalkyl," "haloalkenyl," "haloalkynyl" and "haloalkoxy" include alkyl, alkenyl, alkynyl and alkoxy structures that are substituted with one or more halo groups or with combinations thereof. For example, the terms "fluoroalkyl" and "fluoroalkoxy" include haloalkyl and haloalkoxy groups, respectively, in which the halo is fluorine.

"Heteroalkyl," "heteroalkenyl," and "heteroalkynyl" include optionally substituted alkyl, alkenyl and alkynyl radicals and which have one or more skeletal chain atoms selected from an atom other than carbon, e.g., oxygen, nitrogen, sulfur, phosphorus or combinations thereof. A numerical range may be given—e.g., $C_1$-$C_4$ heteroalkyl which refers to the chain length in total, which in this example is 4 atoms long. A heteroalkyl group may be substituted with one or more substituents which independently are: alkyl, heteroalkyl, alkenyl, alkynyl, cycloalkyl, heterocycloalkyl, aryl, arylalkyl, heteroaryl, heteroarylalkyl, hydroxy, halo, cyano, nitro, oxo, thioxo, trimethylsilanyl, —OR$^a$, —SR$^a$, —OC(O)—R$^a$, —N(R$^a$)$_2$, —C(O)R$^a$, —C(O)OR$^a$, —OC(O)N(R$^a$)$_2$, —C(O)N(R$^a$)$_2$, —N(R$^a$)C(O)OR$^a$, —N(R$^a$)C(O)R$^a$, —N(R$^a$)C(O)N(R$^a$)$_2$, N(R$^a$)C(N-R$^a$)N(R$^a$)$_2$, —N(R$^a$)S(O)$_t$R$^a$ (where t is 1 or 2), —S(O)$_t$OR$^a$ (where t is 1 or 2), —S(O)$_t$N(R$^a$)$_2$ (where t is 1 or 2), or PO$_3$(R$^a$)$_2$, where each R$^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

"Heteroalkylaryl" refers to an -(heteroalkyl)aryl radical where heteroalkyl and aryl are as disclosed herein and which are optionally substituted by one or more of the substituents described as suitable substituents for heteroalkyl and aryl, respectively.

"Heteroalkylheteroaryl" refers to an -(heteroalkyl)heteroaryl radical where heteroalkyl and heteroaryl are as disclosed herein and which are optionally substituted by one or more of the substituents described as suitable substituents for heteroalkyl and heteroaryl, respectively.

"Heteroalkylheterocycloalkyl" refers to an -(heteroalkyl)heterocycloalkyl radical where heteroalkyl and heterocycloalkyl are as disclosed herein and which are optionally substituted by one or more of the substituents described as suitable substituents for heteroalkyl and heterocycloalkyl, respectively.

"Heteroalkylcycloalkyl" refers to an -(heteroalkyl)cycloalkyl radical where heteroalkyl and cycloalkyl are as disclosed herein and which are optionally substituted by one or more of the substituents described as suitable substituents for heteroalkyl and cycloalkyl, respectively.

"Heteroaryl" or "heteroaromatic" or "HetAr" refers to a 5- to 18-membered aromatic radical (e.g., $C_5$-$C_{13}$ heteroaryl) that includes one or more ring heteroatoms selected from nitrogen, oxygen and sulfur, and which may be a monocyclic, bicyclic, tricyclic or tetracyclic ring system. Whenever it appears herein, a numerical range such as "5 to 18" refers to each integer in the given range—e.g., "5 to 18 ring atoms" means that the heteroaryl group may consist of 5 ring atoms, 6 ring atoms, etc., up to and including 18 ring atoms. Bivalent radicals derived from univalent heteroaryl radicals whose names end in "-yl" by removal of one hydrogen atom from the atom with the free valence are named by adding "-idene" to the name of the corresponding univalent radical—e.g., a pyridyl group with two points of attachment is a pyridylidene. A N-containing "heteroaromatic" or "heteroaryl" moiety refers to an aromatic group in which at least one of the skeletal atoms of the ring is a nitrogen atom. The polycyclic heteroaryl group may be fused or non-fused. The heteroatom(s) in the heteroaryl radical are optionally oxidized. One or more nitrogen atoms, if present, are optionally quaternized. The heteroaryl may be attached to the rest of the molecule through any atom of the ring(s). Examples of heteroaryls include, but are not limited to, azepinyl, acridinyl, benzimidazolyl, benzindolyl, 1,3-benzodioxolyl, benzofuranyl, benzooxazolyl, benzo[d]thiazolyl, benzothiadiazolyl, benzo[b][1,4]dioxepinyl, benzo[b][1,4]oxazinyl, 1,4-benzodioxanyl, benzonaphthofuranyl, benzoxazolyl, benzodioxolyl, benzodioxinyl, benzoxazolyl, benzopyranyl, benzopyranonyl, benzofuranyl, benzofuranonyl, benzofurazanyl, benzothiazolyl, benzothienyl(benzothiophenyl), benzothieno[3,2-d]pyrimidinyl, benzotriazolyl, benzo[4,6]imidazo[1,2-a]pyridinyl, carbazolyl, cinnolinyl, cyclopenta[d]pyrimidinyl, 6,7-dihydro-5H-cyclopenta[4,5]thieno[2,3-d]pyrimidinyl, 5,6-dihydrobenzo[h]quinazolinyl, 5,6-dihydrobenzo[h]cinnolinyl, 6,7-dihydro-5H-benzo[6,7]cyclohepta[1,2-c]pyridazinyl, dibenzofuranyl, dibenzothiophenyl, furanyl, furazanyl, furanonyl, furo[3,2-c]pyridinyl, 5,6,7,8,9,10-hexahydrocycloocta[d]pyrimidinyl, 5,6,7,8,9,10-hexahydrocycloocta[d]pyridazinyl, 5,6,7,8,9,10-hexahydrocycloocta[d]pyridinyl, isothiazolyl, imidazolyl, indazolyl, indolyl, indazolyl, isoindolyl, indolinyl, isoindolinyl, isoquinolyl, indolizinyl, isoxazolyl, 5,8-methano-5,6,7,8-tetrahydroquinazolinyl, naphthyridinyl, 1,6-naphthyridinonyl, oxadiazolyl, 2-oxoazepinyl, oxazolyl, oxiranyl, 5,6,6a,7,8,9,10,10a-octahydrobenzo[h]quinazolinyl, 1-phenyl-1H-pyrrolyl, phenazinyl, phenothiazinyl, phenoxazinyl, phthalazinyl, pteridinyl, purinyl, pyranyl, pyrrolyl, pyrazolyl, pyrazolo[3,4-d]pyrimidinyl, pyridinyl, pyrido[3,2-d]pyrimidinyl, pyrido[3,4-d]pyrimidinyl, pyrazinyl, pyrimidinyl, pyridazinyl, pyrrolyl, quinazolinyl, quinoxalinyl, quinolinyl, isoquinolinyl, tetrahydroquinolinyl, 5,6,7,8-tetrahydroquinazolinyl, 5,6,7,8-tetrahydrobenzo[4,5]thieno[2,3-d]pyrimidinyl, 6,7,8,9-tetrahydro-5H-cyclohepta[4,5]thieno[2,3-d]pyrimidinyl, 5,6,7,8-tetrahydropyrido[4,5-c]pyridazinyl, thiazolyl, thiadiazolyl, thiapyranyl, triazolyl, tetrazolyl, triazinyl, thieno[2,3-d]pyrimidinyl, thieno[3,2-d]pyrimidinyl, thieno[2,3-c]pyridinyl, and thiophenyl (i.e. thienyl). Unless stated otherwise specifically in the specification, a heteroaryl moiety is optionally substituted by one or more substituents which are independently: alkyl, heteroalkyl, alkenyl, alkynyl, cycloalkyl, heterocycloalkyl, aryl, arylalkyl, heteroaryl, heteroarylalkyl, hydroxy, halo, cyano, nitro, oxo, thioxo, trimethylsilanyl, —OR$^a$, —SR$^a$, —OC(O)—R$^a$, —N(R$^a$)$_2$, —C(O)R$^a$, —C(O)OR$^a$, —OC(O)N(R$^a$)$_2$, —C(O)N(R$^a$)$_2$, —N(R$^a$)C(O)OR$^a$, —N(R$^a$)C(O)R$^a$, —N(R$^a$)C(O)N(R$^a$)$_2$, N(R$^a$)C(NR$^a$)N(R$^a$)$_2$, —N(R$^a$)S(O)$_t$R$^a$ (where t is 1 or 2), —S(O)$_t$OR$^a$ (where t is 1 or 2), —S(O)$_t$N(R$^a$)$_2$ (where t is 1 or 2), or PO$_3$(R$^a$)$_2$, where each R$^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

Substituted heteroaryl also includes ring systems substituted with one or more oxide (—O—) substituents, such as, for example, pyridinyl N-oxides.

"Heteroarylalkyl" refers to a moiety having an aryl moiety, as described herein, connected to an alkylene moiety, as described herein, wherein the connection to the remainder of the molecule is through the alkylene group.

"Heterocycloalkyl" refers to a stable 3- to 18-membered non-aromatic ring radical that comprises two to twelve carbon atoms and from one to six heteroatoms selected from nitrogen, oxygen and sulfur. Whenever it appears herein, a numerical range such as "3 to 18" refers to each integer in the given range—e.g., "3 to 18 ring atoms" means that the heterocycloalkyl group may consist of 3 ring atoms, 4 ring atoms, etc., up to and including 18 ring atoms. Unless stated otherwise specifically in the specification, the heterocycloalkyl radical is a monocyclic, bicyclic, tricyclic or tetracyclic ring system, which may include fused or bridged ring systems. The heteroatoms in the heterocycloalkyl radical may be optionally oxidized. One or more nitrogen atoms, if present, are optionally quaternized. The heterocycloalkyl radical is partially or fully saturated. The heterocycloalkyl may be attached to the rest of the molecule through any atom of the ring(s). Examples of such heterocycloalkyl radicals include, but are not limited to, dioxolanyl, thienyl[1,3] dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, and 1,1-dioxo-thiomorpholinyl. Unless stated otherwise specifically in the specification, a heterocycloalkyl moiety is optionally substituted by one or more substituents which independently are: alkyl, heteroalkyl, alkenyl, alkynyl, cycloalkyl, heterocycloalkyl, aryl, arylalkyl, heteroaryl, heteroarylalkyl, hydroxy, halo, cyano, nitro, oxo, thioxo, trimethylsilanyl, —OR$^a$, —SR$^a$, —OC(O)—R$^a$, —N(R$^a$)$_2$, —C(O)R$^a$, —C(O)OR$^a$, —OC(O)N(R$^a$)$_2$, —C(O)N(R$^a$)$_2$, —N(R$^a$)C(O)OR$^a$, —N(R$^a$)C(O)R$^a$, —N(R$^a$)C(O)N(R$^a$)$_2$, N(R$^a$)C(NR$^a$)N(R$^a$)$_2$, —N(R$^a$)S(O)$_t$R$^a$ (where t is 1 or 2), —S(O)$_t$OR$^a$ (where t is 1 or 2), —S(O)$_t$N(R$^a$)$_2$ (where t is 1 or 2), or PO$_3$(R$^a$)$_2$, where each R$^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

"Heterocycloalkyl" also includes bicyclic ring systems wherein one non-aromatic ring, usually with 3 to 7 ring atoms, contains at least 2 carbon atoms in addition to 1-3 heteroatoms independently selected from oxygen, sulfur, and nitrogen, as well as combinations comprising at least one of the foregoing heteroatoms; and the other ring, usually with 3 to 7 ring atoms, optionally contains 1-3 heteroatoms independently selected from oxygen, sulfur, and nitrogen and is not aromatic.

"Isomers" are different compounds that have the same molecular formula. "Stereoisomers" are isomers that differ only in the way the atoms are arranged in space—i.e., having a different stereochemical configuration. "Enantiomers" are a pair of stereoisomers that are non-superimposable mirror images of each other. A 1:1 mixture of a pair of enantiomers is a "racemic" mixture. The term "(±)" is used to designate a racemic mixture where appropriate. "Diastereoisomers" are stereoisomers that have at least two asymmetric atoms, but which are not mirror-images of each other. The absolute stereochemistry is specified according to the Cahn-Ingold-Prelog R—S system. When a compound is a pure enantiomer the stereochemistry at each chiral carbon can be specified by either R or S. Resolved compounds whose absolute configuration is unknown can be designated (+) or (−) depending on the direction (dextro- or levorotatory) which they rotate plane polarized light at the wavelength of the sodium D line. Certain of the compounds described herein contain one or more asymmetric centers and can thus give rise to enantiomers, diastereomers, and other stereoisomeric forms that can be defined, in terms of absolute stereochemistry, as (R)- or (S)-. The present chemical entities, pharmaceutical compositions and methods are meant to include all such possible isomers, including racemic mixtures, optically pure forms and intermediate mixtures. Optically active (R)- and (S)-isomers can be prepared using chiral synthons or chiral reagents, or resolved using conventional techniques. When the compounds described herein contain olefinic double bonds or other centers of geometric asymmetry, and unless specified otherwise, it is intended that the compounds include both E and Z geometric isomers.

"Enantiomeric purity" as used herein refers to the relative amounts, expressed as a percentage, of the presence of a specific enantiomer relative to the other enantiomer. For example, if a compound, which may potentially have an (R)- or an (S)-isomeric configuration, is present as a racemic mixture, the enantiomeric purity is about 50% with respect to either the (R)- or (S)-isomer. If that compound has one isomeric form predominant over the other, for example, 80% (S)- and 20% (R)-, the enantiomeric purity of the compound with respect to the (S)-isomeric form is 80%. The enantiomeric purity of a compound can be determined in a number of ways known in the art, including but not limited to chromatography using a chiral support, polarimetric measurement of the rotation of polarized light, nuclear magnetic resonance spectroscopy using chiral shift reagents which include but are not limited to lanthanide containing chiral complexes or the Pirkle alcohol, or derivatization of a compounds using a chiral compound such as Mosher's acid followed by chromatography or nuclear magnetic resonance spectroscopy.

"Moiety" refers to a specific segment or functional group of a molecule. Chemical moieties are often recognized chemical entities embedded in or appended to a molecule.

"Nitro" refers to the —NO$_2$ radical.

"Oxa" refers to the —O— radical.

"Oxo" refers to the =O radical.

"Tautomers" are structurally distinct isomers that interconvert by tautomerization. "Tautomerization" is a form of isomerization and includes prototropic or proton-shift tautomerization, which is considered a subset of acid-base chemistry. "Prototropic tautomerization" or "proton-shift tautomerization" involves the migration of a proton accompanied by changes in bond order, often the interchange of a single bond with an adjacent double bond. Where tautomerization is possible (e.g. in solution), a chemical equilibrium of tautomers can be reached. An example of tautomerization is keto-enol tautomerization. A specific example of keto-enol tautomerization is the interconversion of pentane-2,4-dione and 4-hydroxypent-3-en-2-one tautomers. Another example of tautomerization is phenol-keto tautomerization. A specific example of phenol-keto tautomerization is the interconversion of pyridin-4-ol and pyridin-4(1H)-one tautomers.

The terms "enantiomerically enriched," "enantiomerically pure," and "non-racemic," as used herein, refer to compositions in which the percent by weight of one enantiomer is greater than the amount of that one enantiomer in a control mixture of the racemic composition (e.g., greater than 1:1 by weight). For example, an enantiomerically enriched preparation of the (S)-enantiomer, means a preparation of the compound having greater than 50% by weight of the (S)-enantiomer relative to the (R)-enantiomer, such as at least 75% by weight, such as at least 80% by weight. In some embodiments, the enrichment can be significantly greater than 80% by weight, providing a "substantially enantiomerically enriched," "substantially enantiomerically pure," or a "substantially non-racemic" preparation, which refers to preparations of compositions which have at least 85% by weight of one enantiomer relative to the other enantiomer, such as at least 90% by weight, and such as at least 95% by weight. The terms "diastereomerically enriched" and "diastereomerically pure," as used herein, refer to compositions in which the percent by weight of one diastereomer is greater than the amount of that one diastereomer in a control mixture of diastereomers. In some embodiments, the enrichment can be significantly greater than 80% by weight, providing a "substantially diastereomerically enriched" or "substantially diastereomerically pure" preparation, which refers to preparations of compositions which have at least 85% by weight of one diastereomer relative to other diastereomers, such as at least 90% by weight, and such as at least 95% by weight.

In preferred embodiments, the enantiomerically enriched composition has a higher potency with respect to therapeutic utility per unit mass than does the racemic mixture of that composition. Enantiomers can be isolated from mixtures by methods known to those skilled in the art, including chiral high pressure liquid chromatography (HPLC) and the formation and crystallization of chiral salts; or preferred enantiomers can be prepared by asymmetric syntheses. See, for example, Jacques, et al., *Enantiomers, Racemates and Resolutions*, Wiley Interscience, New York (1981); E. L. Eliel and S. H. Wilen, *Stereochemistry of Organic Compounds*, Wiley-Interscience, New York (1994).

A "leaving group or atom" is any group or atom that will, under selected reaction conditions, cleave from the starting material, thus promoting reaction at a specified site. Examples of such groups, unless otherwise specified, include halogen atoms and mesyloxy, p-nitrobenzensulphonyloxy and tosyloxy groups.

"Protecting group" is intended to mean a group that selectively blocks one or more reactive sites in a multifunctional compound such that a chemical reaction can be carried out selectively on another unprotected reactive site and the group can then be readily removed after the selective reaction is complete. A variety of protecting groups are disclosed, for example, in T. H. Greene and P. G. M. Wuts, *Protective Groups in Organic Synthesis*, 3$^{rd}$ Ed., John Wiley & Sons, New York (1999).

"Solvate" refers to a compound in physical association with one or more molecules of a pharmaceutically acceptable solvent.

"Substituted" means that the referenced group may have attached one or more additional moieties individually and independently selected from, for example, acyl, alkyl, alkylaryl, cycloalkyl, aralkyl, aryl, carbohydrate, carbonate, heteroaryl, heterocycloalkyl, hydroxy, alkoxy, aryloxy, mercapto, alkylthio, arylthio, cyano, halo, carbonyl, ester, thiocarbonyl, isocyanato, thiocyanato, isothiocyanato, nitro, oxo, perhaloalkyl, perfluoroalkyl, phosphate, silyl, sulfinyl, sulfonyl, sulfonamidyl, sulfoxyl, sulfonate, urea, and amino, including mono- and di-substituted amino groups, and protected derivatives thereof. The substituents themselves may be substituted, for example, a cycloalkyl substituent may itself have a halide substituent at one or more of its ring carbons.

"Sulfanyl" refers to groups that include —S-(optionally substituted alkyl), —S-(optionally substituted aryl), —S-(optionally substituted heteroaryl) and —S-(optionally substituted heterocycloalkyl).

"Sulfinyl" refers to groups that include —S(O)—H, —S(O)-(optionally substituted alkyl), —S(O)-(optionally substituted amino), —S(O)-(optionally substituted aryl), —S(O)-(optionally substituted heteroaryl) and —S(O)-(optionally substituted heterocycloalkyl).

"Sulfonyl" refers to groups that include —S(O$_2$)—H, —S(O$_2$)-(optionally substituted alkyl), —S(O$_2$)-(optionally substituted amino), —S(O$_2$)-(optionally substituted aryl), —S(O$_2$)-(optionally substituted heteroaryl), and —S(O$_2$)-(optionally substituted heterocycloalkyl).

"Sulfonamidyl" or "sulfonamido" refers to a —S(=O)$_2$—NRR radical, where each R is selected independently from the group consisting of hydrogen, alkyl, cycloalkyl, aryl, heteroaryl (bonded through a ring carbon) and heteroalicyclic (bonded through a ring carbon). The R groups in —NRR of the —S(=O)$_2$—NRR radical may be taken together with the nitrogen to which it is attached to form a 4-, 5-, 6- or 7-membered ring. A sulfonamido group is optionally substituted by one or more of the substituents described for alkyl, cycloalkyl, aryl, heteroaryl, respectively.

"Sulfoxyl" refers to a —S(=O)$_2$OH radical.

"Sulfonate" refers to a —S(=O)$_2$—OR radical, where R is selected from the group consisting of alkyl, cycloalkyl, aryl, heteroaryl (bonded through a ring carbon) and heteroalicyclic (bonded through a ring carbon). A sulfonate group is optionally substituted on R by one or more of the substituents described for alkyl, cycloalkyl, aryl, heteroaryl, respectively.

Compounds of the invention also include crystalline and amorphous forms of those compounds, including, for example, polymorphs, pseudopolymorphs, solvates, hydrates, unsolvated polymorphs (including anhydrates), conformational polymorphs, and amorphous forms of the compounds, as well as mixtures thereof. "Crystalline form" and "polymorph" are intended to include all crystalline and amorphous forms of the compound, including, for example, polymorphs, pseudopolymorphs, solvates, hydrates, unsolvated polymorphs (including anhydrates), conformational polymorphs, and amorphous forms, as well as mixtures thereof, unless a particular crystalline or amorphous form is referred to.

Compounds of the invention also include antibodies. The terms "antibody" and its plural form "antibodies" refer to whole immunoglobulins and any antigen-binding fragment ("antigen-binding portion") or single chains thereof. An "antibody" further refers to a glycoprotein comprising at least two heavy (H) chains and two light (L) chains interconnected by disulfide bonds, or an antigen-binding portion thereof. Each heavy chain is comprised of a heavy chain variable region (abbreviated herein as V$_H$) and a heavy chain constant region. The heavy chain constant region is comprised of three domains, CH1, CH2 and CH3. Each light chain is comprised of a light chain variable region (abbreviated herein as V$_L$) and a light chain constant region. The light chain constant region is comprised of one domain, C$_L$. The V$_H$ and V$_L$ regions of an antibody may be further subdivided into regions of hypervariability, which are referred to as complementarity determining regions (CDR) or hypervariable regions (HVR), and which can be interspersed with regions that are more conserved, termed framework regions (FR). Each V$_H$ and V$_L$ is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen epitope or epitopes. The constant regions of the antibodies may mediate the binding of the immunoglobulin to host tissues or factors, including various cells of the immune system (e.g., effector cells) and the first component (Clq) of the classical complement system.

The terms "monoclonal antibody," "mAb," "monoclonal antibody composition," or their plural forms refer to a preparation of antibody molecules of single molecular composition. A monoclonal antibody composition displays a single binding specificity and affinity for a particular epitope. Monoclonal antibodies specific to CD20 can be made using knowledge and skill in the art of injecting test subjects with CD20 antigen and then isolating hybridomas expressing antibodies having the desired sequence or functional characteristics. DNA encoding the monoclonal antibodies is readily isolated and sequenced using conventional procedures (e.g., by using oligonucleotide probes that are capable of binding specifically to genes encoding the heavy and light chains of the monoclonal antibodies). The hybridoma cells serve as a preferred source of such DNA. Once isolated, the DNA may be placed into expression vectors, which are then transfected into host cells such as $E.$ $coli$ cells, simian COS cells, Chinese hamster ovary (CHO) cells, or myeloma cells that do not otherwise produce immunoglobulin protein, to obtain the synthesis of monoclonal antibodies in the recombinant host cells. Recombinant production of antibodies will be described in more detail below.

The terms "antigen-binding portion" or "antigen-binding fragment" of an antibody (or simply "antibody portion"), as used herein, refers to one or more fragments of an antibody that retain the ability to specifically bind to an antigen such as CD20. It has been shown that the antigen-binding function of an antibody can be performed by fragments of a full-length antibody. Examples of binding fragments encompassed within the term "antigen-binding portion" of an antibody include (i) a Fab fragment, a monovalent fragment consisting of the $V_L$, $V_H$, $C_L$ and CH1 domains; (ii) a F(ab')$_2$ fragment, a bivalent fragment comprising two Fab fragments linked by a disulfide bridge at the hinge region; (iii) a Fd fragment consisting of the $V_H$ and CH1 domains; (iv) a Fv fragment consisting of the $V_L$ and $V_H$ domains of a single arm of an antibody, (v) a domain antibody (dAb) fragment (Ward et al., $Nature,$ 1989, 341, 544-546), which may consist of a $V_H$ or a $V_L$ domain; and (vi) an isolated complementarity determining region (CDR). Furthermore, although the two domains of the Fv fragment, $V_L$ and $V_H$, are coded for by separate genes, they can be joined, using recombinant methods, by a synthetic linker that enables them to be made as a single protein chain in which the $V_L$ and $V_H$ regions pair to form monovalent molecules known as single chain Fv (scFv); see, for example, Bird et al., $Science$ 1988, 242, 423-426; and Huston et al., $Proc. Natl. Acad. Sci. USA$ 1988, 85, 5879-5883). Such scFv chain antibodies are also intended to be encompassed within the terms "antigen-binding portion" or "antigen-binding fragment" of an antibody. These antibody fragments are obtained using conventional techniques known to those with skill in the art, and the fragments are screened for utility in the same manner as are intact antibodies.

The term "human antibody," as used herein, is intended to include antibodies having variable regions in which both the framework and CDR regions are derived from human germline immunoglobulin sequences. Furthermore, if the antibody contains a constant region, the constant region also is derived from human germline immunoglobulin sequences. The human antibodies of the invention may include amino acid residues not encoded by human germline immunoglobulin sequences (e.g., mutations introduced by random or site-specific mutagenesis in vitro or by somatic mutation in vivo). The term "human antibody", as used herein, is not intended to include antibodies in which CDR sequences derived from the germline of another mammalian species, such as a mouse, have been grafted onto human framework sequences.

The term "human monoclonal antibody" refers to antibodies displaying a single binding specificity which have variable regions in which both the framework and CDR regions are derived from human germline immunoglobulin sequences. In one embodiment, the human monoclonal antibodies are produced by a hybridoma which includes a B cell obtained from a transgenic nonhuman animal, e.g., a transgenic mouse, having a genome comprising a human heavy chain transgene and a light chain transgene fused to an immortalized cell.

The term "recombinant human antibody", as used herein, includes all human antibodies that are prepared, expressed, created or isolated by recombinant means, such as (a) antibodies isolated from an animal (e.g., a mouse) that is transgenic or transchromosomal for human immunoglobulin genes or a hybridoma prepared therefrom (described further below), (b) antibodies isolated from a host cell transformed to express the human antibody, e.g., from a transfectoma, (c) antibodies isolated from a recombinant, combinatorial human antibody library, and (d) antibodies prepared, expressed, created or isolated by any other means that involve splicing of human immunoglobulin gene sequences to other DNA sequences. Such recombinant human antibodies have variable regions in which the framework and CDR regions are derived from human germline immunoglobulin sequences. In certain embodiments, however, such recombinant human antibodies can be subjected to in vitro mutagenesis (or, when an animal transgenic for human Ig sequences is used, in vivo somatic mutagenesis) and thus the amino acid sequences of the $V_H$ and $V_L$ regions of the recombinant antibodies are sequences that, while derived from and related to human germline $V_H$ and $V_L$ sequences, may not naturally exist within the human antibody germline repertoire in vivo.

As used herein, "isotype" refers to the antibody class (e.g., IgM or IgG1) that is encoded by the heavy chain constant region genes.

The phrases "an antibody recognizing an antigen" and "an antibody specific for an antigen" are used interchangeably herein with the term "an antibody which binds specifically to an antigen."

The term "human antibody derivatives" refers to any modified form of the human antibody, e.g., a conjugate of the antibody and another agent or antibody. The term "conjugate" or "immunoconjugate" refers to an antibody, or a fragment thereof, conjugated to a therapeutic moiety, such as a bacterial toxin, a cytotoxic drug or a radionuclide-containing toxin. Toxic moieties can be conjugated to antibodies of the invention using methods available in the art.

The terms "humanized antibody," "humanized antibodies," and "humanized" are intended to refer to antibodies in which CDR sequences derived from the germline of another mammalian species, such as a mouse, have been grafted onto human framework sequences. Additional framework region modifications may be made within the human framework sequences. Humanized forms of non-human (for example, murine) antibodies are chimeric antibodies that contain minimal sequence derived from non-human immunoglobulin. For the most part, humanized antibodies are human immunoglobulins (recipient antibody) in which residues from a hypervariable region of the recipient are replaced by residues from a 15 hypervariable region of a non-human species (donor antibody) such as mouse, rat, rabbit or nonhuman primate having the desired specificity, affinity, and capacity. In some instances, Fv framework region (FR) residues of the human immunoglobulin are replaced by corresponding non-human residues. Furthermore, humanized antibodies may comprise residues that are not found in the recipient antibody or in the donor antibody.

These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FR regions are those of a human immunoglobulin sequence. The humanized antibody optionally also will comprise at least a portion of an immunoglobulin constant region (Fc), typically that of a human immunoglobulin. For further details, see Jones et al., *Nature* 1986, 321, 522-525; Riechmann et al., *Nature* 1988, 332, 323-329; and Presta, *Curr. Op. Struct. Biol.* 1992, 2, 593-596.

The term "chimeric antibody" is intended to refer to antibodies in which the variable region sequences are derived from one species and the constant region sequences are derived from another species, such as an antibody in which the variable region sequences are derived from a mouse antibody and the constant region sequences are derived from a human antibody.

A "diabody" is a small antibody fragment with two antigen-binding sites. The fragment comprises a heavy chain variable domain ($V_H$) connected to a light chain variable domain ($V_L$) in the same polypeptide chain ($V_H$-$V_L$ or $V_L$-$V_H$). By using a linker that is too short to allow pairing between the two domains on the same chain, the domains are forced to pair with the complementary domains of another chain and create two antigen-binding sites. Diabodies are described more fully in, e.g., European Patent No. EP 404,097, International Patent Publication No. WO 93/11161; and Bolliger et al., *Proc. Natl. Acad. Sci. USA* 1993, 90, 6444-6448.

The term "glycosylation" refers to a modified derivative of an antibody. An aglycoslated antibody lacks glycosylation. Glycosylation can be altered to, for example, increase the affinity of the antibody for antigen. Such carbohydrate modifications can be accomplished by, for example, altering one or more sites of glycosylation within the antibody sequence. For example, one or more amino acid substitutions can be made that result in elimination of one or more variable region framework glycosylation sites to thereby eliminate glycosylation at that site. Aglycosylation may increase the affinity of the antibody for antigen, as described in U.S. Pat. Nos. 5,714,350 and 6,350,861. Additionally or alternatively, an antibody can be made that has an altered type of glycosylation, such as a hypofucosylated antibody having reduced amounts of fucosyl residues or an antibody having increased bisecting GlcNac structures. Such altered glycosylation patterns have been demonstrated to increase the ability of antibodies. Such carbohydrate modifications can be accomplished by, for example, expressing the antibody in a host cell with altered glycosylation machinery. Cells with altered glycosylation machinery have been described in the art and can be used as host cells in which to express recombinant antibodies of the invention to thereby produce an antibody with altered glycosylation. For example, the cell lines Ms704, Ms705, and Ms709 lack the fucosyltransferase gene, FUT8 (alpha (1,6) fucosyltransferase), such that antibodies expressed in the Ms704, Ms705, and Ms709 cell lines lack fucose on their carbohydrates. The Ms704, Ms705, and Ms709 FUT8-/- cell lines were created by the targeted disruption of the FUT8 gene in CHO/DG44 cells using two replacement vectors (see e.g. U.S. Patent Publication No. 2004/0110704 or Yamane-Ohnuki, et al., *Biotechnol. Bioeng.*, 2004, 87, 614-622). As another example, European Patent No. EP 1,176,195 describes a cell line with a functionally disrupted FUT8 gene, which encodes a fucosyl transferase, such that antibodies expressed in such a cell line exhibit hypofucosylation by reducing or eliminating the alpha 1,6 bond-related enzyme, and also describes cell lines which have a low enzyme activity for adding fucose to the N-acetylglucosamine that binds to the Fc region of the antibody or does not have the enzyme activity, for example the rat myeloma cell line YB2/0 (ATCC CRL 1662). International Patent Publication WO 03/035835 describes a variant CHO cell line, Lec 13 cells, with reduced ability to attach fucose to Asn(297)-linked carbohydrates, also resulting in hypofucosylation of antibodies expressed in that host cell (see also Shields, et al., *J. Biol. Chem.* 2002, 277, 26733-26740. International Patent Publication WO 99/54342 describes cell lines engineered to express glycoprotein-modifying glycosyl transferases (e.g., beta(1,4)-N-acetylglucosaminyltransferase III (GnTIII)) such that antibodies expressed in the engineered cell lines exhibit increased bisecting GlcNac structures which results in increased ADCC activity of the antibodies (see also Umana, et al., *Nat. Biotech.* 1999, 17, 176-180). Alternatively, the fucose residues of the antibody may be cleaved off using a fucosidase enzyme. For example, the fucosidase alpha-L-fucosidase removes fucosyl residues from antibodies as described in Tarentino, et al., *Biochem.* 1975, 14, 5516-5523.

"Pegylation" refers to a modified antibody, or a fragment thereof, that typically is reacted with polyethylene glycol (PEG), such as a reactive ester or aldehyde derivative of PEG, under conditions in which one or more PEG groups become attached to the antibody or antibody fragment. Pegylation may, for example, increase the biological (e.g., serum) half life of the antibody. Preferably, the pegylation is carried out via an acylation reaction or an alkylation reaction with a reactive PEG molecule (or an analogous reactive water-soluble polymer). As used herein, the term "polyethylene glycol" is intended to encompass any of the forms of PEG that have been used to derivatize other proteins, such as mono ($C_1$-$C_{10}$) alkoxy- or aryloxy-polyethylene glycol or polyethylene glycol-maleimide. The antibody to be pegylated may be an aglycosylated antibody. Methods for pegylation are known in the art and can be applied to the antibodies of the invention. See, for example, European Patent Nos. EP 0154316 and EP 0401384.

As used herein, an antibody that "specifically binds to human CD20" is intended to refer to an antibody that binds to human CD20 with a $K_D$ of $1 \times 10^{-7}$ M or less, more preferably $5 \times 10^{-8}$ M or less, more preferably $1 \times 10^{-8}$ M or less, more preferably $5 \times 10^{-9}$ M or less.

The term "radioisotope-labeled complex" refers to both non-covalent and covalent attachment of a radioactive isotope, such as $^{90}Y$, $^{111}In$, or $^{131}I$, to an antibody.

The term "biosimilar" means a biological product that is highly similar to a U.S. licensed reference biological product notwithstanding minor differences in clinically inactive components, and for which there are no clinically meaningful differences between the biological product and the reference product in terms of the safety, purity, and potency of the product. Furthermore, a similar biological or "biosimilar" medicine is a biological medicine that is similar to another biological medicine that has already been authorized for use by the European Medicines Agency. The term "biosimilar" is also used synonymously by other national and regional regulatory agencies. Biological products or biological medicines are medicines that are made by or derived from a biological source, such as a bacterium or yeast. They can consist of relatively small molecules such as human insulin or erythropoietin, or complex molecules such as monoclonal antibodies. For example, if the reference anti-CD20 monoclonal antibody is rituximab, an anti-CD20 biosimilar monoclonal antibody approved by drug regulatory authorities with reference to rituximab is a "biosimilar to" rituximab or is a "biosimilar thereof" rituximab.

BTK Inhibitors

In an embodiment, the BTK inhibitor is a compound of Formula (I):

Formula (I)

or a pharmaceutically acceptable salt thereof,
wherein:
X is CH, N, O or S;
Y is C($R_6$), N, O or S;
Z is CH, N or bond;
A is CH or N;
$B_1$ is N or C($R_7$);
$B_2$ is N or C($R_8$);
$B_3$ is N or C($R_9$);
$B_4$ is N or C($R_{10}$);
$R_1$ is $R_{11}$C(=O), $R_{12}$S(=O), $R_{13}$S(=O)$_2$ or (C$_{1-6}$)alkyl optionally substituted with $R_{14}$;
$R^2$ is H, (C$_{1-3}$)alkyl or (C$_{3-7}$)cycloalkyl;
$R^3$ is H, (C$_{1-6}$)alkyl or (C$_{3-7}$)cycloalkyl); or
$R^2$ and $R^3$ form, together with the N and C atom they are attached to, a (C$_{3-7}$)heterocycloalkyl optionally substituted with one or more fluorine, hydroxyl, (C$_{1-3}$)alkyl, (C$_{1-3}$)alkoxy or oxo;
$R_4$ is H or (C$_{1-3}$)alkyl;
$R_5$ is H, halogen, cyano, (C$_{1-4}$)alkyl, (C$_{1-3}$)alkoxy, (C$_{3-6}$)cycloalkyl, any alkyl group of which is optionally substituted with one or more halogen; or $R_5$ is (C$_{6-10}$)aryl or (C$_{2-6}$)heterocycloalkyl;
$R_6$ is H or (C$_{1-3}$)alkyl; or
$R_5$ and $R^6$ together may form a (C$_{3-7}$)cycloalkenyl or (C$_{2-6}$)heterocycloalkenyl, each optionally substituted with (C$_{1-3}$)alkyl or one or more halogens;
$R_7$ is H, halogen, CF$_3$, (C$_{1-3}$)alkyl or (C$_{1-3}$)alkoxy;
$R_8$ is H, halogen, CF$_3$, (C$_{1-3}$)alkyl or (C$_{1-3}$)alkoxy; or
$R_7$ and $R_8$ together with the carbon atoms they are attached to, form (C$_{6-10}$)aryl or (C$_{1-9}$)heteroaryl;
$R_9$ is H, halogen, (C$_{1-3}$)alkyl or (C$_{1-3}$)alkoxy;
$R_{10}$ is H, halogen, (C$_{1-3}$)alkyl or (C$_{1-3}$)alkoxy;
$R_{11}$ is independently selected from the group consisting of (C$_{1-6}$)alkyl, (C$_{2-6}$)alkenyl and (C$_{2-6}$)alkynyl, where each alkyl, alkenyl or alkynyl is optionally substituted with one or more substituents selected from the group consisting of hydroxyl, (C$_{1-4}$)alkyl, (C$_{3-7}$)cycloalkyl, [(C$_{1-4}$)alkyl]amino, di[(C$_{1-4}$)alkyl]amino, (C$_{1-3}$)alkoxy, (C$_{3-7}$)cycloalkoxy, (C$_{6-10}$)aryl and (C$_{3-7}$)heterocycloalkyl; or $R_{11}$ is (C$_{1-3}$)alkyl-C(O)—S—(C$_{1-3}$)alkyl; or
$R_{11}$ is (C$_{1-5}$)heteroaryl optionally substituted with one or more substituents selected from the group consisting of halogen or cyano;
$R_{12}$ and $R_{13}$ are independently selected from the group consisting of (C$_{2-6}$)alkenyl or (C$_{2-6}$)alkynyl, both optionally substituted with one or more substituents selected from the group consisting of hydroxyl, (C$_{1-4}$)alkyl, (C$_{3-7}$)cycloalkyl, [(C$_{1-4}$)alkyl]amino, di[(C$_{1-4}$)alkyl]amino, (C$_{1-3}$)alkoxy, (C$_{3-7}$)cycloalkoxy, (C$_{6-10}$)aryl and (C$_{3-7}$)heterocycloalkyl; or a (C$_{1-5}$)heteroaryl optionally substituted with one or more substituents selected from the group consisting of halogen and cyano; and
$R_{14}$ is independently selected from the group consisting of halogen, cyano, (C$_{2-6}$)alkenyl and (C$_{2-6}$)alkynyl, both optionally substituted with one or more substituents selected from the group consisting of hydroxyl, (C$_{1-4}$)alkyl, (C$_{3-7}$)cycloalkyl, (C$_{1-4}$)alkylamino, di[(C$_{1-4}$)alkyl]amino, (C$_{1-3}$)alkoxy, (C$_{3-7}$)cycloalkoxy, (C$_{6-10}$)aryl, (C$_{1-5}$)heteroaryl and (C$_{3-7}$)heterocycloalkyl;
with the proviso that:
0 to 2 atoms of X, Y, Z can simultaneously be a heteroatom;
when one atom selected from X, Y is O or S, then Z is a bond and the other atom selected from X, Y can not be O or S;
when Z is C or N then Y is C($R_6$) or N and X is C or N;
0 to 2 atoms of $B_1$, $B_2$, $B_3$, and $B_4$ are N;
with the terms used having the following meanings:
(C$_{1-2}$)alkyl means an alkyl group having 1 to 2 carbon atoms, being methyl or ethyl,
(C$_{1-3}$)alkyl means a branched or unbranched alkyl group having 1-3 carbon atoms, being methyl, ethyl, propyl or isopropyl;
(C$_{1-4}$)alkyl means a branched or unbranched alkyl group having 1-4 carbon atoms, being methyl, ethyl, propyl, isopropyl, butyl, isobutyl, sec-butyl and tert-butyl, (C$_{1-3}$) alkyl groups being preferred;
(C$_{1-5}$)alkyl means a branched or unbranched alkyl group having 1-5 carbon atoms, for example methyl, ethyl, propyl, isopropyl, butyl, isobutyl, sec-butyl, tert-butyl, pentyl and isopentyl, (C$_{1-4}$)alkyl groups being preferred.
(C$_{1-6}$)Alkyl means a branched or unbranched alkyl group having 1-6 carbon atoms, for example methyl, ethyl, propyl, isopropyl, butyl, tert-butyl, n-pentyl and n-hexyl. (C$_{1-5}$)alkyl groups are preferred, (C$_{1-4}$)alkyl being most preferred;
(C$_{1-2}$)alkoxy means an alkoxy group having 1-2 carbon atoms, the alkyl moiety having the same meaning as previously defined;
(C$_{1-3}$)alkoxy means an alkoxy group having 1-3 carbon atoms, the alkyl moiety having the same meaning as previously defined. (C$_{1-2}$)alkoxy groups are preferred;
(C$_{1-4}$)alkoxy means an alkoxy group having 1-4 carbon atoms, the alkyl moiety having the same meaning as previously defined. (C$_{1-3}$)alkoxy groups are preferred, (C$_{1-2}$)alkoxy groups being most preferred;
(C$_{2-4}$)alkenyl means a branched or unbranched alkenyl group having 2-4 carbon atoms, such as ethenyl, 2-propenyl, isobutenyl or 2-butenyl;
(C$_{2-6}$)alkenyl means a branched or unbranched alkenyl group having 2-6 carbon atoms, such as ethenyl, 2-butenyl, and n-pentenyl, (C$_{2-4}$)alkenyl groups being most preferred;

($C_{2-4}$)alkynyl means a branched or unbranched alkynyl group having 2-4 carbon atoms, such as ethynyl, 2-propynyl or 2-butynyl;

($C_{2-6}$)alkynyl means a branched or unbranched alkynyl group having 2-6 carbon atoms, such as ethynyl, propynyl, n-butynyl, n-pentynyl, isopentynyl, isohexynyl or n-hexynyl. ($C_{2-4}$)alkynyl groups are preferred; ($C_{3-6}$)cycloalkyl means a cycloalkyl group having 3-6 carbon atoms, being cyclopropyl, cyclobutyl, cyclopentyl or cyclohexyl;

($C_{3-7}$)cycloalkyl means a cycloalkyl group having 3-7 carbon atoms, being cyclopropyl, cyclobutyl, cyclopentyl, cyclohexyl or cycloheptyl;

($C_{2-6}$)heterocycloalkyl means a heterocycloalkyl group having 2-6 carbon atoms, preferably 3-5 carbon atoms, and one or two heteroatoms selected from N, O and/or S, which may be attached via a heteroatom if feasible, or a carbon atom; preferred heteroatoms are N or O; also preferred are piperidine, morpholine, pyrrolidine and piperazine; with the most preferred ($C_{2-6}$)heterocycloalkyl being pyrrolidine; the heterocycloalkyl group may be attached via a heteroatom if feasible;

($C_{3-7}$)heterocycloalkyl means a heterocycloalkyl group having 3-7 carbon atoms, preferably 3-5 carbon atoms, and one or two heteroatoms selected from N, O and/or S. Preferred heteroatoms are N or O; preferred ($C_{3-7}$) heterocycloalkyl groups are azetidinyl, pyrrolidinyl, piperidinyl, homopiperidinyl or morpholinyl; more preferred ($C_{3-7}$)heterocycloalkyl groups are piperidine, morpholine and pyrrolidine; and the heterocycloalkyl group may be attached via a heteroatom if feasible;

($C_{3-7}$)cycloalkoxy means a cycloalkyl group having 3-7 carbon atoms, with the same meaning as previously defined, attached via a ring carbon atom to an exocyclic oxygen atom;

($C_{6-10}$)aryl means an aromatic hydrocarbon group having 6-10 carbon atoms, such as phenyl, naphthyl, tetrahydronaphthyl or indenyl; the preferred ($C_{6-10}$)aryl group is phenyl;

($C_{1-5}$)heteroaryl means a substituted or unsubstituted aromatic group having 1-5 carbon atoms and 1-4 heteroatoms selected from N, O and/or S; the ($C_{1-5}$)heteroaryl may optionally be substituted; preferred ($C_{1-5}$)heteroaryl groups are tetrazolyl, imidazolyl, thiadiazolyl, pyridyl, pyrimidyl, triazinyl, thienyl or furyl, a more preferred ($C_{1-5}$)heteroaryl is pyrimidyl;

($C_{1-9}$)heteroaryl means a substituted or unsubstituted aromatic group having 1-9 carbon atoms and 1-4 heteroatoms selected from N, O and/or S; the ($C_{1-9}$)heteroaryl may optionally be substituted; preferred ($C_{1-9}$)heteroaryl groups are quinoline, isoquinoline and indole;

[($C_{1-4}$)alkyl]amino means an amino group, monosubstituted with an alkyl group containing 1-4 carbon atoms having the same meaning as previously defined; preferred [($C_{1-4}$)alkyl]amino group is methylamino;

di[($C_{1-4}$)alkyl]amino means an amino group, disubstituted with alkyl group(s), each containing 1-4 carbon atoms and having the same meaning as previously defined; preferred di[($C_{1-4}$)alkyl]amino group is dimethylamino;

halogen means fluorine, chlorine, bromine or iodine;

($C_{1-3}$)alkyl-C(O)—S—($C_{1-3}$)alkyl means an alkyl-carbonyl-thio-alkyl group, each of the alkyl groups having 1 to 3 carbon atoms with the same meaning as previously defined;

($C_{3-7}$)cycloalkenyl means a cycloalkenyl group having 3-7 carbon atoms, preferably 5-7 carbon atoms; preferred ($C_{3-7}$)cycloalkenyl groups are cyclopentenyl or cyclohexenyl; cyclohexenyl groups are most preferred;

($C_{2-6}$)heterocycloalkenyl means a heterocycloalkenyl group having 2-6 carbon atoms, preferably 3-5 carbon atoms; and 1 heteroatom selected from N, O and/or S; preferred ($C_{2-6}$)heterocycloalkenyl groups are oxycyclohexenyl and azacyclohexenyl group.

In the above definitions with multifunctional groups, the attachment point is at the last group.

When, in the definition of a substituent, is indicated that "all of the alkyl groups" of said substituent are optionally substituted, this also includes the alkyl moiety of an alkoxy group.

A circle in a ring of Formula (I) indicates that the ring is aromatic.

Depending on the ring formed, the nitrogen, if present in X or Y, may carry a hydrogen.

The term "substituted" means that one or more hydrogens on the designated atom/atoms is/are replaced with a selection from the indicated group, provided that the designated atom's normal valency under the existing circumstances is not exceeded, and that the substitution results in a stable compound. Combinations of substituents and/or variables are permissible only if such combinations result in stable compounds. "Stable compound" or "stable structure" is defined as a compound or structure that is sufficiently robust to survive isolation to a useful degree of purity from a reaction mixture, and formulation into a drug product containing an efficacious active pharmaceutical ingredient.

The term "optionally substituted" means optional substitution with the specified groups, radicals or moieties.

In an embodiment of Formula (I), $B_1$ is $C(R_7)$; $B_2$ is $C(R_8)$; $B_3$ is $C(R_9)$; $B_4$ is $C(R_{10})$; $R_7$, $R_9$, and $R_{10}$ are each H; and $R_8$ is hydrogen or methyl.

In an embodiment of Formula (I), the ring containing X, Y and Z is selected from the group consisting of pyridyl, pyrimidyl, pyridazyl, triazinyl, thiazolyl, oxazolyl and isoxazolyl.

In an embodiment of Formula (I), the ring containing X, Y and Z is selected from the group consisting of pyridyl, pyrimidyl and pyridazyl.

In an embodiment of Formula (I), the ring containing X, Y and Z is selected from the group consisting of pyridyl and pyrimidyl.

In an embodiment of Formula (I), the ring containing X, Y and Z is pyridyl.

In an embodiment of Formula (I), $R_5$ is selected from the group consisting of hydrogen, fluorine, methyl, methoxy and trifluoromethyl.

In an embodiment of Formula (I), $R_5$ is hydrogen.

In an embodiment of Formula (I), $R_2$ and $R_3$ together form a heterocycloalkyl ring selected from the group consisting of azetidinyl, pyrrolidinyl, piperidinyl, homopiperidinyl and morpholinyl, optionally substituted with one or more of fluoro, hydroxyl, ($C_{1-3}$)alkyl and ($C_{1-3}$)alkoxy.

In an embodiment of Formula (I), $R_2$ and $R_3$ together form a heterocycloalkyl ring selected from the group consisting of azetidinyl, pyrrolidinyl and piperidinyl.

In an embodiment of Formula (I), $R_2$ and $R_3$ together form a pyrrolidinyl ring.

In an embodiment of Formula (I), $R_1$ is independently selected from the group consisting of ($C_{1-6}$)alkyl, ($C_{2-6}$) alkenyl or ($C_{2-6}$)alkynyl, each optionally substituted with one or more substituents selected from the group consisting of hydroxyl, ($C_{1-4}$)alkyl, ($C_{3-7}$)cycloalkyl, [($C_{1-4}$)alkyl]

amino, di[($C_{1-4}$)alkyl] amino, ($C_{1-3}$)alkoxy, ($C_{3-7}$)cycloalkoxy, ($C_{6-10}$)aryl and ($C_{3-7}$)heterocycloalkyl.

In an embodiment of Formula (I), $B_1$, $B_2$, $B_3$ and $B_4$ are CH; X is N; Y and Z are CH; $R_5$ is $CH_3$; A is N; $R_2$, $R_3$ and $R_4$ are H; and $R_1$ is CO—$CH_3$.

In an embodiment of Formula (I), $B_1$, $B_2$, $B_3$ and $B_4$ are CH; X and Y are N; Z is CH; $R_5$ is $CH_3$; A is N; $R_2$, $R_3$ and $R_4$ are H; and $R_1$ is CO—$CH_3$.

In an embodiment of Formula (I), $B_1$, $B_2$, $B_3$ and $B_4$ are CH; X and Y are N; Z is CH; $R_5$ is $CH_3$; A is CH; $R_2$ and $R_3$ together form a piperidinyl ring; $R^4$ is H; and $R_1$ is CO-ethenyl.

In an embodiment of Formula (I), $B_1$, $B_2$, $B_3$ and $B_4$ are CH; X, Y and Z are CH; $R_5$ is H; A is CH; $R_2$ and $R_3$ together form a pyrrolidinyl ring; $R^4$ is H; and $R_1$ is CO-propynyl.

In an embodiment of Formula (I), $B_1$, $B_2$, $B_3$ and $B_4$ are CH; X, Y and Z are CH; $R_5$ is $CH_3$; A is CH; $R_2$ and $R_3$ together form a piperidinyl ring; $R^4$ is H; and $R_1$ is CO-propynyl.

In an embodiment of Formula (I), $B_1$, $B_2$, $B_3$ and $B_4$ are CH; X and Y are N; Z is CH; $R_5$ is H; A is CH; $R_2$ and $R_3$ together form a morpholinyl ring; $R^4$ is H; and $R_1$ is CO-ethenyl.

In an embodiment of Formula (I), $B_1$, $B_2$, $B_3$ and $B_4$ are CH; X and Y are N; Z is CH; $R_5$ is $CH_3$; A is CH; $R_2$ and $R_3$ together form a morpholinyl ring; $R^4$ is H; and $R_1$ is CO-propynyl.

In a preferred embodiment, the BTK inhibitor is a compound of Formula (II):

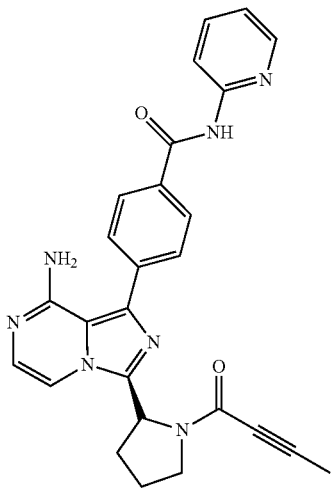

Formula (II)

or a pharmaceutically acceptable salt, solvate, hydrate, cocrystal, or prodrug thereof. The compound of Formula (II) is also known as (S)-4-(8-amino-3-(1-(but-2-ynoyl)pyrrolidin-2-yl)imidazo[1,5-a]pyrazin-1-yl)-N-(pyridin-2-yl)benzamide. In an embodiment, the BTK inhibitor is (S)-4-(8-amino-3-(1-(but-2-ynoyl)pyrrolidin-2-yl)imidazo[1,5-a]pyrazin-1-yl)-N-(pyridin-2-yl)benzamide or a pharmaceutically acceptable salt, solvate, hydrate, cocrystal, or prodrug thereof. The preparation of this compound is described at Example 6 of U.S. Patent Application Publication No. US 2014/0155385 A1, the disclosure of which is incorporated herein by reference. Briefly, the preparation of Formula (II) can be accomplished by the following procedure. 1-[Bis(dimethylamino)methylene]-1H-1,2,3-triazolo[4,5-b]pyridinium 3-oxide hexafluorophosphate (also known as HATU, N-[(Dimethylamino)-1H-1,2,3-triazolo-[4,5-b]pyridin-1-ylmethylene]-N-methylmethanaminium hexafluorophosphate N-oxide, and O-(7-azabenzotriazol-1-yl)-1,1,3,3-tetramethyluroniumhexafluorophosphate) (18.75 mg, 0.049 mmol) was added to a solution of (S)-4-(8-amino-3-(pyrrolidin-2-yl)imidazo[1,5-a]pyrazin-1-yl)-N-(pyridin-2-yl)benzamide (19.7 mg, 0.049 mmol), triethylamine (20 mg, 0.197 mmol, 0.027 mL) and 2-butynoic acid in dichloromethane (2 mL). The mixture was stirred for 30 minutes at room temperature. The mixture was washed with water dried over magnesium sulfate and concentrated under vacuum. The residue was purified by preparative liquid chromatography. Fractions containing product were collected and reduced to dryness to afford 10.5 mg of Formula (II) (18.0% yield).

Pharmaceutical Compositions

In selected embodiments, the invention provides pharmaceutical compositions for treating lymphoma and leukemia, including CLL and SLL.

The pharmaceutical compositions are typically formulated to provide a therapeutically effective amount of a BTK inhibitor, including the BTK inhibitors of Formula (I) or Formula (II), or a pharmaceutically acceptable salt, ester, prodrug, solvate, hydrate or derivative thereof. Where desired, the pharmaceutical compositions contain a pharmaceutically acceptable salt and/or coordination complex thereof, and one or more pharmaceutically acceptable excipients, carriers, including inert solid diluents and fillers, diluents, including sterile aqueous solution and various organic solvents, permeation enhancers, solubilizers and adjuvants. Where desired, other active ingredients in addition to a BTK inhibitor of Formula (I) or Formula (II) may be mixed into a preparation or both components may be formulated into separate preparations for use in combination separately or at the same time.

In selected embodiments, the concentration of the BTK inhibitors of Formula (I) or Formula (II) provided in the pharmaceutical compositions of the invention is less than, for example, 100%, 90%, 80%, 70%, 60%, 50%, 40%, 30%, 20%, 19%, 18%, 17%, 16%, 15%, 14%, 13%, 12%, 11%, 10%, 9%, 8%, 7%, 6%, 5%, 4%, 3%, 2%, 1%, 0.5%, 0.4%, 0.3%, 0.2%, 0.1%, 0.09%, 0.08%, 0.07%, 0.06%, 0.05%, 0.04%, 0.03%, 0.02%, 0.01%, 0.009%, 0.008%, 0.007%, 0.006%, 0.005%, 0.004%, 0.003%, 0.002%, 0.001%, 0.0009%, 0.0008%, 0.0007%, 0.0006%, 0.0005%, 0.0004%, 0.0003%, 0.0002% or 0.0001% w/w, w/v or v/v.

In selected embodiments, the concentration of the BTK inhibitors of Formula (I) or Formula (II) provided in the pharmaceutical compositions of the invention is independently greater than 90%, 80%, 70%, 60%, 50%, 40%, 30%, 20%, 19.75%, 19.50%, 19.25% 19%, 18.75%, 18.50%, 18.25% 18%, 17.75%, 17.50%, 17.25% 17%, 16.75%, 16.50%, 16.25% 16%, 15.75%, 15.50%, 15.25% 15%, 14.75%, 14.50%, 14.25% 14%, 13.75%, 13.50%, 13.25% 13%, 12.75%, 12.50%, 12.25% 12%, 11.75%, 11.50%, 11.25% 11%, 10.75%, 10.50%, 10.25% 10%, 9.75%, 9.50%, 9.25% 9%, 8.75%, 8.50%, 8.25% 8%, 7.75%, 7.50%, 7.25% 7%, 6.75%, 6.50%, 6.25% 6%, 5.75%, 5.50%, 5.25% 5%, 4.75%, 4.50%, 4.25%, 4%, 3.75%, 3.50%, 3.25%, 3%, 2.75%, 2.50%, 2.25%, 2%, 1.75%, 1.50%, 125%, 1%, 0.5%, 0.4%, 0.3%, 0.2%, 0.1%, 0.09%, 0.08%, 0.07%, 0.06%, 0.05%, 0.04%, 0.03%, 0.02%, 0.01%, 0.009%, 0.008%, 0.007%, 0.006%, 0.005%, 0.004%, 0.003%, 0.002%, 0.001%, 0.0009%, 0.0008%, 0.0007%, 0.0006%, 0.0005%, 0.0004%, 0.0003%, 0.0002% or 0.0001% w/w, w/v, or v/v.

In selected embodiments, the concentration of the BTK inhibitors of Formula (I) or Formula (II) is independently in the range from approximately 0.0001% to approximately 50%, approximately 0.001% to approximately 40%, approximately 0.01% to approximately 30%, approximately 0.02% to approximately 29%, approximately 0.03% to approximately 28%, approximately 0.04% to approximately 27%, approximately 0.05% to approximately 26%, approximately 0.06% to approximately 25%, approximately 0.07% to approximately 24%, approximately 0.08% to approximately 23%, approximately 0.09% to approximately 22%, approximately 0.1% to approximately 21%, approximately 0.2% to approximately 20%, approximately 0.3% to approximately 19%, approximately 0.4% to approximately 18%, approximately 0.5% to approximately 17%, approximately 0.6% to approximately 16%, approximately 0.7% to approximately 15%, approximately 0.8% to approximately 14%, approximately 0.9% to approximately 12% or approximately 1% to approximately 10% w/w, w/v or v/v.

In selected embodiments, the concentration of the BTK inhibitors of Formula (I) or Formula (II) is independently in the range from approximately 0.001% to approximately 10%, approximately 0.01% to approximately 5%, approximately 0.02% to approximately 4.5%, approximately 0.03% to approximately 4%, approximately 0.04% to approximately 3.5%, approximately 0.05% to approximately 3%, approximately 0.06% to approximately 2.5%, approximately 0.07% to approximately 2%, approximately 0.08% to approximately 1.5%, approximately 0.09% to approximately 1%, approximately 0.1% to approximately 0.9% w/w, w/v or v/v.

In selected embodiments, the amount of the BTK inhibitors of Formula (I) or Formula (II) is independently equal to or less than 10 g, 9.5 g, 9.0 g, 8.5 g, 8.0 g, 7.5 g, 7.0 g, 6.5 g, 6.0 g, 5.5 g, 5.0 g, 4.5 g, 4.0 g, 3.5 g, 3.0 g, 2.5 g, 2.0 g, 1.5 g, 1.0 g, 0.95 g, 0.9 g, 0.85 g, 0.8 g, 0.75 g, 0.7 g, 0.65 g, 0.6 g, 0.55 g, 0.5 g, 0.45 g, 0.4 g, 0.35 g, 0.3 g, 0.25 g, 0.2 g, 0.15 g, 0.1 g, 0.09 g, 0.08 g, 0.07 g, 0.06 g, 0.05 g, 0.04 g, 0.03 g, 0.02 g, 0.01 g, 0.009 g, 0.008 g, 0.007 g, 0.006 g, 0.005 g, 0.004 g, 0.003 g, 0.002 g, 0.001 g, 0.0009 g, 0.0008 g, 0.0007 g, 0.0006 g, 0.0005 g, 0.0004 g, 0.0003 g, 0.0002 g or 0.0001 g.

In selected embodiments, the amount of the BTK inhibitors of Formula (I) or Formula (II) is independently more than 0.0001 g, 0.0002 g, 0.0003 g, 0.0004 g, 0.0005 g, 0.0006 g, 0.0007 g, 0.0008 g, 0.0009 g, 0.001 g, 0.0015 g, 0.002 g, 0.0025 g, 0.003 g, 0.0035 g, 0.004 g, 0.0045 g, 0.005 g, 0.0055 g, 0.006 g, 0.0065 g, 0.007 g, 0.0075 g, 0.008 g, 0.0085 g, 0.009 g, 0.0095 g, 0.01 g, 0.015 g, 0.02 g, 0.025 g, 0.03 g, 0.035 g, 0.04 g, 0.045 g, 0.05 g, 0.055 g, 0.06 g, 0.065 g, 0.07 g, 0.075 g, 0.08 g, 0.085 g, 0.09 g, 0.095 g, 0.1 g, 0.15 g, 0.2 g, 0.25 g, 0.3 g, 0.35 g, 0.4 g, 0.45 g, 0.5 g, 0.55 g, 0.6 g, 0.65 g, 0.7 g, 0.75 g, 0.8 g, 0.85 g, 0.9 g, 0.95 g, 1 g, 1.5 g, 2 g, 2.5, 3 g, 3.5, 4 g, 4.5 g, 5 g, 5.5 g, 6 g, 6.5 g, 7 g, 7.5 g, 8 g, 8.5 g, 9 g, 9.5 g or 10 g.

The BTK inhibitors of Formula (I) or Formula (II) are effective over a wide dosage range. For example, in the treatment of adult humans, dosages independently ranging from 0.01 to 1000 mg, from 0.5 to 100 mg, from 1 to 50 mg per day, and from 5 to 40 mg per day are examples of dosages that may be used. The exact dosage will depend upon the route of administration, the form in which the compound is administered, the gender and age of the subject to be treated, the body weight of the subject to be treated, and the preference and experience of the attending physician.

Described below are non-limiting exemplary pharmaceutical compositions and methods for preparing the same.
Pharmaceutical Compositions for Oral Administration In selected embodiments, the invention provides a pharmaceutical composition for oral administration containing a BTK inhibitor of Formula (I) or Formula (II), and a pharmaceutical excipient suitable for oral administration.

In selected embodiments, the invention provides a solid pharmaceutical composition for oral administration containing: (i) an effective amount of a BTK inhibitor of Formula (I) or Formula (II), in combination and (ii) a pharmaceutical excipient suitable for oral administration. In selected embodiments, the composition further contains (iii) an effective amount of at least one additional active ingredient.

In selected embodiments, the pharmaceutical composition may be a liquid pharmaceutical composition suitable for oral consumption. Pharmaceutical compositions of the invention suitable for oral administration can be presented as discrete dosage forms, such as capsules, cachets, or tablets, or liquids or aerosol sprays each containing a predetermined amount of an active ingredient as a powder or in granules, a solution, or a suspension in an aqueous or non-aqueous liquid, an oil-in-water emulsion, or a water-in-oil liquid emulsion. Such dosage forms can be prepared by any of the methods of pharmacy, but all methods include the step of bringing the active ingredient(s) into association with the carrier, which constitutes one or more necessary ingredients. In general, the compositions are prepared by uniformly and intimately admixing the active ingredient(s) with liquid carriers or finely divided solid carriers or both, and then, if necessary, shaping the product into the desired presentation. For example, a tablet can be prepared by compression or molding, optionally with one or more accessory ingredients. Compressed tablets can be prepared by compressing in a suitable machine the active ingredient in a free-flowing form such as powder or granules, optionally mixed with an excipient such as, but not limited to, a binder, a lubricant, an inert diluent, and/or a surface active or dispersing agent. Molded tablets can be made by molding in a suitable machine a mixture of the powdered compound moistened with an inert liquid diluent.

The invention further encompasses anhydrous pharmaceutical compositions and dosage forms since water can facilitate the degradation of some compounds. For example, water may be added (e.g., 5%) in the pharmaceutical arts as a means of simulating long-term storage in order to determine characteristics such as shelf-life or the stability of formulations over time. Anhydrous pharmaceutical compositions and dosage forms of the invention can be prepared using anhydrous or low moisture containing ingredients and low moisture or low humidity conditions. Pharmaceutical compositions and dosage forms of the invention which contain lactose can be made anhydrous if substantial contact with moisture and/or humidity during manufacturing, packaging, and/or storage is expected. An anhydrous pharmaceutical composition may be prepared and stored such that its anhydrous nature is maintained. Accordingly, anhydrous compositions may be packaged using materials known to prevent exposure to water such that they can be included in suitable formulary kits. Examples of suitable packaging include, but are not limited to, hermetically sealed foils, plastic or the like, unit dose containers, blister packs, and strip packs.

The BTK inhibitors of Formula (I) or Formula (II) can be combined in an intimate admixture with a pharmaceutical carrier according to conventional pharmaceutical compounding techniques. The carrier can take a wide variety of forms depending on the form of preparation desired for administration. In preparing the compositions for an oral dosage form, any of the usual pharmaceutical media can be employed as carriers, such as, for example, water, glycols, oils, alcohols, flavoring agents, preservatives, coloring agents, and the like in the case of oral liquid preparations (such as suspensions, solutions, and elixirs) or aerosols; or carriers such as starches, sugars, micro-crystalline cellulose, diluents, granulating agents, lubricants, binders, and disintegrating agents can be used in the case of oral solid preparations, in some embodiments without employing the use of lactose. For example, suitable carriers include powders, capsules, and tablets, with the solid oral preparations. If desired, tablets can be coated by standard aqueous or nonaqueous techniques.

Binders suitable for use in pharmaceutical compositions and dosage forms include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre-gelatinized starch, hydroxypropyl methyl cellulose, microcrystalline cellulose, and mixtures thereof.

Examples of suitable fillers for use in the pharmaceutical compositions and dosage forms disclosed herein include, but are not limited to, talc, calcium carbonate (e.g., granules or powder), microcrystalline cellulose, powdered cellulose, dextrates, kaolin, mannitol, silicic acid, sorbitol, starch, pre-gelatinized starch, and mixtures thereof.

Disintegrants may be used in the compositions of the invention to provide tablets that disintegrate when exposed to an aqueous environment. Too much of a disintegrant may produce tablets which disintegrate in the bottle. Too little may be insufficient for disintegration to occur, thus altering the rate and extent of release of the active ingredients from the dosage form. Thus, a sufficient amount of disintegrant that is neither too little nor too much to detrimentally alter the release of the active ingredient(s) may be used to form the dosage forms of the compounds disclosed herein. The amount of disintegrant used may vary based upon the type of formulation and mode of administration, and may be readily discernible to those of ordinary skill in the art. About 0.5 to about 15 weight percent of disintegrant, or about 1 to about 5 weight percent of disintegrant, may be used in the pharmaceutical composition. Disintegrants that can be used to form pharmaceutical compositions and dosage forms of the invention include, but are not limited to, agar-agar, alginic acid, calcium carbonate, microcrystalline cellulose, croscarmellose sodium, crospovidone, polacrilin potassium, sodium starch glycolate, potato or tapioca starch, other starches, pre-gelatinized starch, other starches, clays, other algins, other celluloses, gums or mixtures thereof.

Lubricants which can be used to form pharmaceutical compositions and dosage forms of the invention include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethylaureate, agar, or mixtures thereof. Additional lubricants include, for example, a syloid silica gel, a coagulated aerosol of synthetic silica, or mixtures thereof. A lubricant can optionally be added, in an amount of less than about 1 weight percent of the pharmaceutical composition.

When aqueous suspensions and/or elixirs are desired for oral administration, the essential active ingredient therein may be combined with various sweetening or flavoring agents, coloring matter or dyes and, if so desired, emulsifying and/or suspending agents, together with such diluents as water, ethanol, propylene glycol, glycerin and various combinations thereof.

The tablets can be uncoated or coated by known techniques to delay disintegration and absorption in the gastrointestinal tract and thereby provide a sustained action over a longer period. For example, a time delay material such as glyceryl monostearate or glyceryl distearate can be employed. Formulations for oral use can also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil.

Surfactants which can be used to form pharmaceutical compositions and dosage forms of the invention include, but are not limited to, hydrophilic surfactants, lipophilic surfactants, and mixtures thereof. That is, a mixture of hydrophilic surfactants may be employed, a mixture of lipophilic surfactants may be employed, or a mixture of at least one hydrophilic surfactant and at least one lipophilic surfactant may be employed.

A suitable hydrophilic surfactant may generally have an HLB value of at least 10, while suitable lipophilic surfactants may generally have an HLB value of or less than about 10. An empirical parameter used to characterize the relative hydrophilicity and hydrophobicity of non-ionic amphiphilic compounds is the hydrophilic-lipophilic balance ("HLB" value). Surfactants with lower HLB values are more lipophilic or hydrophobic, and have greater solubility in oils, while surfactants with higher HLB values are more hydrophilic, and have greater solubility in aqueous solutions. Hydrophilic surfactants are generally considered to be those compounds having an HLB value greater than about 10, as well as anionic, cationic, or zwitterionic compounds for which the HLB scale is not generally applicable. Similarly, lipophilic (i.e., hydrophobic) surfactants are compounds having an HLB value equal to or less than about 10. However, HLB value of a surfactant is merely a rough guide generally used to enable formulation of industrial, pharmaceutical and cosmetic emulsions.

Hydrophilic surfactants may be either ionic or non-ionic. Suitable ionic surfactants include, but are not limited to, alkylammonium salts; fusidic acid salts; fatty acid derivatives of amino acids, oligopeptides, and polypeptides; glyceride derivatives of amino acids, oligopeptides, and polypeptides; lecithins and hydrogenated lecithins; lysolecithins and hydrogenated lysolecithins; phospholipids and derivatives thereof; lysophospholipids and derivatives thereof; carnitine fatty acid ester salts; salts of alkylsulfates; fatty acid salts; sodium docusate; acylactylates; mono- and di-acetylated tartaric acid esters of mono- and di-glycerides; succinylated mono- and di-glycerides; citric acid esters of mono- and di-glycerides; and mixtures thereof.

Within the aforementioned group, ionic surfactants include, by way of example: lecithins, lysolecithin, phospholipids, lysophospholipids and derivatives thereof; carnitine fatty acid ester salts; salts of alkylsulfates; fatty acid salts; sodium docusate; acylactylates; mono- and di-acetylated tartaric acid esters of mono- and di-glycerides; succinylated mono- and di-glycerides; citric acid esters of mono- and di-glycerides; and mixtures thereof.

Ionic surfactants may be the ionized forms of lecithin, lysolecithin, phosphatidylcholine, phosphatidylethanolamine, phosphatidylglycerol, phosphatidic acid, phosphatidylserine, lysophosphatidylcholine, lysophosphatidylethanolamine, lysophosphatidylglycerol, lysophosphatidic acid, lysophosphatidylserine, PEG-phosphatidylethanolamine, PVP-phosphatidylethanolamine, lactylic esters of fatty acids, stearoyl-2-lactylate, stearoyl lactylate, succinylated monoglycerides, mono/diacetylated tartaric acid esters of mono/diglycerides, citric acid esters of mono/diglycerides, cholylsarcosine, caproate, caprylate, caprate, laurate, myristate, palmitate, oleate, ricinoleate, linoleate, linolenate, stearate, lauryl sulfate, teracecyl sulfate, docusate, lauroyl carnitines, palmitoyl carnitines, myristoyl carnitines, and salts and mixtures thereof.

Hydrophilic non-ionic surfactants may include, but not limited to, alkylglucosides; alkylmaltosides; alkylthioglucosides; lauryl macrogolglycerides; polyoxyalkylene alkyl ethers such as polyethylene glycol alkyl ethers; polyoxyalkylene alkylphenols such as polyethylene glycol alkyl phenols; polyoxyalkylene alkyl phenol fatty acid esters such as polyethylene glycol fatty acids monoesters and polyethylene glycol fatty acids diesters; polyethylene glycol glycerol fatty acid esters; polyglycerol fatty acid esters; polyoxyalkylene sorbitan fatty acid esters such as polyethylene glycol sorbitan fatty acid esters; hydrophilic transesterification products of a polyol with at least one member of the group consisting of glycerides, vegetable oils, hydrogenated vegetable oils, fatty acids, and sterols; polyoxyethylene sterols, derivatives, and analogues thereof; polyoxyethylated vitamins and derivatives thereof; polyoxyethylene-polyoxypropylene block copolymers; and mixtures thereof; polyethylene glycol sorbitan fatty acid esters and hydrophilic transesterification products of a polyol with at least one member of the group consisting of triglycerides, vegetable oils, and hydrogenated vegetable oils. The polyol may be glycerol, ethylene glycol, polyethylene glycol, sorbitol, propylene glycol, pentaerythritol, or a saccharide.

Other hydrophilic-non-ionic surfactants include, without limitation, PEG-10 laurate, PEG-12 laurate, PEG-20 laurate, PEG-32 laurate, PEG-32 dilaurate, PEG-12 oleate, PEG-15 oleate, PEG-20 oleate, PEG-20 dioleate, PEG-32 oleate, PEG-200 oleate, PEG-400 oleate, PEG-15 stearate, PEG-32 distearate, PEG-40 stearate, PEG-100 stearate, PEG-20 dilaurate, PEG-25 glyceryl trioleate, PEG-32 dioleate, PEG-20 glyceryl laurate, PEG-30 glyceryl laurate, PEG-20 glyceryl stearate, PEG-20 glyceryl oleate, PEG-30 glyceryl oleate, PEG-30 glyceryl laurate, PEG-40 glyceryl laurate, PEG-40 palm kernel oil, PEG-50 hydrogenated castor oil, PEG-40 castor oil, PEG-35 castor oil, PEG-60 castor oil, PEG-40 hydrogenated castor oil, PEG-60 hydrogenated castor oil, PEG-60 corn oil, PEG-6 caprate/caprylate glycerides, PEG-8 caprate/caprylate glycerides, polyglyceryl-10 laurate, PEG-30 cholesterol, PEG-25 phyto sterol, PEG-30 soya sterol, PEG-20 trioleate, PEG-40 sorbitan oleate, PEG-80 sorbitan laurate, polysorbate 20, polysorbate 80, POE-9 lauryl ether, POE-23 lauryl ether, POE-10 oleyl ether, POE-20 oleyl ether, POE-20 stearyl ether, tocopheryl PEG-100 succinate, PEG-24 cholesterol, polyglyceryl-10 oleate, Tween 40, Tween 60, sucrose monostearate, sucrose monolaurate, sucrose monopalmitate, PEG 10-100 nonyl phenol series, PEG 15-100 octyl phenol series, and poloxamers.

Suitable lipophilic surfactants include, by way of example only: fatty alcohols; glycerol fatty acid esters; acetylated glycerol fatty acid esters; lower alcohol fatty acids esters; propylene glycol fatty acid esters; sorbitan fatty acid esters; polyethylene glycol sorbitan fatty acid esters; sterols and sterol derivatives; polyoxyethylated sterols and sterol derivatives; polyethylene glycol alkyl ethers; sugar esters; sugar ethers; lactic acid derivatives of mono- and di-glycerides; hydrophobic transesterification products of a polyol with at least one member of the group consisting of glycerides, vegetable oils, hydrogenated vegetable oils, fatty acids and sterols; oil-soluble vitamins/vitamin derivatives; and mixtures thereof. Within this group, preferred lipophilic surfactants include glycerol fatty acid esters, propylene glycol fatty acid esters, and mixtures thereof, or are hydrophobic transesterification products of a polyol with at least one member of the group consisting of vegetable oils, hydrogenated vegetable oils, and triglycerides.

In an embodiment, the composition may include a solubilizer to ensure good solubilization and/or dissolution of the compound of the present invention and to minimize precipitation of the compound of the present invention. This can be especially important for compositions for non-oral use, such as for compositions for injection. A solubilizer may also be added to increase the solubility of the hydrophilic drug and/or other components, such as surfactants, or to maintain the composition as a stable or homogeneous solution or dispersion.

Examples of suitable solubilizers include, but are not limited to, the following: alcohols and polyols, such as ethanol, isopropanol, butanol, benzyl alcohol, ethylene glycol, propylene glycol, butanediols and isomers thereof, glycerol, pentaerythritol, sorbitol, mannitol, transcutol, dimethyl isosorbide, polyethylene glycol, polypropylene glycol, polyvinylalcohol, hydroxypropyl methylcellulose and other cellulose derivatives, cyclodextrins and cyclodextrin derivatives; ethers of polyethylene glycols having an average molecular weight of about 200 to about 6000, such as tetrahydrofurfuryl alcohol PEG ether (glycofurol) or methoxy PEG; amides and other nitrogen-containing compounds such as 2-pyrrolidone, 2-piperidone, ε-caprolactam, N-alkylpyrrolidone, N-hydroxyalkylpyrrolidone, N-alkylpiperidone, N-alkylcaprolactam, dimethylacetamide and polyvinylpyrrolidone; esters such as ethyl propionate, tributylcitrate, acetyl triethylcitrate, acetyl tributyl citrate, triethylcitrate, ethyl oleate, ethyl caprylate, ethyl butyrate, triacetin, propylene glycol monoacetate, propylene glycol diacetate, .epsilon.-caprolactone and isomers thereof, S-valerolactone and isomers thereof, β-butyrolactone and isomers thereof; and other solubilizers known in the art, such as dimethyl acetamide, dimethyl isosorbide, N-methyl pyrrolidones, monooctanoin, diethylene glycol monoethyl ether, and water.

Mixtures of solubilizers may also be used. Examples include, but not limited to, triacetin, triethylcitrate, ethyl oleate, ethyl caprylate, dimethylacetamide, N-methylpyrrolidone, N-hydroxyethylpyrrolidone, polyvinylpyrrolidone, hydroxypropyl methylcellulose, hydroxypropyl cyclodextrins, ethanol, polyethylene glycol 200-100, glycofurol, transcutol, propylene glycol, and dimethyl isosorbide. Particularly preferred solubilizers include sorbitol, glycerol, triacetin, ethyl alcohol, PEG-400, glycofurol and propylene glycol.

The amount of solubilizer that can be included is not particularly limited. The amount of a given solubilizer may be limited to a bioacceptable amount, which may be readily determined by one of skill in the art. In some circumstances, it may be advantageous to include amounts of solubilizers far in excess of bioacceptable amounts, for example to maximize the concentration of the drug, with excess solubilizer removed prior to providing the composition to a patient using conventional techniques, such as distillation or evaporation. Thus, if present, the solubilizer can be in a weight ratio of 10%, 25%, 50%, 100%, or up to about 200% by weight, based on the combined weight of the drug, and other excipients. If desired, very small amounts of solubilizer may also be used, such as 5%, 2%, 1% or even less. Typically, the solubilizer may be present in an amount of about 1% to about 100%, more typically about 5% to about 25% by weight.

The composition can further include one or more pharmaceutically acceptable additives and excipients. Such additives and excipients include, without limitation, detackifiers, anti-foaming agents, buffering agents, polymers, antioxidants, preservatives, chelating agents, viscomodulators, tonicifiers, flavorants, colorants, odorants, opacifiers, suspending agents, binders, fillers, plasticizers, lubricants, and mixtures thereof.

In addition, an acid or a base may be incorporated into the composition to facilitate processing, to enhance stability, or for other reasons. Examples of pharmaceutically acceptable bases include amino acids, amino acid esters, ammonium hydroxide, potassium hydroxide, sodium hydroxide, sodium hydrogen carbonate, aluminum hydroxide, calcium carbonate, magnesium hydroxide, magnesium aluminum silicate, synthetic aluminum silicate, synthetic hydrocalcite, magnesium aluminum hydroxide, diisopropylethylamine, ethanolamine, ethylenediamine, triethanolamine, triethylamine, triisopropanolamine, trimethylamine, tris(hydroxymethyl)aminomethane (TRIS) and the like. Also suitable are bases that are salts of a pharmaceutically acceptable acid, such as acetic acid, acrylic acid, adipic acid, alginic acid, alkanesulfonic acid, amino acids, ascorbic acid, benzoic acid, boric acid, butyric acid, carbonic acid, citric acid, fatty acids, formic acid, fumaric acid, gluconic acid, hydroquinosulfonic acid, isoascorbic acid, lactic acid, maleic acid, oxalic acid, para-bromophenylsulfonic acid, propionic acid, p-toluenesulfonic acid, salicylic acid, stearic acid, succinic acid, tannic acid, tartaric acid, thioglycolic acid, toluenesulfonic acid, uric acid, and the like. Salts of polyprotic acids, such as sodium phosphate, disodium hydrogen phosphate, and sodium dihydrogen phosphate can also be used. When the base is a salt, the cation can be any convenient and pharmaceutically acceptable cation, such as ammonium, alkali metals and alkaline earth metals. Examples may include, but are not limited to, sodium, potassium, lithium, magnesium, calcium and ammonium.

Suitable acids are pharmaceutically acceptable organic or inorganic acids. Examples of suitable inorganic acids include hydrochloric acid, hydrobromic acid, hydriodic acid, sulfuric acid, nitric acid, boric acid, phosphoric acid, and the like. Examples of suitable organic acids include acetic acid, acrylic acid, adipic acid, alginic acid, alkanesulfonic acids, amino acids, ascorbic acid, benzoic acid, boric acid, butyric acid, carbonic acid, citric acid, fatty acids, formic acid, fumaric acid, gluconic acid, hydroquinosulfonic acid, isoascorbic acid, lactic acid, maleic acid, methanesulfonic acid, oxalic acid, para-bromophenylsulfonic acid, propionic acid, p-toluenesulfonic acid, salicylic acid, stearic acid, succinic acid, tannic acid, tartaric acid, thioglycolic acid, toluenesulfonic acid and uric acid.

Pharmaceutical Compositions for Injection

In selected embodiments, the invention provides a pharmaceutical composition for injection containing a BTK inhibitor of Formula (I) or Formula (II), and a pharmaceutical excipient suitable for injection. Components and amounts of agents in the compositions are as described herein.

The forms in which the compositions of the present invention may be incorporated for administration by injection include aqueous or oil suspensions, or emulsions, with sesame oil, corn oil, cottonseed oil, or peanut oil, as well as elixirs, mannitol, dextrose, or a sterile aqueous solution, and similar pharmaceutical vehicles.

Aqueous solutions in saline are also conventionally used for injection. Ethanol, glycerol, propylene glycol and liquid polyethylene glycol (and suitable mixtures thereof), cyclodextrin derivatives, and vegetable oils may also be employed. The proper fluidity can be maintained, for example, by the use of a coating, such as lecithin, for the maintenance of the required particle size in the case of dispersion and by the use of surfactants. The prevention of the action of microorganisms can be brought about by various antibacterial and antifungal agents, for example, parabens, chlorobutanol, phenol, sorbic acid and thimerosal.

Sterile injectable solutions are prepared by incorporating a BTK inhibitor of Formula (I) or Formula (II) in the required amounts in the appropriate solvent with various other ingredients as enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, certain desirable methods of preparation are vacuum-drying and freeze-drying techniques which yield a powder of the active ingredient plus any additional desired ingredient from a previously sterile-filtered solution thereof.

Pharmaceutical Compositions for Topical Delivery

In some embodiments, the invention provides a pharmaceutical composition for transdermal delivery containing the BTK inhibitors of Formula (I) or Formula (II) and a pharmaceutical excipient suitable for transdermal delivery.

Compositions of the present invention can be formulated into preparations in solid, semi-solid, or liquid forms suitable for local or topical administration, such as gels, water soluble jellies, creams, lotions, suspensions, foams, powders, slurries, ointments, solutions, oils, pastes, suppositories, sprays, emulsions, saline solutions, dimethylsulfoxide (DMSO)-based solutions. In general, carriers with higher densities are capable of providing an area with a prolonged exposure to the active ingredients. In contrast, a solution formulation may provide more immediate exposure of the active ingredient to the chosen area.

The pharmaceutical compositions also may comprise suitable solid or gel phase carriers or excipients, which are compounds that allow increased penetration of, or assist in the delivery of, therapeutic molecules across the stratum corneum permeability barrier of the skin. There are many of these penetration-enhancing molecules known to those trained in the art of topical formulation. Examples of such carriers and excipients include, but are not limited to, humectants (e.g., urea), glycols (e.g., propylene glycol), alcohols (e.g., ethanol), fatty acids (e.g., oleic acid), surfactants (e.g., isopropyl myristate and sodium lauryl sulfate), pyrrolidones, glycerol monolaurate, sulfoxides, terpenes (e.g., menthol), amines, amides, alkanes, alkanols, water, calcium carbonate, calcium phosphate, various sugars, starches, cellulose derivatives, gelatin, and polymers such as polyethylene glycols.

Another exemplary formulation for use in the methods of the present invention employs transdermal delivery devices ("patches"). Such transdermal patches may be used to provide continuous or discontinuous infusion of the BTK inhibitors of Formula (I) or Formula (II) in controlled amounts, either with or without another active pharmaceutical ingredient.

The construction and use of transdermal patches for the delivery of pharmaceutical agents is well known in the art. See, e.g., U.S. Pat. Nos. 5,023,252; 4,992,445 and 5,001,139. Such patches may be constructed for continuous, pulsatile, or on demand delivery of pharmaceutical agents.

Other Pharmaceutical Compositions

Pharmaceutical compositions may also be prepared from compositions described herein and one or more pharmaceutically acceptable excipients suitable for sublingual, buccal, rectal, intraosseous, intraocular, intranasal, epidural, or intraspinal administration. Preparations for such pharmaceutical compositions are well-known in the art. See, e.g., Anderson, et al. eds., *Handbook of Clinical Drug Data*, Tenth Edition, McGraw-Hill, 2002; and Pratt and Taylor, eds., *Principles of Drug Action*, Third Edition, Churchill Livingston, N.Y., 1990.

Administration of the BTK inhibitors of Formula (I) or Formula (II) or pharmaceutical composition of these compounds can be effected by any method that enables delivery of the compounds to the site of action. These methods include oral routes, intraduodenal routes, parenteral injection (including intravenous, intraarterial, subcutaneous, intramuscular, intravascular, intraperitoneal or infusion), topical (e.g., transdermal application), rectal administration, via local delivery by catheter or stent or through inhalation. The combination of compounds can also be administered intraadiposally or intrathecally.

Exemplary parenteral administration forms include solutions or suspensions of active compound in sterile aqueous solutions, for example, aqueous propylene glycol or dextrose solutions. Such dosage forms can be suitably buffered, if desired.

The invention also provides kits. The kits include the BTK inhibitors of Formula (I) or Formula (II), either alone or in combination in suitable packaging, and written material that can include instructions for use, discussion of clinical studies and listing of side effects. Such kits may also include information, such as scientific literature references, package insert materials, clinical trial results, and/or summaries of these and the like, which indicate or establish the activities and/or advantages of the composition, and/or which describe dosing, administration, side effects, drug interactions, or other information useful to the health care provider. Such information may be based on the results of various studies, for example, studies using experimental animals involving in vivo models and studies based on human clinical trials. The kit may further contain another active pharmaceutical ingredient. Suitable packaging and additional articles for use (e.g., measuring cup for liquid preparations, foil wrapping to minimize exposure to air, and the like) are known in the art and may be included in the kit. Kits described herein can be provided, marketed and/or promoted to health providers, including physicians, nurses, pharmacists, formulary officials, and the like. Kits may also, in selected embodiments, be marketed directly to the consumer. In an embodiment, the invention provides a kit comprising a BTK inhibitor of Formula (I) or Formula (II) for use in the treatment of CLL or SLL, hematological malignancies, or any of the other cancers described herein.

Dosages and Dosing Regimens

The amounts of BTK inhibitors administered will be dependent on the mammal being treated, the severity of the disorder or condition, the rate of administration, the disposition of the compounds and the discretion of the prescribing physician. However, an effective dosage is in the range of about 0.001 to about 100 mg per kg body weight per day, such as about 1 to about 35 mg/kg/day, in single or divided doses. For a 70 kg human, this would amount to about 0.05 to 7 g/day, such as about 0.05 to about 2.5 g/day. In some instances, dosage levels below the lower limit of the aforesaid range may be more than adequate, while in other cases still larger doses may be employed without causing any harmful side effect—e.g., by dividing such larger doses into several small doses for administration throughout the day.

In some embodiments, the BTK inhibitor of Formula (I) or Formula (II) is administered in a single dose. Typically, such administration will be by injection—e.g., intravenous injection, in order to introduce the agents quickly. However, other routes may be used as appropriate. A single dose of a BTK inhibitor of Formula (I) or Formula (II) may also be used for treatment of an acute condition.

In some embodiments, the BTK inhibitor of Formula (I) or Formula (II) is administered in multiple doses. Dosing may be once, twice, three times, four times, five times, six times, or more than six times per day. Dosing may be once a month, once every two weeks, once a week, or once every other day. In other embodiments, a BTK inhibitor of Formula (I) or Formula (II) is administered about once per day to about 6 times per day. In some embodiments a BTK inhibitor of Formula (I) or Formula (II) is administered once daily, while in other embodiments a BTK inhibitor of Formula (I) or Formula (II) is administered twice daily, and in other embodiments a BTK inhibitor of Formula (I) or Formula (II) is administered three times daily.

Administration of the BTK inhibitor of Formula (I) or Formula (II) may continue as long as necessary. In some embodiments, the BTK inhibitor of Formula (I) or Formula (II) is administered for more than 1, 2, 3, 4, 5, 6, 7, 14, or 28 days. In some embodiments, the BTK inhibitor of Formula (I) or Formula (II) is administered for less than 28, 14, 7, 6, 5, 4, 3, 2, or 1 day. In some embodiments, the BTK inhibitor of Formula (I) or Formula (II) is administered chronically on an ongoing basis—e.g., for the treatment of chronic effects. In another embodiment the administration of a BTK inhibitor of Formula (I) or Formula (II) continues for less than about 7 days. In yet another embodiment the administration continues for more than about 6, 10, 14, 28 days, two months, six months, or one year. In some embodiments, continuous dosing is achieved and maintained as long as necessary.

In some embodiments, an effective dosage of a BTK inhibitor of Formula (I) or Formula (II) is in the range of about 1 mg to about 500 mg, about 10 mg to about 300 mg, about 20 mg to about 250 mg, about 25 mg to about 200 mg, about 10 mg to about 200 mg, about 20 mg to about 150 mg, about 30 mg to about 120 mg, about 10 mg to about 90 mg, about 20 mg to about 80 mg, about 30 mg to about 70 mg, about 40 mg to about 60 mg, about 45 mg to about 55 mg, about 48 mg to about 52 mg, about 50 mg to about 150 mg, about 60 mg to about 140 mg, about 70 mg to about 130 mg, about 80 mg to about 120 mg, about 90 mg to about 110 mg, about 95 mg to about 105 mg, about 150 mg to about 250 mg, about 160 mg to about 240 mg, about 170 mg to about 230 mg, about 180 mg to about 220 mg, about 190 mg to about 210 mg, about 195 mg to about 205 mg, or about 198 to about 202 mg. In some embodiments, an effective dosage of a BTK inhibitor of Formula (I) or Formula (II) is about 25 mg, about 50 mg, about 75 mg, about 100 mg, about 125 mg, about 150 mg, about 175 mg, about 200 mg, about 225 mg, about 250 mg, about 275 mg, about 300 mg, about 325 mg, about 350 mg, about 375 mg, about 400 mg, about 425 mg, about 450 mg, about 475 mg, or about 500 mg. In some embodiments, an effective dosage of a BTK inhibitor of Formula (I) or Formula (II) is 25 mg, 50 mg, 75 mg, 100 mg, 125 mg, 150 mg, 175 mg, 200 mg, 225 mg, 250 mg, 275 mg, 300 mg, 325 mg, 350 mg, 375 mg, 400 mg, 425 mg, 450 mg, 475 mg, or 500 mg.

In some embodiments, an effective dosage of a BTK inhibitor of Formula (I) or Formula (II) is in the range of about 0.01 mg/kg to about 4.3 mg/kg, about 0.15 mg/kg to about 3.6 mg/kg, about 0.3 mg/kg to about 3.2 mg/kg, about 0.35 mg/kg to about 2.85 mg/kg, about 0.15 mg/kg to about 2.85 mg/kg, about 0.3 mg to about 2.15 mg/kg, about 0.45 mg/kg to about 1.7 mg/kg, about 0.15 mg/kg to about 1.3 mg/kg, about 0.3 mg/kg to about 1.15 mg/kg, about 0.45 mg/kg to about 1 mg/kg, about 0.55 mg/kg to about 0.85 mg/kg, about 0.65 mg/kg to about 0.8 mg/kg, about 0.7 mg/kg to about 0.75 mg/kg, about 0.7 mg/kg to about 2.15 mg/kg, about 0.85 mg/kg to about 2 mg/kg, about 1 mg/kg to about 1.85 mg/kg, about 1.15 mg/kg to about 1.7 mg/kg, about 1.3 mg/kg mg to about 1.6 mg/kg, about 1.35 mg/kg to about 1.5 mg/kg, about 2.15 mg/kg to about 3.6 mg/kg, about 2.3 mg/kg to about 3.4 mg/kg, about 2.4 mg/kg to about 3.3 mg/kg, about 2.6 mg/kg to about 3.15 mg/kg, about 2.7 mg/kg to about 3 mg/kg, about 2.8 mg/kg to about 3 mg/kg, or about 2.85 mg/kg to about 2.95 mg/kg. In some embodiments, an effective dosage of a BTK inhibitor of Formula (I) or Formula (II) is about 0.35 mg/kg, about 0.7 mg/kg, about 1 mg/kg, about 1.4 mg/kg, about 1.8 mg/kg, about 2.1 mg/kg, about 2.5 mg/kg, about 2.85 mg/kg, about 3.2 mg/kg, or about 3.6 mg/kg.

In some embodiments, a BTK inhibitor of Formula (I) or Formula (II) is adminstered at a dosage of 10 to 400 mg BID, including a dosage of 25 mg, 50 mg, 75 mg, 100 mg, 150 mg, 175 mg, 200 mg, 225 mg, 250 mg, 275 mg, 300 mg, 325 mg, 350 mg, 375 mg, and 400 mg BID.

An effective amount of the combination of the BTK inhibitor of Formula (I) or Formula (II) may be administered in either single or multiple doses by any of the accepted modes of administration of agents having similar utilities, including rectal, buccal, sublingual, intranasal and transdermal routes, by intra-arterial injection, intravenously, intraperitoneally, parenterally, intramuscularly, subcutaneously, orally, topically, or as an inhalant.

Methods of Treating Hematological Malignancies, Cancers, and Other Diseases

In an embodiment, the invention relates to a method of treating CLL in a human that comprises the step of administering to said human a therapeutically effective amount of a BTK inhibitor of Formula (II), or a pharmaceutically acceptable salt or ester, prodrug, cocrystal, solvate or hydrate thereof. In an embodiment, the invention relates to a method of treating SLL in a human that comprises the step of administering to said human a therapeutically effective amount of a BTK inhibitor of Formula (II), or a pharmaceutically acceptable salt or ester, prodrug, cocrystal, solvate or hydrate thereof. In an embodiment, the invention relates to a method of treating CLL in a human that comprises the step of administering to said human a therapeutically effective amount of a BTK inhibitor of Formula (I), or a pharmaceutically acceptable salt or ester, prodrug, cocrystal, solvate or hydrate thereof. In an embodiment, the invention relates to a method of treating SLL in a human that comprises the step of administering to said human a therapeutically effective amount of a BTK inhibitor of Formula (I), or a pharmaceutically acceptable salt or ester, prodrug, cocrystal, solvate or hydrate thereof.

In an embodiment, the invention relates to a method of treating CLL in a human that comprises the step of administering to said human a BTK inhibitor of Formula (II), or a pharmaceutically acceptable salt or ester, prodrug, cocrystal, solvate or hydrate thereof, in a dosing regimen selected from the group consisting of 100 mg QD, 175 mg QD, 250 mg QD, 400 mg QD, and 100 mg BID. In an embodiment, the invention relates to a method of treating CLL in a human that comprises the step of administering to said human a BTK inhibitor of Formula (I), or a pharmaceutically acceptable salt or ester, prodrug, cocrystal, solvate or hydrate thereof, in a dosing regimen selected from the group consisting of 100 mg QD, 175 mg QD, 250 mg QD, 400 mg QD, and 100 mg BID.

In an embodiment, the invention relates to a use of a composition of Formula (II), or a pharmaceutically acceptable salt or ester, prodrug, cocrystal, solvate or hydrate thereof, in the manufacture of a medicament for treating CLL, wherein the treating comprises the step of administering one or more doses of Formula (II) or a pharmaceutically acceptable salt or ester, prodrug, cocrystal, solvate or hydrate thereof. In an embodiment, the invention relates to a use of a composition of Formula (II), or a pharmaceutically acceptable salt or ester, prodrug, cocrystal, solvate or hydrate thereof, in the manufacture of a medicament for treating SLL, wherein the treating comprises the step of administering one or more doses of Formula (II) or a pharmaceutically acceptable salt or ester, prodrug, cocrystal, solvate or hydrate thereof. In an embodiment, the invention relates to a use of a composition of Formula (I), or a pharmaceutically acceptable salt or ester, prodrug, cocrystal, solvate or hydrate thereof, in the manufacture of a medicament for treating CLL, wherein the treating comprises the step of administering one or more doses of Formula (I) or a pharmaceutically acceptable salt or ester, prodrug, cocrystal, solvate or hydrate thereof. In an embodiment, the invention relates to a use of a composition of Formula (I), or a pharmaceutically acceptable salt or ester, prodrug, cocrystal, solvate or hydrate thereof, in the manufacture of a medicament for treating SLL, wherein the treating comprises the step of administering one or more doses of Formula (I) or a pharmaceutically acceptable salt or ester, prodrug, cocrystal, solvate or hydrate thereof.

In an embodiment, the invention relates to a method of treating CLL in a mammal that comprises the step of administering to said mammal a therapeutically effective amount of a BTK inhibitor of Formula (II), or a pharmaceutically acceptable salt or ester, prodrug, cocrystal, solvate or hydrate thereof. In an embodiment, the invention relates to a method of treating SLL in a mammal that comprises the step of administering to said mammal a therapeutically effective amount of a BTK inhibitor of Formula (II), or a pharmaceutically acceptable salt or ester, prodrug, cocrystal, solvate or hydrate thereof. In an embodiment, the invention relates to a method of treating CLL in a mammal that comprises the step of administering to said mammal a therapeutically effective amount of a BTK inhibitor of Formula (I), or a pharmaceutically acceptable salt or ester, prodrug, cocrystal, solvate or hydrate thereof. In an embodiment, the invention relates to a method of treating SLL in a mammal that comprises the step of administering to said mammal a therapeutically effective amount of a BTK inhibitor of Formula (I), or a pharmaceutically acceptable salt or ester, prodrug, cocrystal, solvate or hydrate thereof. In an embodiment, the mammal in any of the foregoing embodiments is selected from the group consisting of a human, a canine, a feline, or an equine. In an embodiment, the mammal in any of the foregoing embodiments is a companion animal.

In an embodiment, the invention relates to a method of treating a subtype of CLL in a human that comprises the step of administering to said mammal a therapeutically effective amount of a BTK inhibitor of Formula (I) or Formula (II), or a pharmaceutically acceptable salt or ester, prodrug, cocrystal, solvate or hydrate thereof. A number of subtypes of CLL have been characterized. CLL is often classified for immunoglobulin heavy-chain variable-region (IgV$_H$) mutational status in leukemic cells. R. N. Damle, et al., *Blood* 1999, 94, 1840-47; T. J. Hamblin, et al., *Blood* 1999, 94, 1848-54. Patients with IgV$_H$ mutations generally survive longer than patients without IgV$_H$ mutations. ZAP70 expression (positive or negative) is also used to characterize CLL. L. Z. Rassenti, et al., *N. Engl. J. Med.* 2004, 351, 893-901. The methylation of ZAP-70 at CpG3 is also used to characterize CLL, for example by pyrosequencing. R. Claus, et al., *J. Clin. Oncol.* 2012, 30, 2483-91; J. A. Woyach, et al., *Blood* 2014, 123, 1810-17. CLL is also classified by stage of disease under the Binet or Rai criteria. J. L. Binet, et al., *Cancer* 1977, 40, 855-64; K. R. Rai, T. Han, *Hematol. Oncol. Clin. North Am.* 1990, 4, 447-56. Other common mutations, such as 11p deletion, 13q deletion, and 17p deletion can be assessed using well-known techniques such as fluorescence in situ hybridization (FISH). In an embodiment, the invention relates to a method of treating a CLL in a human that comprises the step of administering to said mammal a therapeutically effective amount of a BTK inhibitor of Formula (II), or a pharmaceutically acceptable salt or ester, prodrug, cocrystal, solvate or hydrate thereof, wherein the CLL is selected from the group consisting of IgV$_H$ mutation negative CLL, ZAP-70 positive CLL, ZAP-70 methylated at CpG3 CLL, CD38 positive CLL, chronic lymphocytic leukemia characterized by a 17p13.1 (17p) deletion, and CLL characterized by a 11q22.3 (11q) deletion.

In an embodiment, the invention relates to a method of treating a CLL in a human that comprises the step of administering to said mammal a therapeutically effective amount of a BTK inhibitor of Formula (II), or a pharmaceutically acceptable salt or ester, prodrug, cocrystal, solvate or hydrate thereof, wherein the CLL has undergone a Richter's transformation. Methods of assessing Richter's transformation, which is also known as Richter's syndrome, are described in P. Jain and S. O'Brien, *Oncology*, 2012, 26, 1146-52. Richter's transformation is a subtype of CLL that is observed in 5-10% of patients. It involves the development of aggressive lymphoma from CLL and has a generally poor prognosis.

In an embodiment, the invention relates to a method of treating a subtype of CLL in a human, comprising the step of administering to said mammal a therapeutically effective amount of a BTK inhibitor of Formula (II), or a pharmaceutically acceptable salt or ester, prodrug, cocrystal, solvate or hydrate thereof, wherein the subtype of CLL is a subtype of CLL that increases monocytes and NK cells in peripheral blood when measured after a period of treatment with Formula (II) selected from the group consisting of about 14 days, about 28 days, about 56 days, about 1 month, about 2 months, about 3 months, about 6 months, and about 1 year, and wherein the term "about" refers to a measurement interval of +/−2 days.

In an embodiment, the invention relates to a method of treating chronic lymphocytic leukemia in a patient, wherein the chronic lymphocytic leukemia is chronic lymphocytic leukemia in a patient sensitive to lymphocytosis. In an embodiment, the invention relates to a method of treating chronic lymphocytic leukemia in a patient, wherein the chronic lymphocytic leukemia is chronic lymphocytic leukemia in a patient exhibiting lymphocytosis caused by a disorder selected from the group consisting of a viral infection, a bacterial infection, a protozoal infection, or a post-splenectomy state. In an embodiment, the viral infection in any of the foregoing embodiments is selected from the group consisting of infectious mononucleosis, hepatitis, and cytomegalovirus. In an embodiment, the bacterial infection in any of the foregoing embodiments is selected from the group consisting of pertussis, tuberculosis, and brucellosis.

The methods described above may be used as first-line cancer therapy, or after treatment with conventional chemotherapic active pharmaceutical ingredients, including cyclophosphamide, fludarabine, cyclophosphamide and fludarabine (FC chemotherapy), and chlorambucil. The methods described above may also be supplemented with immunotherapeutic monoclonal antibodies such as the anti-CD52 monoclonal antibody alemtuzumab. In an embodiment, the invention relates to a method of treating CLL in a human that comprises the step of administering to said human a therapeutically effective amount of a BTK inhibitor of Formula (II), or a pharmaceutically acceptable salt, ester, prodrug, cocrystal, solvate or hydrate thereof, and further comprises the step of administering to said human an active pharmaceutical ingredient selected from the group consisting of cyclophosphamide, fludarabine, cyclophosphamide, chlorambucil, salts, esters, prodrugs, cocrystals, solvates, or hydrates thereof, and combinations thereof, and alemtuzumab, antigen-binding fragments, derivatives, conjugates, variants, and radioisotope-labeled complexes thereof.

In an embodiment, the invention relates to a method of treating hematological malignancies in a human comprising the step of administering to said human a therapeutically effective amount of a BTK inhibitor of Formula (II), or a pharmaceutically acceptable salt or ester, prodrug, cocrystal, solvate or hydrate thereof. Hematological malignancies include CLL and SLL, as well as other cancers of the blood, including B cell malignancies. In an embodiment, the invention relates to a method of treating a hematological malignancy selected from the group consisting of non-Hodgkin's lymphoma (NHL), diffuse large B cell lymphoma (DLBCL), follicular lymphoma (FL), mantle cell lymphoma (MCL), Hodgkin's lymphoma, B cell acute lymphoblastic leukemia (B-ALL), Waldenström's macroglobulinemia (WM), Burkitt's lymphoma, multiple myeloma, or myelofibrosis in a human that comprises the step of administering a therapeutically effective amount of a BTK inhibitor of Formula (II), or a pharmaceutically acceptable salt or ester, prodrug, cocrystal, solvate or hydrate thereof.

In an embodiment, the invention relates to a method of treating a NHL selected from the group consisting of indolent NHL and aggressive NHL comprising the step of administering a therapeutically effective amount of a BTK inhibitor of Formula (II), or a pharmaceutically acceptable salt or ester, prodrug, cocrystal, solvate or hydrate thereof.

In an embodiment, the invention relates to a method of treating a DLBCL selected from the group consisting of activated B-cell like diffuse large B-cell lymphoma (DLBCL-ABC) and germinal center B-cell like diffuse large B-cell lymphoma (DLBCL-GCB), comprising the step of administering a therapeutically effective amount of a BTK inhibitor of Formula (II), or a pharmaceutically acceptable salt or ester, prodrug, cocrystal, solvate or hydrate thereof.

In an embodiment, the invention relates to a method of treating an MCL selected from the group consisting of mantle zone MCL, nodular MCL, diffuse MCL, and blastoid MCL (also known as blastic variant MCL), comprising the step of administering a therapeutically effective amount of a BTK inhibitor of Formula (II), or a pharmaceutically acceptable salt or ester, prodrug, cocrystal, solvate or hydrate thereof.

In an embodiment, the invention relates to a method of treating a B-ALL selected from the group consisting of early pre-B cell B-ALL, pre-B cell B-ALL, and mature B cell B-ALL (also known as Burkitt's leukemia), comprising the step of administering a therapeutically effective amount of a BTK inhibitor of Formula (II), or a pharmaceutically acceptable salt or ester, prodrug, cocrystal, solvate or hydrate thereof.

In an embodiment, the invention relates to a method of treating a Burkitt's lymphoma selected from the group consisting of sporadic Burkitt's lymphoma, endemic Burkitt's lymphoma, and human immunodeficiency virus-associated Burkitt's lymphoma, comprising the step of administering a therapeutically effective amount of a BTK inhibitor of Formula (II), or a pharmaceutically acceptable salt or ester, prodrug, cocrystal, solvate or hydrate thereof.

In an embodiment, the invention relates to a method of treating a multiple myeloma selected from the group consisting of hyperdiploid multiple myeloma and non-hyperdiploid multiple myeloma, comprising the step of administering a therapeutically effective amount of a BTK inhibitor of Formula (II), or a pharmaceutically acceptable salt or ester, prodrug, cocrystal, solvate or hydrate thereof.

In an embodiment, the invention relates to a method of treating a myelofibrosis selected from the group consisting of primary myelofibrosis (also known as chronic idiopathic myelofibrosis) and myelofibrosis secondary to polycythemia vera or essential thrombocythaemia, comprising the step of administering a therapeutically effective amount of a BTK inhibitor of Formula (II), or a pharmaceutically acceptable salt or ester, prodrug, cocrystal, solvate or hydrate thereof.

In an embodiment, the invention relates to a method of treating a subtype of a hematological malignancy in a human, comprising the step of administering to said human a therapeutically effective amount of a BTK inhibitor of Formula (II), or a pharmaceutically acceptable salt or ester, prodrug, cocrystal, solvate or hydrate thereof, wherein the subtype of a hematological malignancy is a subtype of a hematological malignancy that increases monocytes and NK cells in peripheral blood when measured after a period of treatment with Formula (II) selected from the group consisting of about 14 days, about 28 days, about 56 days, about 1 month, about 2 months, about 3 months, about 6 months, and about 1 year, wherein the term "about" refers to a measurement interval of +/−2 days, and wherein the hematological malignancy is selected from the group consisting of non-Hodgkin's lymphoma (NHL), diffuse large B cell lymphoma (DLBCL), follicular lymphoma (FL), mantle cell lymphoma (MCL), Hodgkin's lymphoma, B cell acute lymphoblastic leukemia (B-ALL), Waldenström's macroglobulinemia (WM), Burkitt's lymphoma, multiple myeloma, or myelofibrosis.

Methods of Treating Cancers in Patients Sensitive to Thrombosis

In selected embodiments, the invention provides a method of treating a cancer in a human sensitive to platelet-mediated thrombosis, comprising the step of administering a therapeutically effective dose of a BTK inhibitor, or a pharmaceutically-acceptable salt, cocrystal, hydrate, solvate, or prodrug thereof. In an embodiment, the invention provides a method of treating a cancer in a human sensitive to platelet-mediated thrombosis, comprising the step of administering a therapeutically effective dose of a BTK inhibitor, wherein the BTK inhibitor is Formula (II), or a pharmaceutically-acceptable salt, cocrystal, hydrate, solvate, or prodrug thereof. In an embodiment, the invention provides a method of treating a cancer in a human sensitive to platelet-mediated thrombosis, comprising the step of administering a therapeutically effective dose of a BTK inhibitor, wherein the BTK inhibitor is Formula (II), or a pharmaceutically-acceptable salt, cocrystal, hydrate, solvate, or prodrug thereof, further comprising the step of administering a therapeutically effective dose of an anticoagulant or anti-platelet active pharmaceutical ingredient.

In selected embodiments, the BTK inhibitor of Formula (I) or Formula (II) and the anticoagulant or the antiplatelet active pharmaceutical ingredient are administered sequentially. In selected embodiments, the BTK inhibitor of Formula (I) or Formula (II) and the anticoagulant or the antiplatelet active pharmaceutical ingredient are administered concomitantly. In selected embodiments, the BTK inhibitor of Formula (I) or Formula (II) is administered before the anticoagulant or the antiplatelet active pharmaceutical ingredient. In selected embodiments, the BTK inhibitor of Formula (I) or Formula (II) is administered after the anticoagulant or the antiplatelet active pharmaceutical ingredient.

In selected embodiments, the invention provides a method of treating a cancer in a human sensitive to platelet-mediated thrombosis, comprising the step of administering a therapeutically effective dose of a BTK inhibitor, wherein the BTK inhibitor is Formula (II), and wherein the cancer is selected from the group consisting of CLL, SLL, NHL, DLBCL, FL, MCL, Hodgkin's lymphoma, B-ALL, WM, Burkitt's lymphoma, multiple myeloma, or myelofibrosis that comprises the step of administering a therapeutically effective amount of a BTK inhibitor of Formula (II), or a pharmaceutically acceptable salt or ester, prodrug, cocrystal, solvate or hydrate thereof.

In selected embodiments, the invention provides a method of treating a cancer in a human sensitive to platelet-mediated thrombosis, comprising the step of administering a therapeutically effective dose of a BTK inhibitor, wherein the BTK inhibitor is Formula (II), and wherein the cancer is selected from the group consisting of acute myeloid leukemia, squamous cell carcinoma including chronic myelocytic leukemia, bladder cancer, head and neck tumor, pancreatic ductal adenocarcinoma (PDA), pancreatic cancer, colon carcinoma, mammary carcinoma, breast cancer, fibrosarcoma, mesothelioma cancer, renal cell carcinoma, lung carcinoma, thyoma, prostate cancer, colorectal cancer, ovarian cancer, thymus cancer, brain cancer, squamous cell cancer, skin cancer, eye cancer, retinoblastoma, melanoma, intraocular melanoma, oral cavity and oropharyngeal cancers, gastric cancer, stomach cancer, cervical cancer, renal cancer, kidney cancer, liver cancer, ovarian cancer, prostate cancer, colorectal cancer, esophageal cancer, testicular cancer, gynecological cancer, thyroid cancer, acquired immune deficiency syndrome (AIDS)-related cancers (e.g., lymphoma and Kaposi's sarcoma), viral-induced cancer, glioblastoma, esophageal tumors, hematological neoplasms, non-small-cell lung cancer, esophagus tumor, hepatitis C virus infection, hepatocellular carcinoma, metastatic colon cancer, multiple myeloma, ovary tumor, pancreas tumor, renal cell carcinoma, small-cell lung cancer, and stage IV melanoma.

In an embodiment, the invention provides a method of treating a cancer in a human sensitive to platelet-mediated thrombosis, comprising the step of administering a therapeutically effective dose of a BTK inhibitor, wherein the BTK inhibitor is Formula (I) or Formula (II), or a pharmaceutically-acceptable salt, cocrystal, hydrate, solvate, or prodrug thereof, wherein the cancer is a hematological malignancy, and wherein the hematological malignancy is selected from the group consisting of chronic lymphocytic leukemia, B cell acute lymphoblastic leukemia, and non-Hodgkin's lymphoma.

In an embodiment, the invention provides a method of treating a cancer in a human sensitive to platelet-mediated thrombosis, comprising the step of administering a therapeutically effective dose of a BTK inhibitor, wherein the BTK inhibitor is Formula (II), or a pharmaceutically-acceptable salt, cocrystal, hydrate, solvate, or prodrug thereof, further comprising the step of administering a therapeutically effective dose of an anticoagulant or antiplatelet active pharmaceutical ingredient, wherein the cancer is a hematological malignancy, and wherein the hematological malignancy is selected from the group consisting of chronic lymphocytic leukemia, B cell acute lymphoblastic leukemia, and non-Hodgkin's lymphoma.

Preferred anti-platelet and anticoagulant agents for use in the methods of the present invention include, but are not limited to, cyclooxygenase inhibitors (e.g., aspirin), adenosine diphosphate (ADP) receptor inhibitors (e.g., clopidogrel and ticlopidine), phosphodiesterase inhibitors (e.g., cilostazol), glycoprotein IIb/IIIa inhibitors (e.g., abciximab, eptifibatide, and tirofiban), adenosine reuptake inhibitors (e.g., dipyridamole), and acetylsalicylic acid (aspirin). Examples of anti-platelet active pharmaceutical ingredients for use in the methods of the present invention include acenocoumarol, anagrelide, anagrelide hydrochloride, abciximab, aloxiprin, antithrombin, apixaban, argatroban, aspirin, aspirin with extended-release dipyridamole, beraprost, betrixaban, bivalirudin, carbasalate calcium, cilostazol, clopidogrel, clopidogrel bisulfate, cloricromen, dabigatran etexilate, darexaban, dalteparin, dalteparin sodium, defibrotide, dicumarol, diphenadione, dipyridamole, ditazole, desirudin, edoxaban, enoxaparin, enoxaparin sodium, eptifibatide, fondaparinux, fondaparinux sodium, heparin, heparin sodium, heparin calcium, idraparinux, idraparinux sodium, iloprost, indobufen, lepirudin, low molecular weight heparin, melagatran, nadroparin, otamixaban, parnaparin, phenindione, phenprocoumon, prasugrel, picotamide, prostacyclin, ramatroban, reviparin, rivaroxaban, sulodexide, terutroban, terutroban sodium, ticagrelor, ticlopidine, ticlopidine hydrochloride, tinzaparin, tinzaparin sodium, tirofiban, tirofiban hydrochloride, treprostinil, treprostinil sodium, triflusal, vorapaxar, warfarin, warfarin sodium, ximelagatran, salts thereof, solvates thereof, hydrates thereof, cocrystals thereof, prodrugs thereof, and combinations thereof.

In an embodiment, the invention provides a method of treating a cancer in a human sensitive to platelet-mediated thrombosis, comprising the step of administering a therapeutically effective dose of a BTK inhibitor, wherein the BTK inhibitor is Formula (II), or a pharmaceutically-acceptable salt, cocrystal, hydrate, solvate, or prodrug thereof, further comprising the step of administering a therapeutically effective dose of an anticoagulant or antiplatelet active pharmaceutical ingredient, wherein the anticoagulant or antiplatelet active pharmaceutical ingredient is selected from the group consisting of acenocoumarol, anagrelide, anagrelide hydrochloride, abciximab, aloxiprin, antithrombin, apixaban, argatroban, aspirin, aspirin with extended-release dipyridamole, beraprost, betrixaban, bivalirudin, carbasalate calcium, cilostazol, clopidogrel, clopidogrel bisulfate, cloricromen, dabigatran etexilate, darexaban, dalteparin, dalteparin sodium, defibrotide, dicumarol, diphenadione, dipyridamole, ditazole, desirudin, edoxaban, enoxaparin, enoxaparin sodium, eptifibatide, fondaparinux, fondaparinux sodium, heparin, heparin sodium, heparin calcium, idraparinux, idraparinux sodium, iloprost, indobufen, lepirudin, low molecular weight heparin, melagatran, nadroparin, otamixaban, parnaparin, phenindione, phenprocoumon, prasugrel, picotamide, prostacyclin, ramatroban, reviparin, rivaroxaban, sulodexide, terutroban, terutroban sodium, ticagrelor, ticlopidine, ticlopidine hydrochloride, tinzaparin, tinzaparin sodium, tirofiban, tirofiban hydrochloride, treprostinil, treprostinil sodium, triflusal, vorapaxar, warfarin, warfarin sodium, ximelagatran, salts thereof, solvates thereof, hydrates thereof, cocrystals thereof, prodrugs thereof, and combinations thereof.

Combinations of BTK Inhibitors and Anti-CD20 Antibodies

The BTK inhibitors of Formula (I) and Formula (II) may also be safely co-administered with immunotherapeutic antibodies such as the anti-CD20 antibodies rituximab, obinutuzumab, ofatumumab, veltuzumab, tositumomab, and ibritumomab, and or antigen-binding fragments, derivatives, conjugates, variants, and radioisotope-labeled complexes thereof, which may be given alone or with conventional chemotherapeutic active pharmaceutical ingredients such as those described herein. The CD20 antigen also called human B-lymphocyte-restricted differentiation antigen, Bp35, or B1) is found on the surface of normal "pre-B" and mature B lymphocytes, including malignant B lymphocytes. L. M. Nadler, et al., *J. Clin. Invest.* 1981, 67, 134-40; P. Stashenko, et al., *J. Immunol.* 1980, 139, 3260-85. The CD20 antigen is a glycosylated integral membrane protein with a molecular weight of approximately 35 kD. T. F. Tedder, et al., *Proc. Natl. Acad. Sci. USA,* 1988, 85, 208-12. CD20 is also expressed on most B cell non-Hodgkin's lymphoma cells, but is not found on hematopoietic stem cells, pro-B cells, normal plasma cells, or other normal tissues. Anti-CD20 antibodies are currently used as therapies for many hematological malignancies, including indolent NHL, aggressive NHL, and CLL/SLL. S. H. Lim, et. al., *Haematologica* 2010, 95, 135-43; S. A. Beers, et. al., *Sem. Hematol.* 2010, 47, 107-14; C. Klein, et al., *mAbs* 2013, 5, 22-33.

In an embodiment, the invention relates to a method of treating a hematological malignancy in a human comprising the step of administering to said human a BTK inhibitor of Formula (II), or a pharmaceutically acceptable salt or ester, prodrug, cocrystal, solvate or hydrate thereof, and further comprising the step of administering an anti-CD20 antibody, wherein the anti-CD20 antibody is a monoclonal antibody or an antigen-binding fragment, derivative, conjugate, variant, or radioisotope-labeled complex thereof. In an embodiment, the invention relates to a method of treating a hematological malignancy in a human comprising the step of administering to said human a BTK inhibitor of Formula (II), or a pharmaceutically acceptable salt or ester, prodrug, cocrystal, solvate or hydrate thereof, and further comprising the step of administering an anti-CD20 antibody, wherein the anti-CD20 antibody is an anti-CD20 monoclonal antibody or an antigen-binding fragment, derivative, conjugate, variant, or radioisotope-labeled complex thereof, and wherein the anti-CD20 antibody specifically binds to human CD20 with a $K_D$ selected from the group consisting of $1 \times 10^{-7}$ M or less, $5 \times 10^{-8}$ M or less, $1 \times 10^{-8}$ M or less, and $5 \times 10^{-9}$ M or less.

In an embodiment, the invention relates to a method of treating CLL or SLL in a human comprising the step of administering to said human a BTK inhibitor of Formula (II), or a pharmaceutically acceptable salt or ester, prodrug, cocrystal, solvate or hydrate thereof, and further comprising the step of administering an anti-CD20 antibody, wherein the anti-CD20 antibody is a monoclonal antibody or an antigen-binding fragment, derivative, conjugate, variant, or radioisotope-labeled complex thereof. In an embodiment, the invention relates to a method of treating CLL or SLL in a human comprising the step of administering to said human a BTK inhibitor of Formula (II), or a pharmaceutically acceptable salt or ester, prodrug, cocrystal, solvate or hydrate thereof, and further comprising the step of administering an anti-CD20 antibody, wherein the anti-CD20 antibody is an anti-CD20 monoclonal antibody or an antigen-binding fragment, derivative, conjugate, variant, or radioisotope-labeled complex thereof, and wherein the anti-CD20 antibody specifically binds to human CD20 with a $K_D$ selected from the group consisting of $1\times10^{-7}$ M or less, $5\times10^{-8}$ M or less, $1\times10^{-8}$ M or less, and $5\times10^{-9}$ M or less.

In selected embodiments, the BTK inhibitor of Formula (I) or Formula (II) and the anti-CD20 monoclonal antibody are administered sequentially. In selected embodiments, the BTK inhibitor of Formula (I) or Formula (II) and the anti-CD20 monoclonal antibody are administered concomitantly. In selected embodiments, the BTK inhibitor of Formula (I) or Formula (II) is administered before the anti-CD20 monoclonal antibody. In selected embodiments, the BTK inhibitor of Formula (I) or Formula (II) is administered after the anticoagulant or the antiplatelet active pharmaceutical ingredient. In selected embodiments, the BTK inhibitor of Formula (I) or Formula (II) and the anti-CD20 monoclonal antibody are administered over the same time period, and the BTK inhibitor administration continues after the anti-CD20 monoclonal antibody administration is completed.

In an embodiment, the anti-CD20 monoclonal antibody is rituximab, or an antigen-binding fragment, derivative, conjugate, variant, or radioisotope-labeled complex thereof. Rituximab is a chimeric murine-human monoclonal antibody directed against CD20, and its structure comprises an IgG1 kappa immunoglobulin containing murine light- and heavy-chain variable region sequences and human constant region sequences. Rituximab is composed of two heavy chains of 451 amino acids and two light chains of 213 amino acids. The amino acid sequence for the heavy chains of rituximab is set forth in SEQ ID NO:1. The amino acid sequence for the light chains of rituximab is set forth in SEQ ID NO:2. Rituximab is commercially available, and its properties and use in cancer and other diseases is described in more detail in W. Rastetter, et al., *Ann. Rev. Med.* 2004, 55, 477-503, and in G. L. Plosker and D. P. Figgett, *Drugs*, 2003, 63, 803-43. In an embodiment, the anti-CD20 monoclonal antibody is an anti-CD20 biosimilar monoclonal antibody approved by drug regulatory authorities with reference to rituximab. In an embodiment, the anti-CD20 monoclonal antibody has a heavy chain sequence identity of greater than 90% to SEQ ID NO:1. In an embodiment, the anti-CD20 monoclonal antibody has a light chain sequence identity of greater than 90% to SEQ ID NO:2. In an embodiment, the anti-CD20 monoclonal antibody has a heavy chain sequence identity of greater than 95% to SEQ ID NO:1. In an embodiment, the anti-CD20 monoclonal antibody has a light chain sequence identity of greater than 95% to SEQ ID NO:2. In an embodiment, the anti-CD20 monoclonal antibody has a heavy chain sequence identity of greater than 98% to SEQ ID NO:1. In an embodiment, the anti-CD20 monoclonal antibody has a light chain sequence identity of greater than 98% to SEQ ID NO:2. In an embodiment, the anti-CD20 monoclonal antibody has a heavy chain sequence identity of greater than 99% to SEQ ID NO:1. In an embodiment, the anti-CD20 monoclonal antibody has a light chain sequence identity of greater than 99% to SEQ ID NO:2.

In an embodiment, the anti-CD20 monoclonal antibody is obinutuzumab, or an antigen-binding fragment, derivative, conjugate, variant, or radioisotope-labeled complex thereof. Obinutuzumab is also known as afutuzumab or GA-101. Obinutuzumab is a humanized monoclonal antibody directed against CD20. The amino acid sequence for the heavy chains of obinutuzumab is set forth in SEQ ID NO:3. The amino acid sequence for the light chains of obinutuzumab is set forth in SEQ ID NO:4. Obinutuzumab is commercially available, and its properties and use in cancer and other diseases is described in more detail in T. Robak, *Curr. Opin. Investig. Drugs* 2009, 10, 588-96. In an embodiment, the anti-CD20 monoclonal antibody is an anti-CD20 biosimilar monoclonal antibody approved by drug regulatory authorities with reference to obinutuzumab. In an embodiment, the anti-CD20 monoclonal antibody has a heavy chain sequence identity of greater than 90% to SEQ ID NO:3. In an embodiment, the anti-CD20 monoclonal antibody has a light chain sequence identity of greater than 90% to SEQ ID NO:4. In an embodiment, the anti-CD20 monoclonal antibody has a heavy chain sequence identity of greater than 95% to SEQ ID NO:3. In an embodiment, the anti-CD20 monoclonal antibody has a light chain sequence identity of greater than 95% to SEQ ID NO:4. In an embodiment, the anti-CD20 monoclonal antibody has a heavy chain sequence identity of greater than 98% to SEQ ID NO:3. In an embodiment, the anti-CD20 monoclonal antibody has a light chain sequence identity of greater than 98% to SEQ ID NO:4. In an embodiment, the anti-CD20 monoclonal antibody has a heavy chain sequence identity of greater than 99% to SEQ ID NO:3. In an embodiment, the anti-CD20 monoclonal antibody has a light chain sequence identity of greater than 99% to SEQ ID NO:4. In an embodiment, the anti-CD20 monoclonal antibody obinutuzumab is an immunoglobulin G1, anti-(human B-lymphocyte antigen CD20 (membrane-spanning 4-domains subfamily A member 1, B-lymphocyte surface antigen B1, Leu-16 or Bp35)), humanized mouse monoclonal obinutuzumab des-CH3107-K-γ1 heavy chain (222-219')-disulfide with humanized mouse monoclonal obinutuzumab κ light chain dimer (228-228":231-231")-bisdisulfide antibody.

In an embodiment, the anti-CD20 monoclonal antibody is ofatumumab, or an antigen-binding fragment, derivative, conjugate, variant, or radioisotope-labeled complex thereof. Ofatumumab is described in B. D. Cheson, *J. Clin. Oncol.* 2010, 28, 3525-30. The crystal structure of the Fab fragment of ofatumumab has been reported in Protein Data Bank reference 3GIZ and in J. Du, et al., *Mol. Immunol.* 2009, 46, 2419-2423. Ofatumumab is commercially available, and its preparation, properties, and use in cancer and other diseases is described in more detail in U.S. Pat. No. 8,529,202 B2, the disclosure of which is incorporated herein by reference. In an embodiment, the anti-CD20 monoclonal antibody is an anti-CD20 biosimilar monoclonal antibody approved by drug regulatory authorities with reference to ofatumumab. In an embodiment, the anti-CD20 monoclonal antibody has a variable heavy chain sequence identity of greater than 90% to SEQ ID NO:5. In an embodiment, the anti-CD20 monoclonal antibody has a variable light chain sequence identity of greater than 90% to SEQ ID NO:6. In an embodiment, the anti-CD20 monoclonal antibody has a variable heavy chain sequence identity of greater than 95% to SEQ ID NO:5. In an embodiment, the anti-CD20 monoclonal antibody has a variable light chain sequence identity of greater than 95% to SEQ ID NO:6. In an embodiment, the anti-CD20 monoclonal antibody has a variable heavy chain sequence identity of greater than 98% to SEQ ID NO:5. In an embodiment, the anti-CD20 monoclonal antibody has a variable light chain sequence identity of greater than 98% to SEQ ID NO:6. In an embodiment, the anti-CD20 monoclonal antibody has a variable heavy chain sequence identity of greater than 99% to SEQ ID NO:5. In an embodiment, the anti-CD20 monoclonal antibody has a variable light chain sequence identity of greater than 99% to SEQ ID NO:6. In an embodiment, the anti-CD20 monoclonal antibody has a Fab fragment heavy chain sequence identity of greater than 90% to SEQ ID NO:7. In an embodiment, the anti-CD20 monoclonal antibody has a Fab fragment light chain sequence identity of greater than 90% to SEQ ID NO:8. In an embodiment, the anti-CD20 monoclonal antibody has a Fab fragment heavy chain sequence identity of greater than 95% to SEQ ID NO:7. In an embodiment, the anti-CD20 monoclonal antibody has a Fab fragment light chain sequence identity of greater than 95% to SEQ ID NO:8. In an embodiment, the anti-CD20 monoclonal antibody has a Fab fragment heavy chain sequence identity of greater than 98% to SEQ ID NO:7. In an embodiment, the anti-CD20 monoclonal antibody has a Fab fragment light chain sequence identity of greater than 98% to SEQ ID NO:8. In an embodiment, the anti-CD20 monoclonal antibody has a Fab fragment heavy chain sequence identity of greater than 99% to SEQ ID NO:7. In an embodiment, the anti-CD20 monoclonal antibody has a Fab fragment light chain sequence identity of greater than 99% to SEQ ID NO:8. In an embodiment, the anti-CD20 monoclonal antibody ofatumumab is an immunoglobulin G1, anti-(human B-lymphocyte antigen CD20 (membrane-spanning 4-domains subfamily A member 1, B-lymphocyte surface antigen B1, Leu-16 or Bp35)); human monoclonal ofatumumab-CD20 γ1 heavy chain (225-214')-disulfide with human monoclonal ofatumumab-CD20 κ light chain, dimer (231-231":234-234")-bisdisulfide antibody.

In an embodiment, the anti-CD20 monoclonal antibody is veltuzumab, or an antigen-binding fragment, derivative, conjugate, variant, or radioisotope-labeled complex thereof. Veltuzumab is also known as hA20. Veltuzumab is described in D. M. Goldenberg, et al., *Leuk. Lymphoma* 2010, 51, 747-55. In an embodiment, the anti-CD20 monoclonal antibody is an anti-CD20 biosimilar monoclonal antibody approved by drug regulatory authorities with reference to veltuzumab. In an embodiment, the anti-CD20 monoclonal antibody has a heavy chain sequence identity of greater than 90% to SEQ ID NO:9. In an embodiment, the anti-CD20 monoclonal antibody has a light chain sequence identity of greater than 90% to SEQ ID NO:10. In an embodiment, the anti-CD20 monoclonal antibody has a heavy chain sequence identity of greater than 95% to SEQ ID NO:9. In an embodiment, the anti-CD20 monoclonal antibody has a light chain sequence identity of greater than 95% to SEQ ID NO:10. In an embodiment, the anti-CD20 monoclonal antibody has a heavy chain sequence identity of greater than 98% to SEQ ID NO:9. In an embodiment, the anti-CD20 monoclonal antibody has a light chain sequence identity of greater than 98% to SEQ ID NO:10. In an embodiment, the anti-CD20 monoclonal antibody has a heavy chain sequence identity of greater than 99% to SEQ ID NO:9. In an embodiment, the anti-CD20 monoclonal antibody has a light chain sequence identity of greater than 99% to SEQ ID NO:10. In an embodiment, the anti-CD20 monoclonal antibody ofatumumab is an immunoglobulin G1, anti-(human B-lymphocyte antigen CD20 (membrane-spanning 4-domains subfamily A member 1, Leu-16, Bp35)); [218-arginine, 360-glutamic acid, 362-methionine]humanized mouse monoclonal hA20 γ1 heavy chain (224-213')-disulfide with humanized mouse monoclonal hA20 κ light chain (230-230":233-233")-bisdisulfide dimer In an embodiment, the anti-CD20 monoclonal antibody is tositumomab, or an antigen-binding fragment, derivative, conjugate, variant, or radioisotope-labeled complex thereof. In an embodiment, the anti-CD20 monoclonal antibody is $^{131}$I-labeled tositumomab. In an embodiment, the anti-CD20 monoclonal antibody is an anti-CD20 biosimilar monoclonal antibody approved by drug regulatory authorities with reference to tositumomab. In an embodiment, the anti-CD20 monoclonal antibody has a heavy chain sequence identity of greater than 90% to SEQ ID NO:11. In an embodiment, the anti-CD20 monoclonal antibody has a light chain sequence identity of greater than 90% to SEQ ID NO:12. In an embodiment, the anti-CD20 monoclonal antibody has a heavy chain sequence identity of greater than 95% to SEQ ID NO:11. In an embodiment, the anti-CD20 monoclonal antibody has a light chain sequence identity of greater than 95% to SEQ ID NO:12. In an embodiment, the anti-CD20 monoclonal antibody has a heavy chain sequence identity of greater than 98% to SEQ ID NO:11. In an embodiment, the anti-CD20 monoclonal antibody has a light chain sequence identity of greater than 98% to SEQ ID NO:12. In an embodiment, the anti-CD20 monoclonal antibody has a heavy chain sequence identity of greater than 99% to SEQ ID NO:11. In an embodiment, the anti-CD20 monoclonal antibody has a light chain sequence identity of greater than 99% to SEQ ID NO:12.

In an embodiment, the anti-CD20 monoclonal antibody is ibritumomab, or an antigen-binding fragment, derivative, conjugate, variant, or radioisotope-labeled complex thereof. The active form of ibritumomab used in therapy is ibritumomab tiuxetan. When used with ibritumomab, the chelator tiuxetan (diethylene triamine pentaacetic acid) is complexed with a radioactive isotope such as $^{90}$Y or $^{111}$In. In an embodiment, the anti-CD20 monoclonal antibody is ibritumomab tiuxetan, or radioisotope-labeled complex thereof. In an embodiment, the anti-CD20 monoclonal antibody is an anti-CD20 biosimilar monoclonal antibody approved by drug regulatory authorities with reference to tositumomab. In an embodiment, the anti-CD20 monoclonal antibody has a heavy chain sequence identity of greater than 90% to SEQ ID NO:13. In an embodiment, the anti-CD20 monoclonal antibody has a light chain sequence identity of greater than 90% to SEQ ID NO:14. In an embodiment, the anti-CD20 monoclonal antibody has a heavy chain sequence identity of greater than 95% to SEQ ID NO:13. In an embodiment, the anti-CD20 monoclonal antibody has a light chain sequence identity of greater than 95% to SEQ ID NO:14. In an embodiment, the anti-CD20 monoclonal antibody has a heavy chain sequence identity of greater than 98% to SEQ ID NO:13. In an embodiment, the anti-CD20 monoclonal antibody has a light chain sequence identity of greater than 98% to SEQ ID NO:14. In an embodiment, the anti-CD20 monoclonal antibody has a heavy chain sequence identity of greater than 99% to SEQ ID NO:13. In an embodiment, the anti-CD20 monoclonal antibody has a light chain sequence identity of greater than 99% to SEQ ID NO:14.

In an embodiment, an anti-CD20 antibody selected from the group consisting of obinutuzumab, ofatumumab, veltuzumab, tositumomab, and ibritumomab, and or antigen-binding fragments, derivatives, conjugates, variants, and radioisotope-labeled complexes thereof, is administered to a subject by infusion in a dose selected from the group consisting of about 100 mg, about 200 mg, about 300 mg, about 400 mg, about 500 mg, about 600 mg, about 700 mg, about 800 mg, about 900 mg, about 1000 mg, about 1100 mg, about 1200 mg, about 1300 mg, about 1400 mg, about 1500 mg, about 1600 mg, about 1700 mg, about 1800 mg, about 1900 mg, and about 2000 mg. In an embodiment, the anti-CD20 antibody is administered weekly. In an embodiment, the anti-CD20 antibody is administered monthly. In an embodiment, the anti-CD20 antibody is administered at a lower initial dose, which is escalated when administered at subsequent intervals administered monthly. For example, the first infusion can deliver 300 mg of anti-CD20 antibody, and subsequent weekly doses could deliver 2,000 mg of anti-CD20 antibody for eight weeks, followed by monthly doses of 2,000 mg of anti-CD20 antibody. During any of the foregoing embodiments, the BTK inhibitors of Formula (I) or Formula (II) may be administered daily, twice daily, or at different intervals as described above, at the dosages described above.

In an embodiment, the invention provides a kit comprising a composition comprising a BTK inhibitor of Formula (I) or Formula (II) and a composition comprising an anti-CD20 antibody selected from the group consisting of rituximab, obinutuzumab, ofatumumab, veltuzumab, tositumomab, and ibritumomab, or an antigen-binding fragment, derivative, conjugate, variant, or radioisotope-labeled complex thereof, for use in the treatment of CLL or SLL, hematological malignancies, B cell malignancies, or any of the other diseases described herein. The compositions are typically both pharmaceutical compositions. The kit is for use in co-administration of the anti-CD20 antibody and the BTK inhibitor, either simultaneously or separately, in the treatment of CLL or SLL, hematological malignancies, B cell malignancies, or any of the other diseases described herein.

EXAMPLES

The embodiments encompassed herein are now described with reference to the following examples. These examples are provided for the purpose of illustration only and the disclosure encompassed herein should in no way be construed as being limited to these examples, but rather should be construed to encompass any and all variations which become evident as a result of the teachings provided herein.

Example 1—Preclinical Study of a Second Generation BTK Inhibitor for Use in CLL/SLL The BTK inhibitor ibrutinib ((1-[(3R)-3-[4-amino-3-(4-phenoxyphenyl)-1H-pyrazolo[3,4-d]pyrimidin-1-yl]piperidin-1-yl]prop-2-en-1-one) is a first-generation BTK inhibitor. In clinical testing as a monotherapy in subjects with hematologic malignancies, ibrutinib was generally well tolerated at dose levels through 840 mg (the highest dose tested). R. H. Advani, et al., *J. Clin. Oncol.* 2013, 31, 88-94; J. C. Byrd, et al., *N. Engl. J. Med.* 2013, 369, 32-42; M. L. Wang, et al., *N. Engl. J Med.* 2013, 369, 507-16. No maximum tolerated dose (MTD) was apparent within the tested dose range. Furthermore, subjects typically found the drug tolerable over periods extending to >2 years. No subject had tumor lysis syndrome. No overt pattern of myelosuppression was associated with ibrutinib treatment. No drug-related reductions in circulating CD4+ T cells or serum immunoglobulins were noted. Adverse events with an apparent relationship to study drug included diarrhea and rash.

In subjects with heavily pretreated non-Hodgkin lymphoma (NHL), ibrutinib showed substantial antitumor activity, inducing durable regressions of lymphadenopathy and splenomegaly in most subjects. Improvements in disease-associated anemia and thrombocytopenia were observed. The pattern of changes in subjects with CLL was notable. Single-agent ibrutinib caused rapid and substantial reductions in lymph node size concomitant with a redistribution of malignant sites into the peripheral blood. An asymptomatic absolute lymphocyte count (ALC) increase was observed that was maximal during the first few months of treatment and generally decreased thereafter but could be persistent in some subjects or could be seen repeatedly in subjects who had interruption and resumption of drug therapy.

Collectively, these data with ibrutinib support the potential benefits of selective BTK inhibition in the treatment of subjects with relapsed lymphoid cancers. However, while highly potent in inhibiting BTK, ibrutinib has also shown in vitro activity against other kinases with a cysteine in the same position as Cys481 in BTK to which the drug covalently binds. For example, ibrutinib inhibits epidermal growth factor receptor (EGFR), which may be the cause of ibrutinib-related diarrhea and rash. In addition, it is a substrate for both cytochrome P450 (CYP) enzymes 3A4/5 and 2D6, which increases the possibility of drug-drug interactions. These liabilities support the development of alternative BTK inhibitors for use in the therapy of lymphoid cancer.

The preclinical selectivity and potency characteristics of the second-generation BTK inhibitor of Formula (II) were compared to the first-generation BTK inhibitor ibrutinib. In Table 1, a kinome screen (performed Life Technologies or based on literature data) is shown that compares these compounds.

TABLE 1

Kinome Screen for BTK Inhibitors (IC$_{50}$, nM)

| 3F-Cys Kinase | Formula (II) | Ibrutinib |
|---|---|---|
| Btk | 3.1 | 0.5 |
| Tec | 29 | 78 |
| Bmx | 39 | 0.80 |
| Itk | >1000 | 10.7 |
| Txk | 291 | 2.0 |
| EGFR | >1000 | 5.6 |
| ErbB2 | 912 | 9.4 |
| ErbB4 | 13.2 | 2.7 |
| Blk | >1000 | 0.5 |
| JAK-3 | >1000 | 16.1 |

The results shown in Table 1 are obtained from a 10 point biochemical assay generated from 10 point concentration curves. The BTK inhibitor of Formula (II) shows much greater selectivity for BTK compared to other kinases than ibrutinib.

A comparison of the in vivo potency results for the BTK inhibitors of Formula (II) and ibrutinib is shown in FIG. 1. CD86 and CD69 are cell surface proteins that are BCR activation markers. To obtain the in vivo potency results, mice were gavaged at increasing drug concentration and sacrificed at one time point (3 h post-dose). BCR was stimulated with IgM and the expression of activation marker CD69 and CD86 are monitored by flow cytometry and to determine EC$_{50}$ values.

Formula (II) is currently being evaluated in an ongoing study of canine spontaneous B-cell lymphoma. Six dogs have been treated with Formula (II) using 2.5 mg/kg once daily oral administration for an average of 22 days (range 14 to 42 days). To date, partial remission (PR), per Veterinary Cooperative Oncology Group criteria for assessment of response in peripheral nodal lymphoma, has been observed in 2 of 6 dogs. D. M. Vali, et al., *Vet. Comp. Oncol.* 8, 28-37 (2010). No drug-related adverse events have been reported to date in this study. These findings are preliminary and similar to the clinical responses (i.e., 3 dogs with PR out of 8 dogs treated) observed with ibrutinib in dogs with spontaneous B-cell lymphoma. L. A. Honigberg, et al., *Proc. Nat. Acad. Sci. USA*, 107, 13075-13080 (2010).

In vitro and in vivo safety pharmacology studies with Formula (II) have demonstrated a favorable nonclinical safety profile. When screened at 10 µM in binding assays evaluating interactions with 80 known pharmacologic targets such as G-protein-coupled receptors, nuclear receptors, proteases, and ion channels, Formula (II) shows significant activity only against the A3 adenosine receptor; follow-up dose-response experiments indicated a $IC_{50}$ of 2.7 µM, suggesting a low clinical risk of off-target effects. Formula (II) at 10 µM showed no inhibition of in vitro EGFR phosphorylation in an A431 human epidermoid cancer cell line whereas ibrutinib had an $IC_{50}$ of 66 nM. The in vitro effect of Formula (II) on human ether-à-go-go-related gene (hERG) channel activity was investigated in vitro in human embryonic kidney cells stably transfected with hERG. Formula (II) inhibited hERG channel activity by 25% at 10 µM, suggesting a low clinical risk that Formula (II) would induce clinical QT prolongation as predicted by this assay. Formula (II) was well tolerated in standard in vivo Good Laboratory Practices (GLP) studies of pharmacologic safety. A functional observation battery in rats at doses of through 300 mg/kg (the highest dose level) revealed no adverse effects on neurobehavioral effects or body temperature at any dose level. A study of respiratory function in rats also indicated no treatment-related adverse effects at doses through 300 mg/kg (the highest dose level). In a cardiovascular function study in awake telemeterized male beagle dogs, single doses of Formula (II) at dose levels through 30 mg/kg (the highest dose level) induced no meaningful changes in body temperature, cardiovascular, or electrocardiographic (ECG) (including QT interval) parameters. The results suggest that Formula (II) is unlikely to cause serious off-target effects or adverse effects on critical organ systems.

The drug-drug interaction potential of Formula (II) was also evaluated. In vitro experiments evaluating loss of parent drug as catalyzed by CYPs indicated that Formula (II) is metabolized by CYP3A4. In vitro metabolism studies using mouse, rat, dog, rabbit, monkey, and human hepatocytes incubated with $^{14}$C-labeled Formula (II) indicated two mono-oxidized metabolites and a glutathione conjugate. No unique human metabolite was identified. Preliminary evaluations of metabolism in the plasma, bile, and urine of rats, dogs, and monkeys indicated metabolic processes of oxidation, glutathione binding, and hydrolysis. It was shown that Formula (II) binds to glutathione but does not deplete glutathione in vitro. Nonclinical CYP interaction studies data indicate that Formula (II) is very unlikely to cause clinical drug-drug interactions through alteration of the metabolism of drugs that are substrates for CYP enzymes.

Example 2—Clinical Study of a Second Generation BTK Inhibitor for Use in CLL/SLL Clinical studies have shown that targeting the BCR signaling pathway by inhibiting BTK produces significant clinical benefit in patients with non-Hodgkin's lymphoma (NHL). The second generation BTK inhibitor, Formula (II), achieves significant oral bioavailability and potency, and has favorable preclinical characteristics, as described above. The purpose of this study is to evaluate the safety and efficacy of the second generation BTK inhibitor of Formula (II) in treating subjects with chronic lymphocytic leukemia (CLL) and small lymphocytic lymphoma (SLL).

The design and conduct of this study is supported by an understanding of the history and current therapies for subjects with lymphoid cancers; knowledge of the activity and safety of a first-generation BTK inhibitor, ibrutinib, in subjects with hematologic cancers; and the available nonclinical information regarding Formula (II). The collective data support the following conclusions. BTK expression plays an important role in the biology of lymphoid neoplasms, which represent serious and life-threatening disorders with continuing unmet medical need. Clinical evaluation of Formula (II) as a potential treatment for these disorders has sound scientific rationale based on observations that the compound selectively abrogates BTK activity and shows activity in nonclinical models of lymphoid cancers. These data are supported by clinical documentation that ibrutinib, a first-generation BTK inhibitor, is clinically active in these diseases. Ibrutinib clinical data and Formula (II) nonclinical safety pharmacology and toxicology studies support the safety of testing Formula (II) in subjects with B cell malignancies.

The primary objectives of the clinical study are as follows: (1) establish the safety and the MTD of orally administered Formula (II) in subjects with CLL/SLL; (2) determine pharmacokinetics (PK) of orally administered Formula (II) and identification of its major metabolite(s); and (3) measure pharmacodynamic (PD) parameters including drug occupancy of BTK, the target enzyme, and effect on biologic markers of B cell function.

The secondary objective of the clinical study is to evaluate tumor responses in patients treated with Formula (II).

This study is a multicenter, open-label, nonrandomized, sequential group, dose escalation study. The following dose cohorts will be evaluated:

Cohort 1: 100 mg/day for 28 days (=1 cycle)
Cohort 2: 175 mg/day for 28 days (=1 cycle)
Cohort 3: 250 mg/day for 28 days (=1 cycle)
Cohort 4: 350 mg/day for 28 days (=1 cycle)
Cohort 5: 450 mg/day for 28 days (=1 cycle)
Cohort 6: To be determined amount in mg/day for 28 days (=1 cycle)

Each cohort will be enrolled sequentially with 6 subjects per cohort. If ≤1 dose-limiting toxicity (DLT) is observed in the cohort during Cycle 1, escalation to the next cohort will proceed. Subjects may be enrolled in the next cohort if 4 of the 6 subjects enrolled in the cohort completed Cycle 1 without experiencing a DLT, while the remaining 2 subjects are completing evaluation. If ≥2 DLTs are observed during Cycle 1, dosing at that dose and higher will be suspended and the MTD will be established as the previous cohort. The MTD is defined as the largest daily dose for which fewer than 33% of the subjects experience a DLT during Cycle 1. Dose escalation will end when either the MTD is achieved or at 3 dose levels above full BTK occupancy, whichever occurs first. Full BTK occupancy is defined as Formula (II) active-site occupancy of >80% (average of all subjects in cohort) at 24 hours postdose. Should escalation to Cohort 6 be necessary, the dose will be determined based on the aggregate data from Cohorts 1 to 5, which includes safety, efficacy, and PK/PD results. The dose for Cohort 6 will not exceed 900 mg/day.

Treatment with Formula (II) may be continued for >28 days until disease progression or an unacceptable drug-related toxicity occurs. Subjects with disease progression will be removed from the study. All subjects who discontinue study drug will have a safety follow-up visit 30 (±7) days after the last dose of study drug unless they have started another cancer therapy within that timeframe. Radiologic tumor assessment will be done at screening and at the end of Cycle 2, Cycle 4, and Cycle 12 and at investigator discretion. Confirmation of complete response (CR) will require bone marrow analysis and radiologic tumor assessment. For subjects who remain on study for >11 months, a mandatory bone marrow aspirate and biopsy is required in Cycle 12 concurrent with the radiologic tumor assessment.

All subjects will have standard hematology, chemistry, and urinalysis safety panels done at screening. This study also includes pancreatic function assessment (serum amylase and serum lipase) due to the pancreatic findings in the 28-day GLP rat toxicity study. Once dosing commences, all subjects will be evaluated for safety once weekly for the first 4 weeks, every other week for Cycle 2, and monthly thereafter. Blood samples will be collected during the first week of treatment for PK/PD assessments. ECGs will be done at screening, and on Day 1-2, 8, 15, 22, 28 of Cycle 1, Day 15 and 28 of Cycle 2, and monthly thereafter through Cycle 6. ECGs are done in triplicate for screening only. Thereafter, single ECG tests are done unless a repeat ECG testing is required.

Dose-limiting toxicity is defined as any of the following events (if not related to disease progression): (1) any Grade ≥3 non-hematologic toxicity (except alopecia) persisting despite receipt of a single course of standard outpatient symptomatic therapy (e.g., Grade 3 diarrhea that responds to a single, therapeutic dose of Imodium® would not be considered a DLT); (2) grade ≥3 prolongation of the corrected QT interval (QTc), as determined by a central ECG laboratory overread; (3) grade 4 neutropenia (absolute neutrophil count [ANC]<500/μL) lasting >7 days after discontinuation of therapy without growth factors or lasting >5 days after discontinuation of therapy while on growth factors (i.e., Grade 4 neutropenia not lasting as long as specified will not be considered a DLT), (4) grade 4 thrombocytopenia (platelet count <20,000/μL) lasting >7 days after discontinuation of therapy or requiring transfusion (i.e., Grade 4 thrombocytopenia not lasting as long as specified will not be considered a DLT), and (5) dosing delay due to toxicity for >7 consecutive days.

The efficacy parameters for the study include overall response rate, duration of response, and progression-free survival (PFS). The safety parameters for the study include DLTs and MTD, frequency, severity, and attribution of adverse events (AEs) based on the Common Terminology Criteria for Adverse Events (CTCAE v4.03) for non-hematologic AEs. M. Hallek, et al., *Blood* 2008, 111, 5446-5456.

The schedule of assessments is as follows, with all days stated in the following meaning the given day or +/−2 days from the given day. A physical examination, including vital signs and weight, are performed at screening, during cycle 1 at 1, 8, 15, 22, and 28 days, during cycle 2 at 15 and 28 days, during cycles 3 to 24 at 28 days, and at follow up (after the last dose). The screening physical examination includes, at a minimum, the general appearance of the subject, height (screening only) and weight, and examination of the skin, eyes, ears, nose, throat, lungs, heart, abdomen, extremities, musculoskeletal system, lymphatic system, and nervous system. Symptom-directed physical exams are done thereafter. Vital signs (blood pressure, pulse, respiratory rate, and temperature) are assessed after the subject has rested in the sitting position. Eastern Cooperative Oncology Group (ECOG) status is assessed at screening, during cycle 1 at 1, 8, 15, 22, and 28 days, during cycle 2 at 15 and 28 days, during cycles 3 to 24 at 28 days, and at follow up, using the published ECOG performance status indications described in M. M. Oken, et al., *Am. J. Clin. Oncol.* 1982, 5, 649-655. ECG testing is performed at screening, during cycle 1 at 1, 2, 8, 15, 22, and 28 days, during cycle 2 at 15 and 28 days, during cycles 3 to 24 at 28 days, and at follow up. The 12-lead ECG test will be done in triplicate (≥1 minute apart) at screening. The calculated QTc average of the 3 ECGs must be <480 ms for eligibility. On cycle 1, day 1 and cycle 1, day 8, single ECGs are done predose and at 1, 2, 4, and 6 h postdose. The single ECG on Cycle 1 Day 2 is done predose. On cycle 1, day 15, day 22, and day 28, a single ECG is done 2 hours post-dose. Starting with cycle 2, a single ECG is done per visit. Subjects should be in supine position and resting for at least 10 minutes before study-related ECGs. Two consecutive machine-read QTc >500 ms or >60 ms above baseline require central ECG review. Hematology, including complete blood count with differential and platelet and reticulocyte counts, is assessed at screening, during cycle 1 at 1, 8, 15, 22, and 28 days, during cycle 2 at 15 and 28 days, during cycles 3 to 24 at 28 days, and at follow up. Serum chemistry is assessed at screening, during cycle 1 at 1, 8, 15, 22, and 28 days, during cycle 2 at 15 and 28 days, during cycles 3 to 24 at 28 days, and at follow up. Serum chemistry includes albumin, alkaline phosphatase, ALT, AST, bicarbonate, blood urea nitrogen (BUN), calcium, chloride, creatinine, glucose, lactate dehydrogenase (LDH), magnesium, phosphate, potassium, sodium, total bilirubin, total protein, and uric acid. Cell counts and serum immunoglobulin are performed at screening, at cycle 2, day 28, and at every 6 months thereafter until last dose and include T/B/NK/monocyte cell counts (CD3, CD4, CD8, CD14, CD19, CD19, CD16/56, and others as needed) and serum immunoglobulin (IgG, IgM, IgA, and total immunoglobulin). Bone marrow aspirates are performed at cycle 12. Pharmacodynamics samples are drawn during cycle 1 at 1, 2, and 8 days, and at follow up. On days 1 and 8, pharmacodynamic samples are drawn pre-dose and 4 hours (±10 minutes) post-dose, and on day 2, pharmacodynamic samples are drawn pre-dose. Pharmacokinetics samples are drawn during cycle 1 at 1, 2, 8, 15, 22, and 28 days. Pharmacokinetic samples for Cycle 1 Day 1 are drawn pre-dose and at 0.5, 1, 2, 4, 6 and 24 hours (before dose on Day 2) post-dose. Samples for Cycle 1 Day 8 are drawn pre-dose and at 0.5, 1, 2, 4, and 6 hours post-dose. On Cycle 1 Day 15, 22, and 28, a PK sample is drawn pre-dose and the second PK sample must be drawn before (up to 10 minutes before) the ECG acquisition, which is 2 hours postdose. Pretreatment radiologic tumor assessments are performed within 30 days before the first dose. A computed tomography (CT) scan (with contrast unless contraindicated) is required of the chest, abdomen, and pelvis. In addition, a positron emission tomography (PET) or PET/CT must done for subjects with SLL. Radiologic tumor assessments are mandatory at the end of Cycle 2 (−7 days), Cycle 4 (−7 days), and Cycle 12 (−7 days). Otherwise, radiologic tumor assessments are done at investigator discretion. A CT (with contrast unless contraindicated) scan of the chest, abdomen, and pelvis is required for subjects with CLL. In addition, a PET/CT is required in subjects with SLL. Bone marrow and radiologic assessments are both required for confirmation of a complete response (CR). Clinical assessments of tumor response should be done at the end of Cycle 6 and every 3 months thereafter. Molecular markers are measured at screening, and include interphase cytogenetics, stimulated karyotype, IgHV mutational status, Zap-70 methylation, and beta-2 microglobulin levels. Urinalysis is performed at screening, and includes pH, ketones, specific gravity, bilirubin, protein, blood, and glucose. Other assessments, including informed consent, eligibility, medical history, and pregnancy test are done at the time of screening.

The investigator rates the subject's response to treatment based on recent guidelines for CLL, as given in M. Hallek, et al., *Blood* 2008, 111, 5446-56, and for SLL, as given in B. D. Cheson, et al., *J. Clin. Oncol.* 2007, 25, 579-586. The response assessment criteria for CLL are summarized in Table 2.

TABLE 2

Response Assessment Criteria for CLL. Abbreviations: ANC = absolute neutrophil count; CR = complete remission; CRi = CR with incomplete blood count recovery; PR = partial remission.

| Response | Peripheral Blood | Bone Marrow (if performed) | Nodes, Liver, and Spleen[a] |
|---|---|---|---|
| CR | Lymphocytes <4 × 10$^9$/L<br>ANC >1.5 × 10$^9$/L[b]<br>Platelets >100 × 10$^9$/L[b]<br><br>Hemoglobin >11.0 g/dL (untransfused)[b] | Normocellular<br><30%lymphocytes<br>No B-lymphoid nodules | Normal(e.g., no lymph nodes >1.5 cm) |
| CRi | Lymphocytes <4 × 10$^9$/L<br>Persistent anemia, thrombocytopenia, or neutropenia related to drug toxicity | Hypocellular<br><30%lymphocytes | Normal(e.g., no lymph nodes >1.5 cm) |
| PR | Lymphocytes ≥50% decrease from baseline<br>ANC >1.5 × 10$^9$/L or<br>Platelets >100 × 10$^9$/L or<br>50% improvement over baseline[b] or<br>Hemoglobin >11.0 g/dL or<br>50% improvement over baseline (untransfused)[b] | Not assessed | ≥50% reduction in lymphadenopathy[c] and/or in spleen or liver enlargement |

[a]Computed tomography (CT) scan of abdomen pelvis, and chest is required for this evaluation
[b]Without need for exogenous growth factors
[c]In the sum products of <6 lymph nodes or in the largest diameter of the enlarged lymph node(s) detected before therapy and no increase in any lymph node or new enlarged lymph nodes The response assessment criteria for SLL are summarized in Table 3.

TABLE 3

Response Assessment Criteria for SLL. Abbreviations: CR = complete remission, CT = computed tomography, FDG = [18F] fluorodeoxyglucose, PET = positron-emission tomography, PR = partial remission, SD = stable disease, SPD = sum of the product of the diameters.

| Response | Definition | Nodal Masses | Spleen, Liver | Bone Marrow |
|---|---|---|---|---|
| CR | Disappearance of all evidence of disease | (a) FDG-avid or PET positive prior to therapy; mass of any size permitted if PET negative (b) Variably FDG-avid or PET negative; regression to normal size on CT | Not palpable, nodules disappeared | If infiltrate present at screening, infiltrate cleared on repeat biopsy; if indeterminate by morphology, immunohistochemistry should be negative |
| PR | Regression of measurable disease and no new sites | ≥50% decrease in SPD of up to 6 largest dominant masses; no increase in size of other nodes (a) FDG-avid or PET positive prior to therapy; ≥1 PET positive at previously involved site (b) Variably FDG-avid or PET negative; regression on CT | ≥50% decrease in SPD of nodules (for single nodule in greatest transverse diameter); no increase in size of liver or spleen | Irrelevant if positive prior to therapy; cell type should be specified |
| SD | Failure to attain CR/PR or progressive disease | (a) FDG-avid or PET positive prior to therapy; PET positive at prior sites of disease, and no new sites on CT or PET (b) Variably FDG avid or PET negative; no change in size of previous lesions on CT | | |

The PK parameters of the study are as follows. The plasma PK of Formula (II) and a metabolite is characterized using noncompartmental analysis. The following PK parameters are calculated, whenever possible, from plasma concentrations of Formula (II):

$AUC_{(0-t)}$: Area under the plasma concentration-time curve calculated using linear trapezoidal summation from time 0 to time t, where t is the time of the last measurable concentration (Ct), $AUC_{(0-24)}$: Area under the plasma concentration-time curve from 0 to 24 hours, calculated using linear trapezoidal summation, $AUC_{(0-\infty)}$: Area under the plasma concentration-time curve from 0 to infinity, calculated using the formula: $AUC_{(0-\infty)} = AUC_{(0-t)} + Ct/\lambda z$, where $\lambda z$ is the apparent terminal elimination rate constant, $C_{max}$: Maximum observed plasma concentration, $T_{max}$: Time of the maximum plasma concentration (obtained without interpolation), $t_{1/2}$: Terminal elimination half-life (whenever possible), $\lambda_z$: Terminal elimination rate constant (whenever possible), Cl/F: Oral clearance.

The PD parameters of the study are as follows. The occupancy of BTK by Formula (II) are measured in peripheral blood mononuclear cells (PBMCs) with the aid of a biotin-tagged Formula (II) analogue probe. The effect of Formula (II) on biologic markers of B cell function will also be evaluated.

The statistical analysis used in the study is as follows. No formal statistical tests of hypotheses are performed. Descriptive statistics (including means, standard deviations, and medians for continuous variables and proportions for discrete variables) are used to summarize data as appropriate.

The following definitions are used for the safety and efficacy analysis sets: Safety analysis set: All enrolled subjects who receive ≥1 dose of study drug; Per-protocol (PP) analysis set: All enrolled subjects who receive ≥1 dose of study drug and with ≥1 tumor response assessment after treatment. The safety analysis set will be used for evaluating the safety parameters in this study. The PP analysis sets will be analyzed for efficacy parameters in this study.

No imputation of values for missing data is performed except for missing or partial start and end dates for adverse events and concomitant medication will be imputed according to prespecified, conservative imputation rules. Subjects lost to follow-up (or drop out) will be included in statistical analyses to the point of their last evaluation.

The safety endpoint analysis was performed as follows. Safety summaries will include summaries in the form of tables and listings. The frequency (number and percentage) of treatment emergent adverse events will be reported in each treatment group by Medical Dictionary for Regulatory Activities (MedDRA) System Organ Class and Preferred Term. Summaries will also be presented by the severity of the adverse event and by relationship to study drug. Laboratory shift tables containing counts and percentages will be prepared by treatment assignment, laboratory parameter, and time. Summary tables will be prepared for each laboratory parameter. Figures of changes in laboratory parameters over time will be generated. Vital signs, ECGs, and physical exams will be tabulated and summarized.

Additional analyses include summaries of subject demographics, baseline characteristics, compliance, and concurrent treatments. Concomitant medications will be coded according to the World Health Organization (WHO) Drug Dictionary and tabulated.

The analysis of efficacy parameters was performed as follows. The point estimate of the overall response rate will be calculated for the PP analysis set. The corresponding 95% confidence interval also will be derived. The duration of overall response is measured from the time measurement criteria are met for CR or PR (whichever is first recorded) until the first date that recurrent or progressive disease is objectively documented (taking as reference for progressive disease the smallest measurements recorded since the treatment started). Kaplan-Meier methodology will be used to estimate event-free curves and corresponding quantiles (including the median). Progression-free survival is measured from the time of first study drug administration until the first date that recurrent or progressive disease is objectively documented (taking as reference for progressive disease the smallest measurements recorded since the treatment started). Kaplan-Meier methodology will be used to estimate the event-free curves and corresponding quantiles (including the median).

The study scheme is a sequential cohort escalation. Each cohort consists of six subjects. The sample size of the study is 24 to 36 subjects, depending on dose escalation into subsequent cohorts. Cohort 1 (N=6) consists of Formula (II), 100 mg QD for 28 days. Cohort 2 (N=6) consists of Formula (II), 175 mg QD for 28 days. Cohort 3 (N=6) consists of Formula (II), 250 mg QD for 28 days. Cohort 4 (N=6) consists of Formula (II), 350 mg QD for 28 days. Cohort 5 (N=6) consists of Formula (II), 450 mg QD for 28 days. Cohort 6 (N=6) consists of Formula (II), at a dose to be determined QD for 28 days. The dose level for Cohort 6 will be determined based on the safety and efficacy of Cohorts 1 to 5, and will not exceed 900 mg/day. Escalation will end with either the MTD cohort or three levels above full BTK occupancy, whichever is observed first. An additional arm of the study will explore 100 mg BID dosing. Treatment with oral Formula (II) may be continued for greater than 28 days until disease progression or an unacceptable drug-related toxicity occurs.

The inclusion criteria for the study are as follows: (1) men and women ≥18 years of age with a confirmed diagnosis of CLL/SLL, which has relapsed after, or been refractory to, ≥2 previous treatments for CLL/SLL; however, subjects with 17p deletion are eligible if they have relapsed after, or been refractory to, 1 prior treatment for CLL/SLL; (2) body weight ≥60 kg, (3) ECOG performance status of ≤2; (4) agreement to use contraception during the study and for 30 days after the last dose of study drug if sexually active and able to bear children; (5) willing and able to participate in all required evaluations and procedures in this study protocol including swallowing capsules without difficulty; or (6) ability to understand the purpose and risks of the study and provide signed and dated informed consent and authorization to use protected health information (in accordance with national and local subject privacy regulations).

The dosage form and strength of Formula (II) used in the clinical study is a hard gelatin capsules prepared using standard pharmaceutical grade excipients (microcrystalline cellulose) and containing 25 mg of Formula (II) each. The color of the capsules is Swedish orange. The route of administration is oral (per os, or PO). The dose regimen is once daily or twice daily, as defined by the cohort, on an empty stomach (defined as no food 2 hours before and 30 minutes after dosing).

The baseline characteristics for the patients enrolled in the clinical study are given in Table 4.

TABLE 4

Relapsed/refractory CLL baseline characteristics.

| Characteristic | CLL (N = 44) |
|---|---|
| Patient Demographics | |
| Age (years), median (range) | 62 (45-84) |
| Sex, men (%) | 33 (75) |
| Prior therapies, median (range), n | 3 (1-10) |
| ≥3 prior therapies, n (%) | 26 (59) |
| Clinical Details | |
| ECOG performance status >1 (%) | 28 (63) |
| Rai stage III/IV | 16 (36) |
| Bulky disease >5 cm, n (%) | 15 (34) |
| Cytopenia at baseline | 33 (75) |
| Cytogenic Status | |
| Chromosome 11q22.3 deletion (Del 11q), n (%) | 18 01) |
| Chromosome 17p13.1 (Del 17p), n (%) | 19 (34) |
| IgV$_H$ status (unmutated), n (%) | 28 (64) |

The results of the clinical study in relapsed/refractory CLL patients are summarized in Table 5.

TABLE 5

Activity of Formula (II) in relapsed/refractory CLL. (PR = partial response; PR + L = partial response with lymphocytosis; SD-stable disease; PD-progressive disease.)

| n (%) | All Cohorts (N = 31)† | 100 mg QD (N = 8) | 175 mg QD (N = 8) | 250 mg QD (N = 7) | 100 mg BID (N = 3) | 400 mg QD (N = 5) |
|---|---|---|---|---|---|---|
| PR | 22 (71) | 7 (88) | 5 (63) | 5 (71) | 3 (100) | 2 (40) |
| PR + L | 7 (23) | 0 (0) | 3 (37) | 2 (29) | 0 (0) | 2 (40) |
| SD | 2 (6) | 1 (12) | 0 (0) | 0 (0) | 0 (0) | 1 (20) |
| PD | 0 (0) | 0 (0) | 0 (0) | 0 (0) | 0 (0) | 0 (0) |
| Median (range) Cycles | | | | | | |
| 7.3 (3.0-10.8) | 10.0 (9.0-10.8) | 8.6 (3.0-8.8) | 7.0 (7.0-7.3) | 5.2 (4.7-5.5) | 5.0 (4.8-5.5) | |

Figure 2:
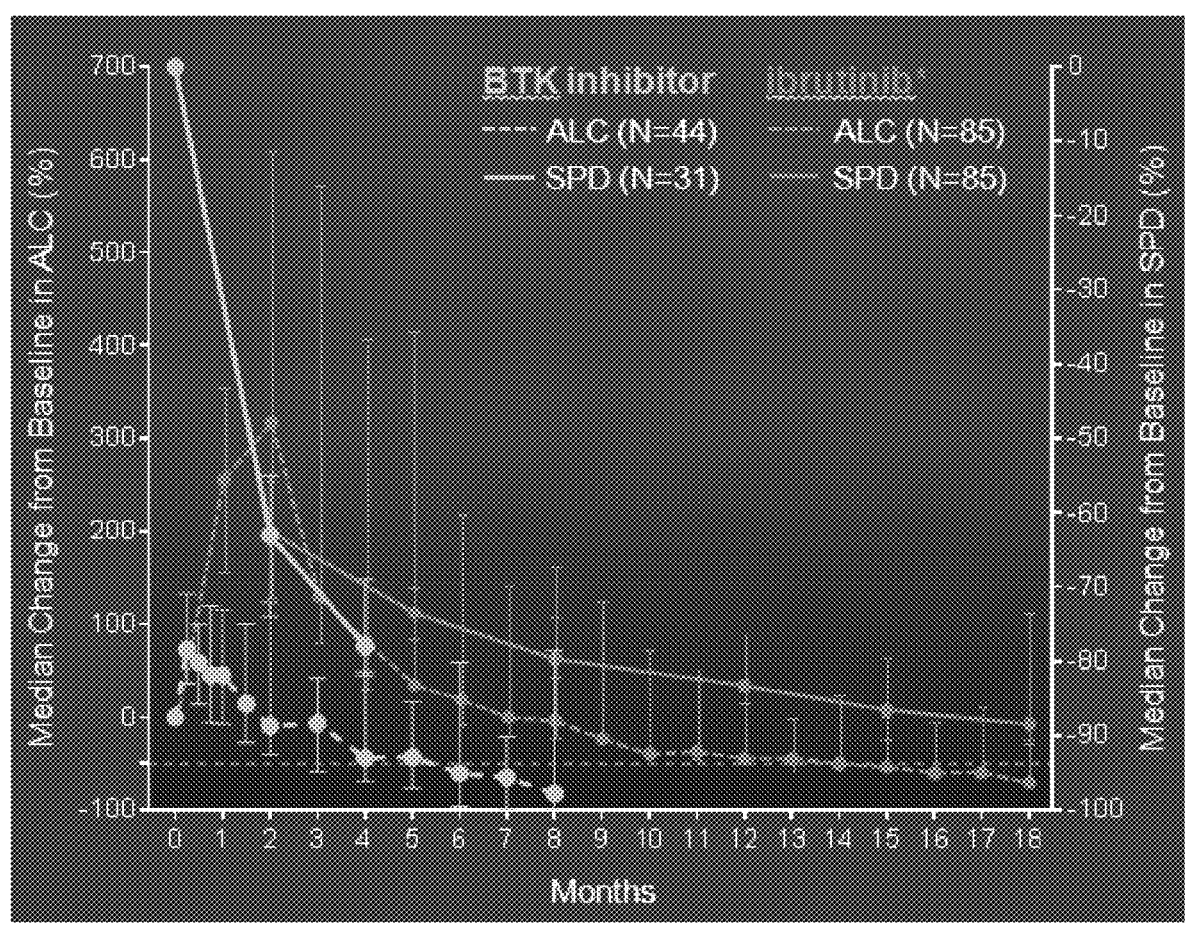
FIG. 2 illustrates the results of the clinical study of Formula (II) (labeled "BTK inhibitor") in CLL, which are shown in comparison to the results reported for ibrutinib in FIG. 1A of J. C. Byrd, et al., *N. Engl. J. Med.* 2013, 369, 32-42. The results show that the BTK inhibitor of Formula (II) causes a much smaller relative increase and much faster decrease in absolute lymphocyte count (ALC) relative to the BTK inhibitor ibrutinib. The sum of the product of greatest diameters (SPD) also decreases more rapidly during treatment with the BTK inhibitor than with the BTK inhibitor ibrutinib.
Figure 3:
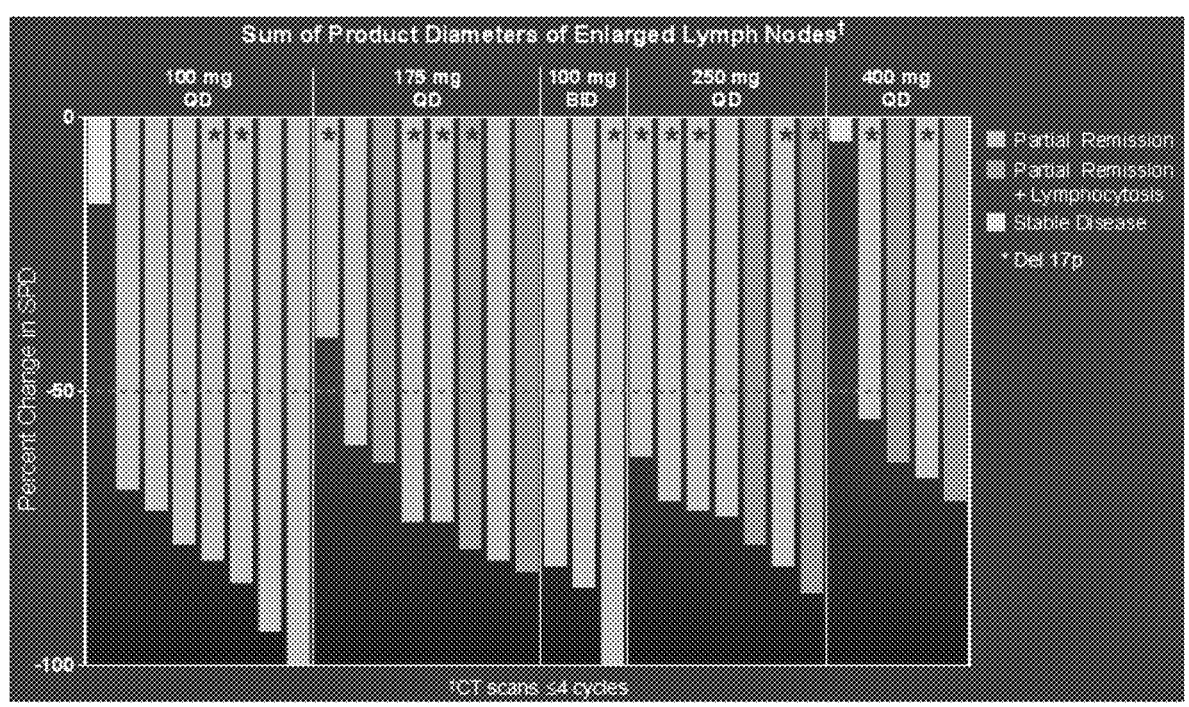
FIG. 3 shows overall response data shown by SPD of enlarged lymph nodes in CLL patients as a function of dose of the BTK inhibitor of Formula (II).

FIG. 2 shows the median % change in ALC and SPD from baseline in the clinical study of Formula (II), plotted in comparison to the results reported for ibrutinib in FIG. 1A of J. C. Byrd, et al., N. Engl. J. Med 2013, 369, 32-42. The results show that Formula (II) leads to a more rapid patient response in CLL than corresponding treatment with ibrutinib. This effect is illustrated, for example, by the median % change in SPD, which achieved the same status in the present study at 7 months of treatment with Formula (II) as compared to 18 months for ibrutinib. The % change in SPD observed in the different cohorts (i.e. by dose and dosing regimen) is shown in FIG. 3, and in all cases shows significant responses.

Figure 4:
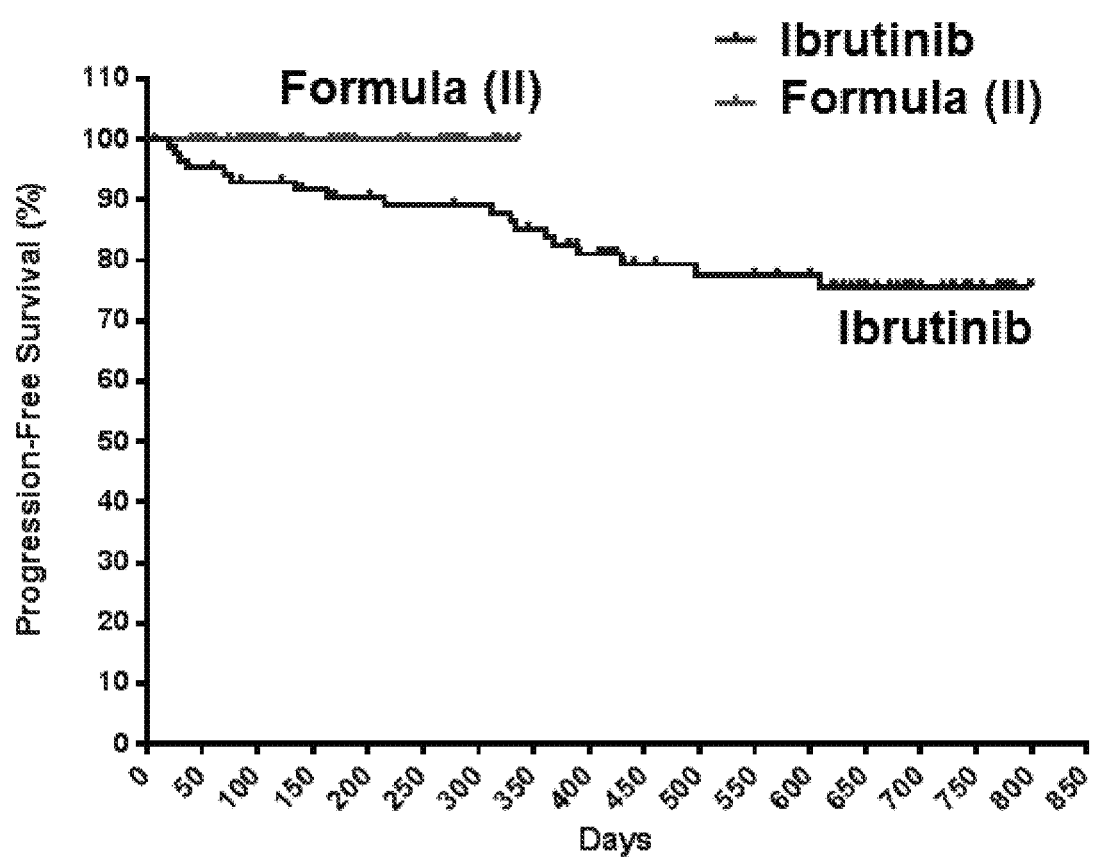
FIG. 4 shows a comparison of progression-free survival (PFS) in CLL patients treated with the BTK inhibitor ibrutinib or the BTK inhibitor of Formula (II). The ibrutinib data is taken from J. C. Byrd, et al., *N. Engl. J. Med.* 2013, 369, 32-42. CLL patients treated with Formula (II) for at least 8 days are included.
Figure 5:
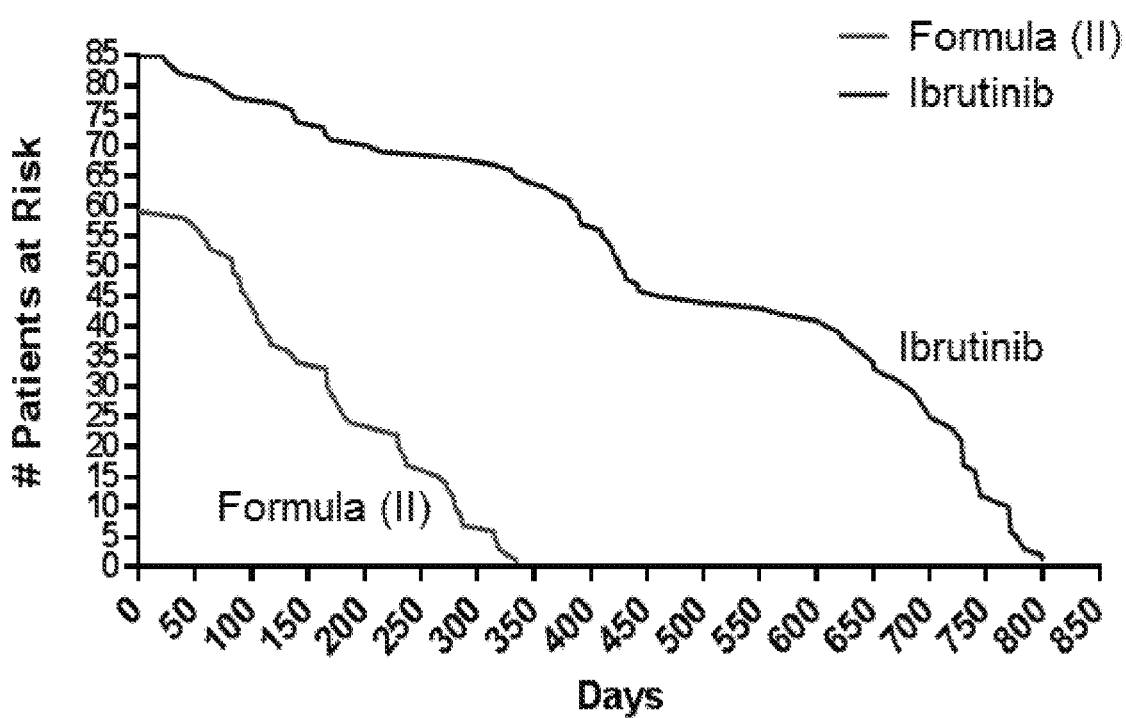
FIG. 5 shows a comparison of number of patients at risk in CLL patients treated with the BTK inhibitor ibrutinib or the BTK inhibitor of Formula (II). CLL patients treated with Formula (II) for at least 8 days are included.

A Kaplan-Meier curve showing PFS from the clinical CLL study of Formula (II) is shown in FIG. 4. A comparison of survival curves was performed using the Log-Rank (Mantle-Cox) test, with a p-value of 0.0206 indicating that the survival curves are different. The number of patients at risk is shown in FIG. 5. Both FIG. 4 and FIG. 5 show the results for Formula (II) in comparison to the results reported for ibrutinib in J. C. Byrd, et al., N. Engl. J. Med 2013, 369, 32-42. An improvement in survival and a reduction in risk are observed in CLL patients treated with Formula (II) in comparison to patients treated with ibrutinib.

Based on the data and comparisons shown in FIG. 2 to FIG. 5, the CLL study with Formula (II) showed that the efficacy of Formula (II) was surprisingly superior to that of ibrutinib.

Figure 6:
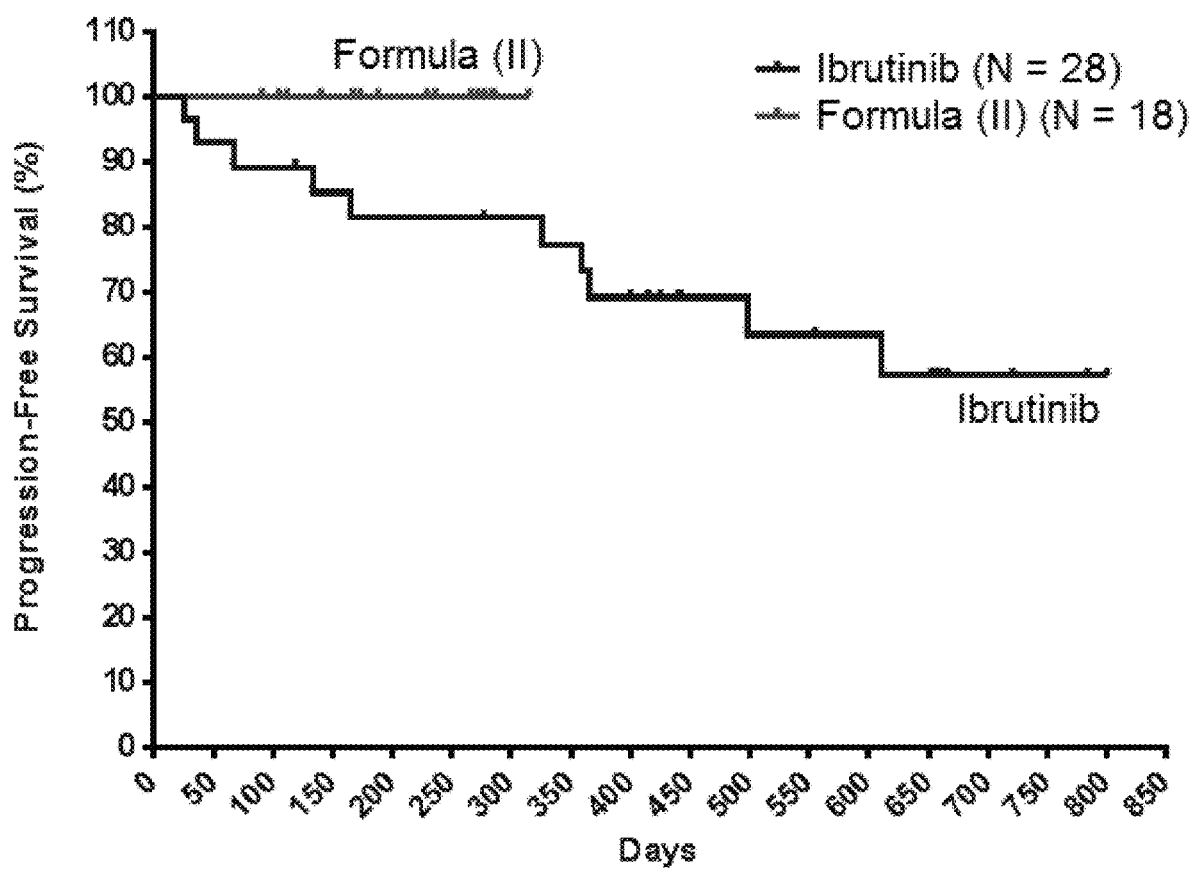
FIG. 6 shows a comparison of progression-free survival (PFS) in CLL patients exhibiting the 17p deletion and treated with the BTK inhibitor ibrutinib or the BTK inhibitor of Formula (II). The ibrutinib data is taken from J. C. Byrd, et al., *N. Engl. J. Med.* 2013, 369, 32-42.
Figure 7:
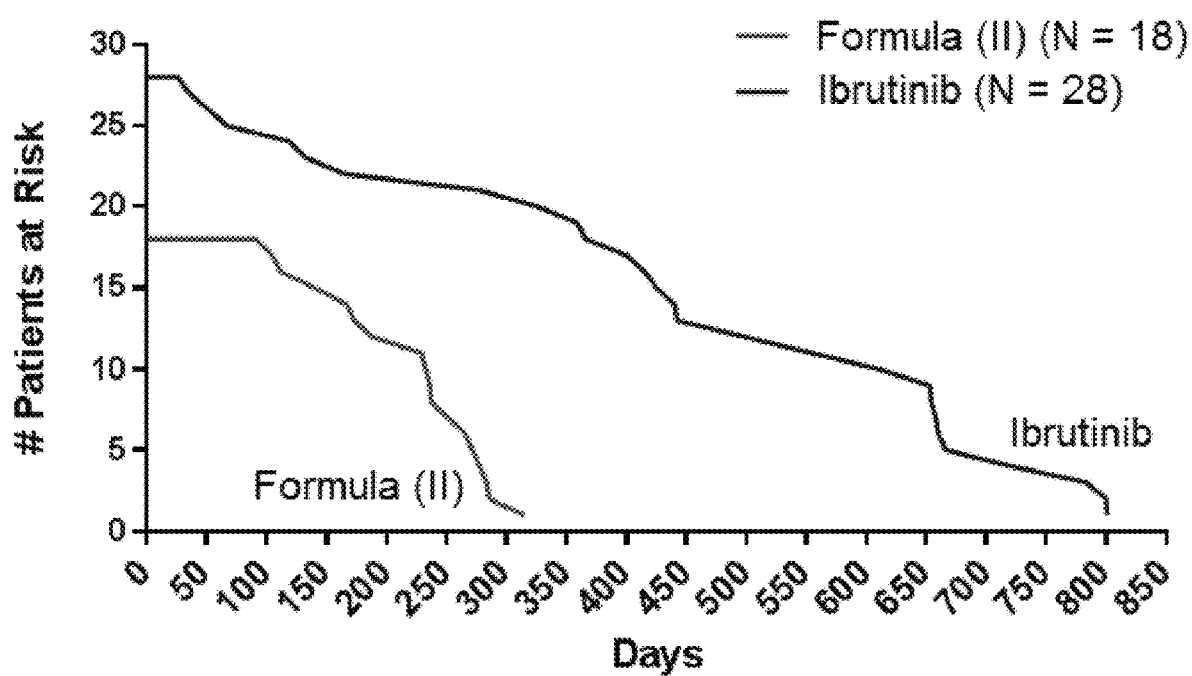
FIG. 7 shows a comparison of number of patients at risk in CLL patients exhibiting the 17p deletion and treated with the BTK inhibitor ibrutinib or the BTK inhibitor of Formula (II). The ibrutinib data is taken from J. C. Byrd, et al., N. Engl. J. Med. 2013, 369, 32-42. CLL patients treated with Formula (II) for at least 8 days are included.

In the literature study of ibrutinib, increased disease progression was associated with patients with high-risk cytogenetic lesions (17p13.1 deletion or 11q22.3 deletion), as shown in FIG. 3A in J. C. Byrd, et al., N. Engl. J. Med 2013, 369, 32-42, which shows ibrutinib PFS including PFS broken down by genetic abnormality. The 17p and 11q deletions are validated high-risk characteristics of CLL, and the 17p deletion is the highest risk. In FIG. 6, the PFS is shown for Formula (II) in patients with the 17p deletion in comparison to the results obtained for ibrutinib in J. C. Byrd, et al., N. Engl. J. Med 2013, 369, 32-42. A p-value of 0.0696 was obtained. In FIG. 7, the number of patients at risk with the 17p deletion is compared. To date, no 17p patients have progressed on Formula (II).

The adverse events observed in the clinical study in relapsed/refractory CLL are given in Table 6. No DLTs were observed. The MTD was not reached. No treatment-related serious adverse events (SAEs) were observed. No prophylactic antivirals or antibiotics were needed.

TABLE 6

Treatment-related adverse events reported in the clinical study of Formula (II) in relapsed/refractory CLL. (Reported in >5% of patients.)

| Adverse Events (Treatment-Related), n (%) | Grade | All (N = 44) |
|---|---|---|
| Headache | ½ | 7 (16) |
| Increased tendency to bruise | 1 | 6 (14) |
| Diarrhea | 1 | 4 (9) |
| Petechiae | 1 | 3 (7) |

The clinical study of Formula (II) thus showed other unexpectedly superior results compared to ibrutinib therapy. A lack of lymphocytosis was observed in the study. Furthermore, only grade 1 AEs were observed, and these AEs were attributable to the high BTK selectivity of Formula (II).

Figure 8:
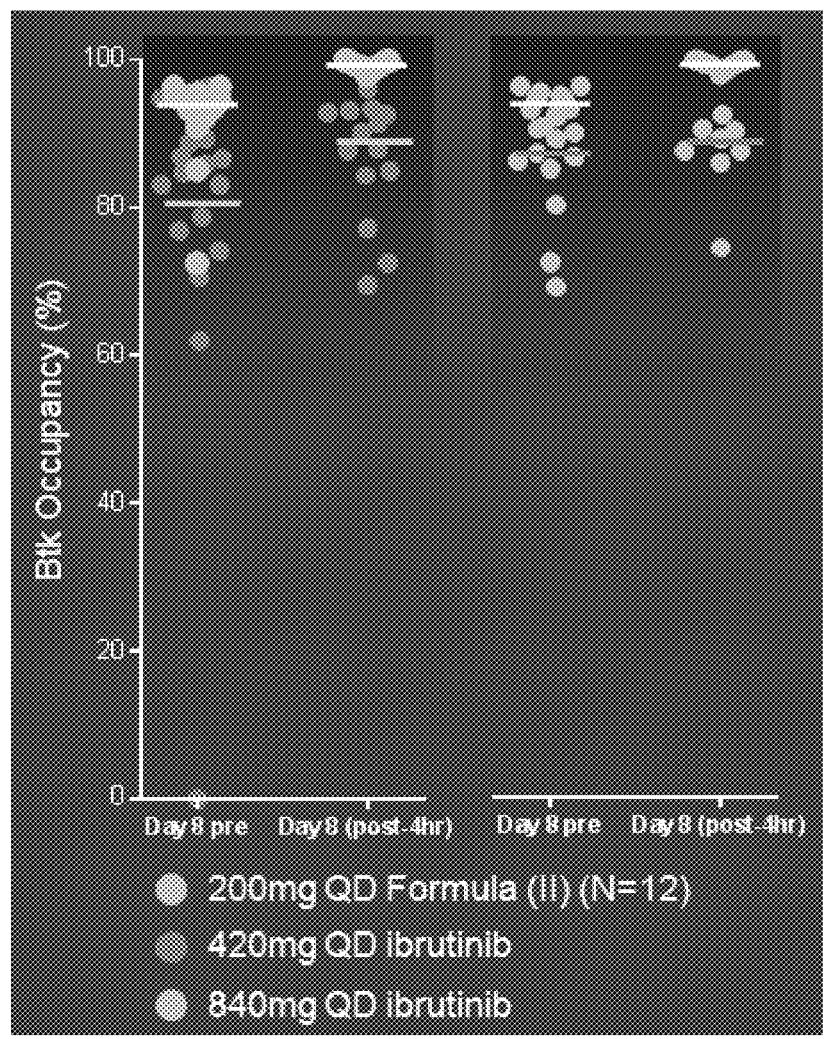
FIG. 8 shows improved BTK target occupancy of Formula (II) at lower dosage versus ibrutinib in relapsed/refractory CLL patients.

BTK target occupancy was measured for relapsed/refractory CLL patients with the results shown in FIG. 8. For 200 mg QD dosing of the BTK inhibitor of Formula (II), approximately 94%-99% BTK occupancy was observed, with superior 24 hour coverage and less inter-patient variability also observed. For 420 mg and 840 mg QD of the BTK inhibitor ibrutinib, 80%-90% BTK occupancy was observed, with more inter-patient variability and capped occupancy. These results indicate that the BTK inhibitor of Formula (II) achieves superior BTK occupancy in CLL patients than ibrutinib.

Figure 9:
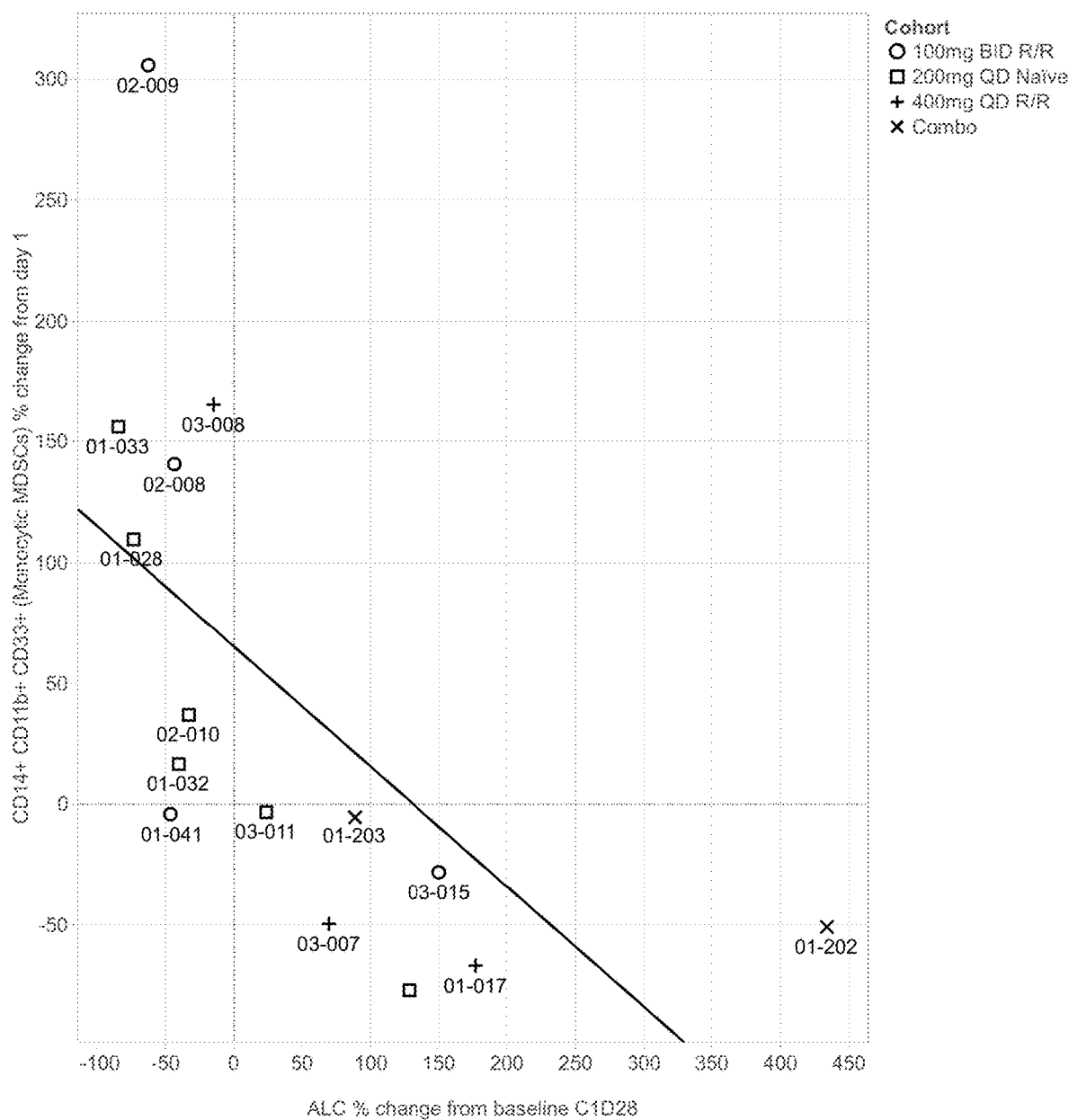
FIG. 9 shows the % change in myeloid-derived suppressor cell (MDSC) (monocytic) level over 28 days versus % ALC change at Cycle 1, day 28 (C1D28) with trendlines.
Figure 10:
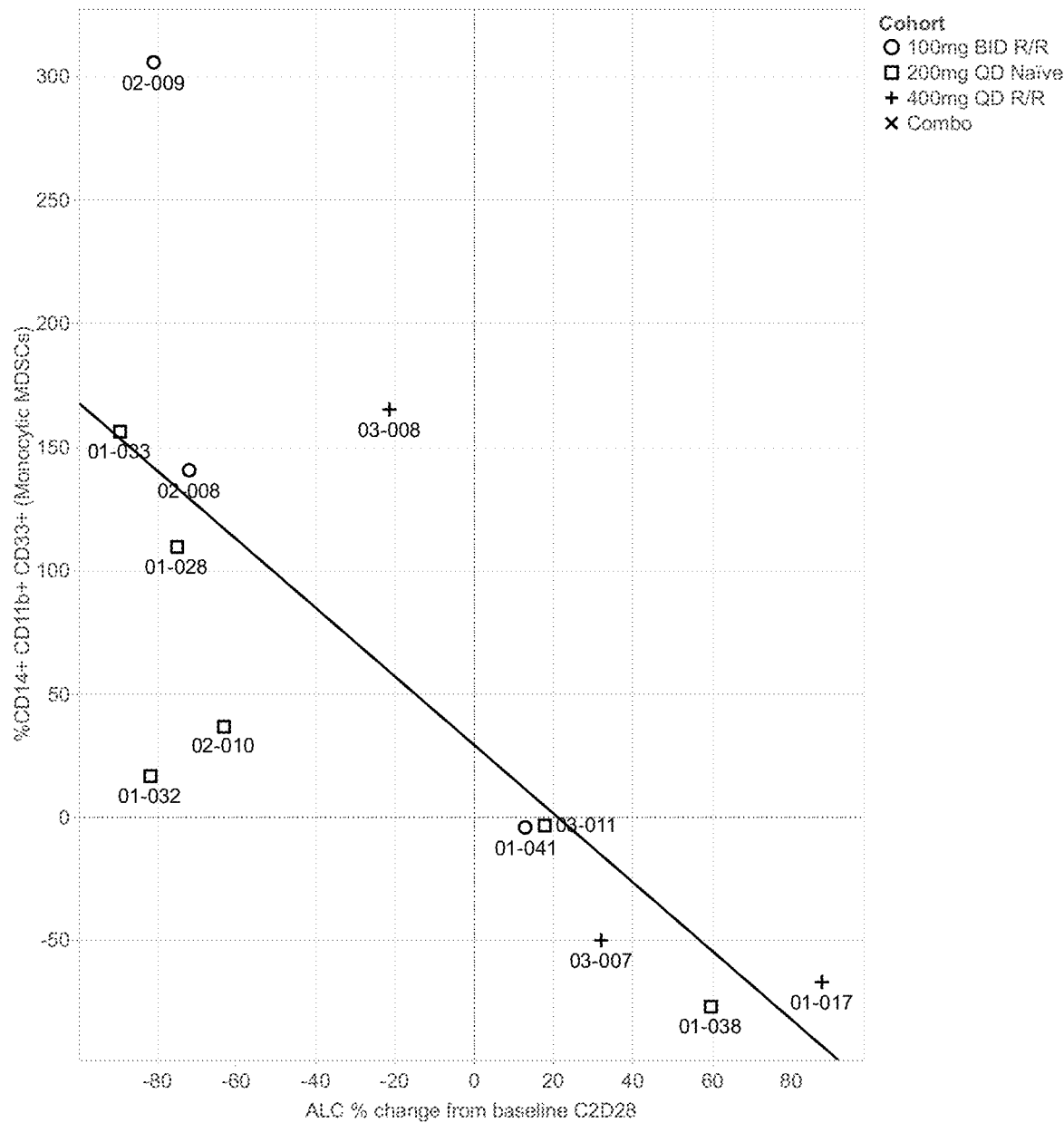
FIG. 10 shows the % change in MDSC (monocytic) level over 28 days versus % ALC change at Cycle 2, day 28 (C2D28) with trendlines.
Figure 11:
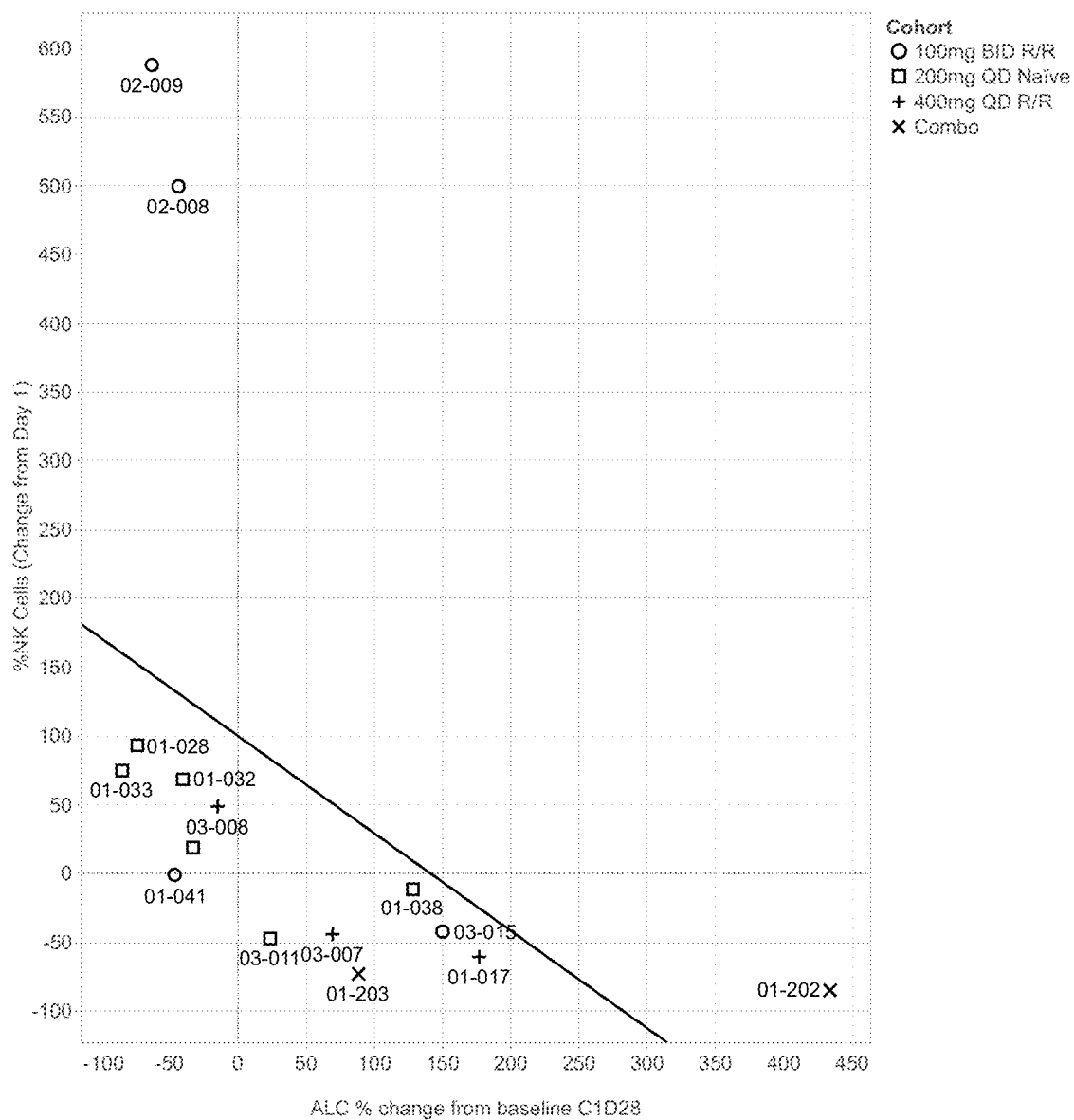
FIG. 11 shows the % change in natural killer (NK) cell level over 28 days versus % ALC change at Cycle 1, day 28 (C2D28) with trendlines.
Figure 12:
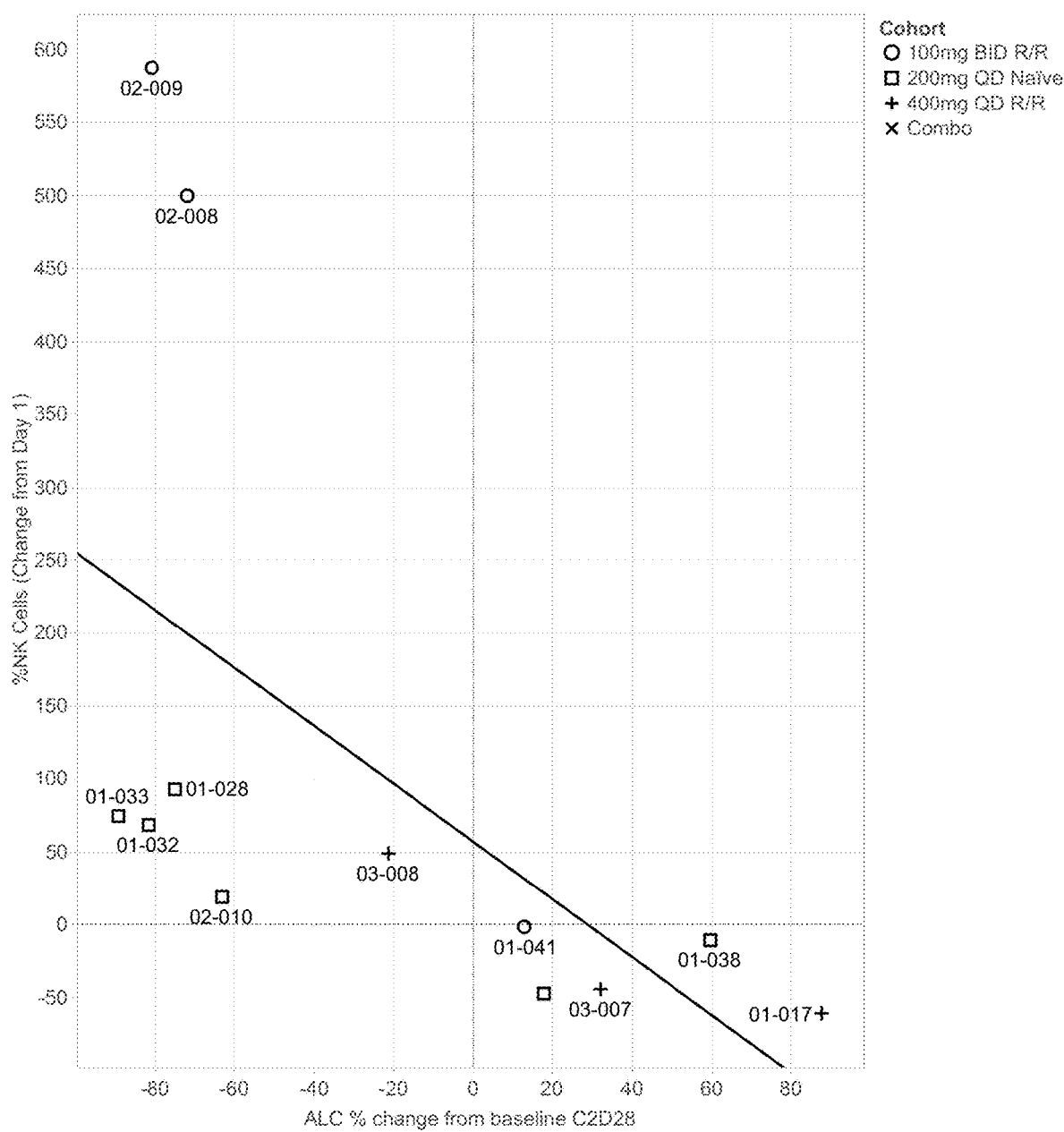
FIG. 12 shows the % change in NK cell level over 28 days versus % ALC change at Cycle 2, day 28 (C2D28) with trendlines.
Figure 13:
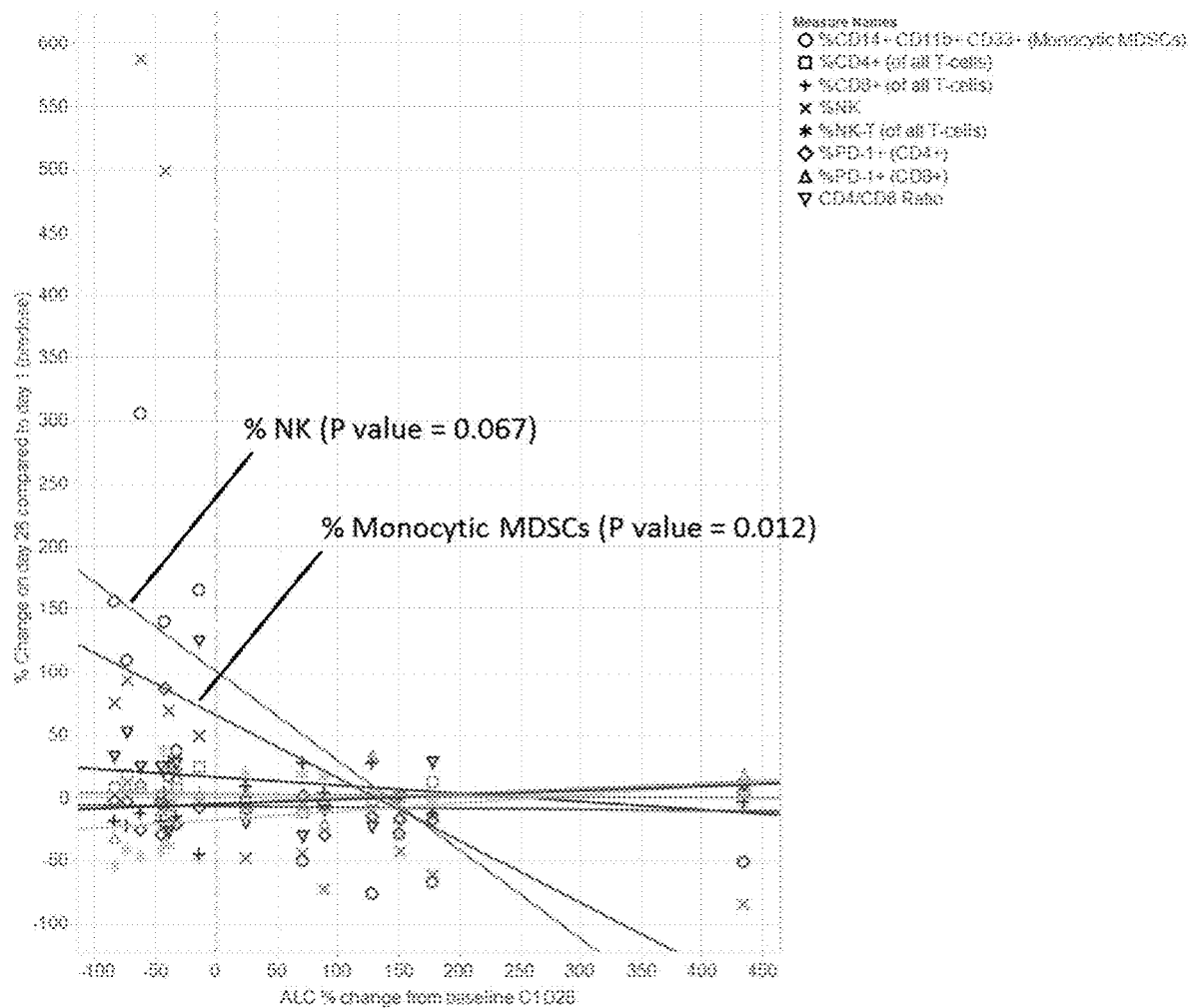
FIG. 13 compares the % change in MDSC (monocytic) level and % change in NK cell level over 28 days versus % ALC change with the % change in level of $CD4^+$ T cells, $CD8^+$ T cells, $CD4^+/CD8^+$ T cell ratio, NK-T cells, $PD-1^+$ $CD4^+$ T cells, and $PD-1^+$ $CD8^+$ T cells, also versus % ALC change, at Cycle 1 day 28 (C1D28). Trendlines are shown for % change in MDSC (monocytic) level and % change in NK cell level.
Figure 14:
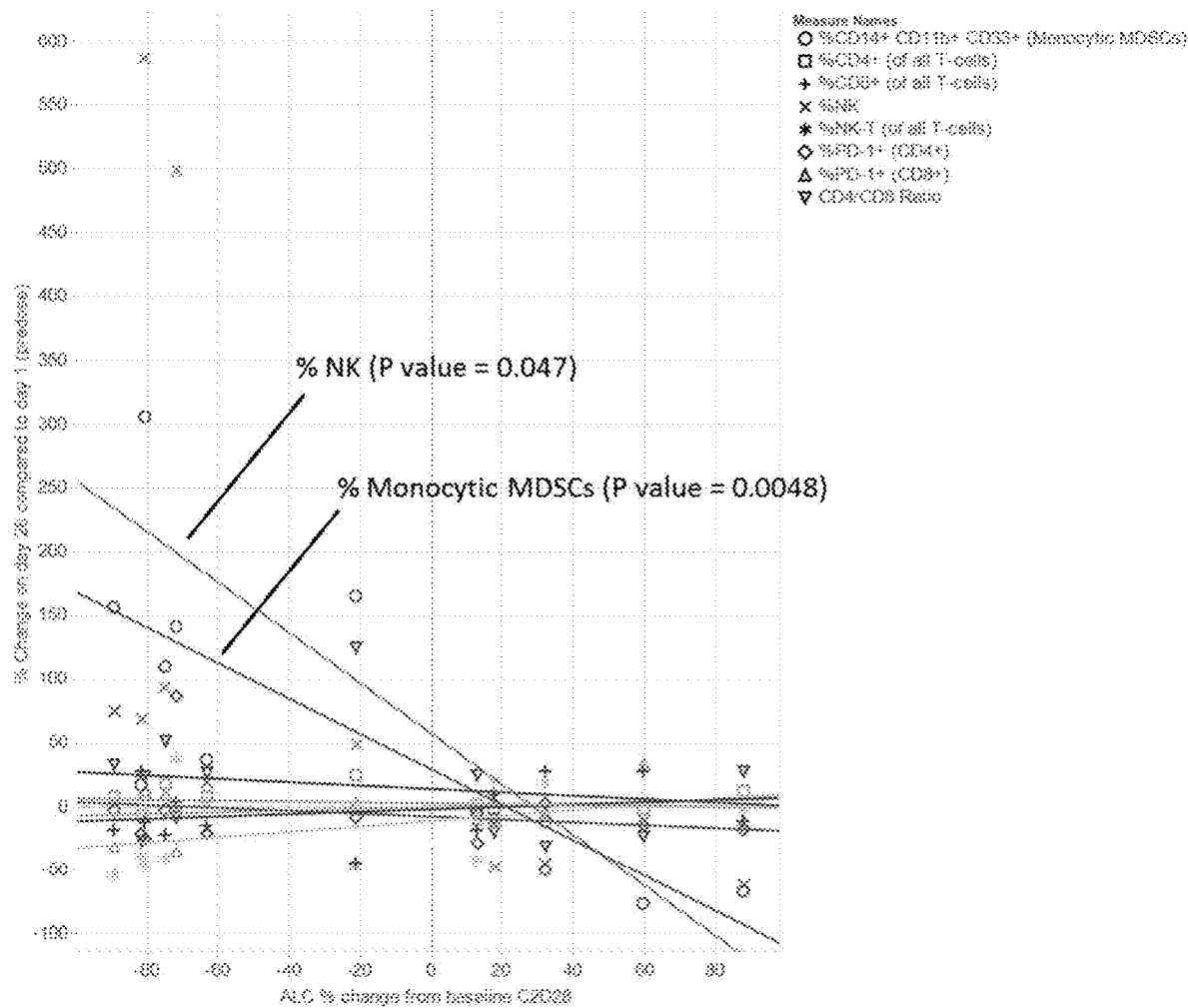
FIG. 14 compares the % change in MDSC (monocytic) level and % change in NK cell level over 28 days versus % ALC change with the % change in level of $CD4^+$ T cells, $CD8^+$ T cells, $CD4^+/CD8^+$ T cell ratio, NK-T cells, $PD-1^+$ $CD4^+$ T cells, and $PD-1^+$ $CD8^+$ T cells, also versus % ALC change, at Cycle 2 day 28 (C2D28). Trendlines are shown for % change in MDSC (monocytic) level and % change in NK cell level.
Figure 15:
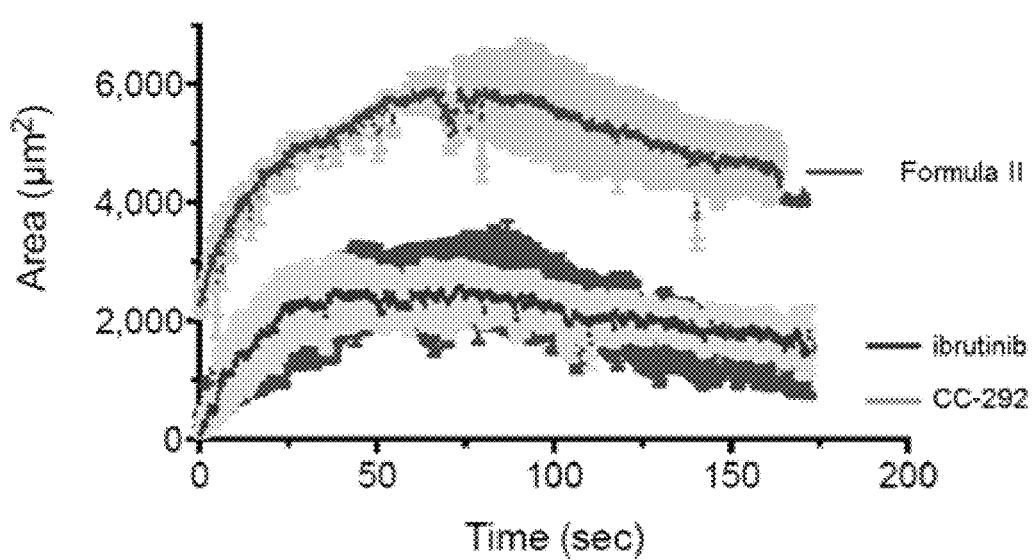
FIG. 15 illustrates a quantitative comparison obtained by in vivo analysis of early thrombus dynamics in a humanized mouse laser injury model using three BTK inhibitors at a concentration of 1 µM.

The effects of Formula (II) on cell subset percentages were also evaluated using flow cytometry analysis of peripheral blood, with the results shown in FIG. 9, FIG. 10, FIG. 11, FIG. 12, FIG. 13, and FIG. 14. PBMC samples from CLL patient samples drawn prior to (predose) and after 28 days of dosing with Formula (II) were compared for potential changes in cell subsets. PBMCs were stained with monoclonal antibodies conjugated to fluorescent tags (fluorochromes) to identify cell subsets via flow cytometry. Non-viable cells were excluded from the analysis using the dye 7-aminoactinomycin D (7-AAD). To produce the metric of percent change, the following steps were taken. First, each cell subset was defined by hierarchical flow cytometry gating. Then, the change in frequency (between day 1 and day 28) was calculated for each cell subset. MDSC subsets were measured as a % of all myeloid cells. T cell subsets were measured as a % of all $CD3^+$ cells, and NK cells were measured as a % of all live $CD45^+$ cells. In FIG. 9 and FIG. 10, the results show the % change in MDSC (monocytic) level over 28 days versus % ALC change at cycle 1 day 28 (C1D28) and at cycle 2 day 28 (C2D28). A cycle is 28 days. A trend is observed wherein patients with decreasing ALC % had increasing MDSC (monocytic) %. This may include patients who had quickly resolving lymphocytosis and those with no initial lymphocytosis. This provides evidence that treatment with Formula (II) mobilizes MDSCs and thus affects the CLL tumor microenvironment in marrow and lymph nodes, which is an unexpected indication of superior efficacy. In FIG. 11 and FIG. 12, the results show the % change in NK cell level over 28 days versus % ALC change, measured at C1D28 or C2D28, and similar trends are observed wherein patients with decreasing ALC % had increasing NK cell %. This may include patients who had quickly resolving lymphocytosis and those having no initial lymphocytosis. The effects in FIG. 9 to FIG. 12 are observed in multiple cohorts, at doses including 100 mg BID, 200 mg QD, and 400 mg QD. In FIG. 13 and FIG. 14, the effects on NK cells and MDSC cells are compared to a number of other markers versus % change in ALC at C1D28 and C2D28. These other markers include CD4+ T cells, CD8+ T cells, CD4+/CD8+ T cell ratio, NK-T cells, PD-1+ CD4+ T cells, and PD-1+ CD8+ T cells. The effects on NK cells and MDSC cells are observed to be much more pronounced than on any of these other markers.

These results suggest that after Formula (II) administration, the CLL microenvironment undergoes a change wherein NK cells and monocytic MDSC subsets increase in frequency in the peripheral blood in patients with falling ALC counts, an important clinical parameter in CLL. The NK cell increase may reflect an overall increase in cytolytic activity against B-CLL resulting in the ALC % to drop. The increase in MDSC % in the blood may be due to a movement of these cells out of the lymph nodes, spleen, and bone marrow, which are all possible sites of CLL proliferation. Fewer MDSCs at the CLL proliferation centers would likely result in a reduced immunosuppressive microenvironment leading to an increase in cell-mediated immunity against the tumor, decreased tumor proliferation, and eventually lower ALC % in the circulation.

Overall, Formula (II) shows superior efficacy as measured by ALC than first generation BTK inhibitors such as ibrutinib, or PI3K-δ inhibitors such as idelalisib. Formula (II) has better target occupancy and better pharmacokinetic and metabolic parameters than ibrutinib, leading to improved B cell apoptosis. Furthermore, unlike treatment with ibrutinib and PI3K-δ inhibitors, treatment with Formula (II) does not affect NK cell function. Finally, treatment with Formula (II) leads to a CLL tumor microenvironmental effect by excluding MDSC cells from the marrow and lymph nodes and reducing their number.

Example 3—Effects of BTK Inhibitors on Thrombosis

Clinical studies have shown that targeting the BCR signaling pathway by inhibiting BTK produces significant clinical benefit (J. C. Byrd, et al., *N. Engl. J. Med.* 2013, 369, 32-42; M. L. Wang, et al., *N. Engl. J. Med.* 2013, 369, 507-16). However, in these studies, bleeding has been reported in up to 50% of ibrutinib-treated patients. Most bleeding events were of grade 1-2 (spontaneous bruising or petechiae) but, in 5% of patients, they were of grade 3 or higher after trauma. These results are reflected in the prescribing information for ibrutinib, where bleeding events of any grade, including bruising and petechiae, were reported in approximately half of patients treated with ibrutinib (IMBRUVICA package insert and prescribing information, revised July 2014, U.S. Food and Drug Administration).

Constitutive or aberrant activation of the BCR signaling cascade has been implicated in the propagation and maintenance of a variety of B cell malignancies. Small molecule inhibitors of BTK, a protein early in this cascade and specifically expressed in B cells, have emerged as a new class of targeted agents. There are several BTK inhibitors, including CC-292 and ibrutinib (PCI-32765), in clinical development. CC-292 refers to (N-(3-((5-fluoro-2-((4-(2-methoxyethoxy)phenyl)amino)pyrimidin-4-yl)amino)phenyl)acrylamide, or a pharmaceutically acceptable salt thereof, including a hydrochloride salt or besylate salt thereof. Importantly, early stage clinical trials have found ibrutinib to be particularly active in chronic lymphocytic leukemia (CLL) and mantle cell lymphoma (MCL), suggesting that this class of inhibitors may play a significant role in various types of cancers (Aalipour and Advani, *Br. J. Haematol.* 2013, 163, 436-43). However, their effects are not limited to leukemia or lymphomas as platelets also rely on the Tec kinases family members BTK and Tec for signal transduction in response to various thrombogenic stimuli (Oda, et al., *Blood* 2000, 95(5), 1663-70; Atkinson, et al. *Blood* 2003, 102(10), 3592-99). In fact, both Tec and BTK play an important role in the regulation of phospholipase Cγ2 (PLCγ2) downstream of GPVI in human platelets. In addition, BTK is activated and undergoes tyrosine phosphorylation upon challenge of the platelet thrombin receptor, which requires the engagement of αIIbβ3 integrin and PI3K activity (Laffargue, et al., *FEBS Lett.* 1999, 443(1), 66-70). It has also been implicated in GPIbα-dependent thrombus stability at sites of vascular injury (Liu, et al., *Blood* 2006, 108(8), 2596-603). Thus, BTK and Tec are involved in several processes important in supporting the formation of a stable hemostatic plug, which is critical for preventing significant blood loss in response to vascular injury. Hence, the effects of the BTK inhibitor of Formula (II) and ibrutinib were evaluated on human platelet-mediated thrombosis by utilizing the in vivo human thrombus formation in the VWF HA1 mice model described in Chen, et al. *Nat. Biotechnol.* 2008, 26(1), 114-19.

Administration of anesthesia, insertion of venous and arterial catheters, fluorescent labeling and administration of human platelets ($5 \times 10^8$/ml), and surgical preparation of the cremaster muscle in mice have been previously described (Chen, et al., *Nat Biotechnol.* 2008, 26(1), 114-19). Injury to the vessel wall of arterioles (~40-65 mm diameter) was performed using a pulsed nitrogen dye laser (440 nm, Photonic Instruments) applied through a 20× water-immersion Olympus objective (LUMPlanFl, 0.5 numerical aperture (NA)) of a Zeiss Axiotech vario microscope. Human platelet and wall interactions were visualized by fluorescence microscopy using a system equipped with a Yokogawa CSU-22 spinning disk confocal scanner, iXON EM camera, and 488 nm and 561 nm laser lines to detect BCECF-labeled and rhodamine-labeled platelets, respectively (Revolution XD, Andor Technology). The extent of thrombus formation was assessed for 2 minutes after injury and the area ($\mu m^2$) of coverage determined (Image IQ, Andor Technology). For the Formula (II), CC-292, ibrutinib inhibition studies, the BTK inhibitors were added to purified human platelets for 30 minutes before administration.

The in vivo thrombus effects of the BTK inhibitors, Formula (II), CC-292, and ibrutinib, were evaluated on human platelet-mediated thrombosis by utilizing the in vivo human thrombus formation in the VWF HA1 mice model, which has been previously described (Chen, et al., *Nat Biotechnol.* 2008, 26(1), 114-19). Purified human platelets were preincubated with various concentrations of the BTK inhibitors (0.1 µM, 0.5 µM, or 1 µM) or DMSO and then administered to VWF HA1 mice, followed by laser-induced thrombus formation. The BTK inhibitor-treated human platelets were fluorescently labeled and infused continuously through a catheter inserted into the femoral artery. Their behavior in response to laser-induced vascular injury was monitored in real time using two-channel confocal intravital microscopy (Furie and Furie, *J. Clin. Invest.* 2005, 115(12), 2255-62).

The objective of this study was to evaluate in vivo thrombus formation in the presence of BTK inhibitors. In vivo testing of novel antiplatelet agents requires informative biomarkers. By utilizing a genetic modified mouse von Willebrand factor (VWFR1326H) model that supports human but not mouse platelet-mediated thrombosis, we evaluated the effects of Formula (II), CC-292, and ibrutinib on thrombus formation. These results show that Formula (II) had no significant effect on human platelet-mediated thrombus formation while ibrutinib was able to limit this process, resulting in a reduction in maximal thrombus size by 61% compared with control. CC-292 showed an effect similar to ibrutinib. These results, which show reduced thrombus formation for ibrutinib at physiologically relevant concentrations, may provide some mechanistic background for the Grade ≥3 bleeding events (eg, subdural hematoma, gastrointestinal bleeding, hematuria and postprocedural hemorrhage) that have been reported in ≤6% of patients treated with ibrutinib.

GPVI platelet aggregation was measured for Formula (II) and ibrutinib. Blood was obtained from untreated humans, and platelets were purified from plasma-rich protein by centrifugation. Cells were resuspended to a final concentration of 350,000/µL in buffer containing 145 mmol/µL NaCl, 10 mmol/µL HEPES, 0.5 mmol/µL $Na_2HPO_4$, 5 mmol/µL KCl, 2 mmol/µL $MgCl_2$, 1 mmol/µL $CaCl_2$), and 0.1% glucose, at pH 7.4. Stock solutions of Convulxin (CVX) GPVI were prepared on the day of experimentation and added to platelet suspensions 5 minutes (37° C., 1200 rpm) before the induction of aggregation. Aggregation was assessed with a Chronolog Lumi-Aggregometer (model 540 VS; Chronolog, Havertown, Pa.) and permitted to proceed for 6 minutes after the addition of agonist. The results are reported as maximum percent change in light transmittance from baseline with platelet buffer used as a reference. The results are shown in FIG. 16.

Figure 17:
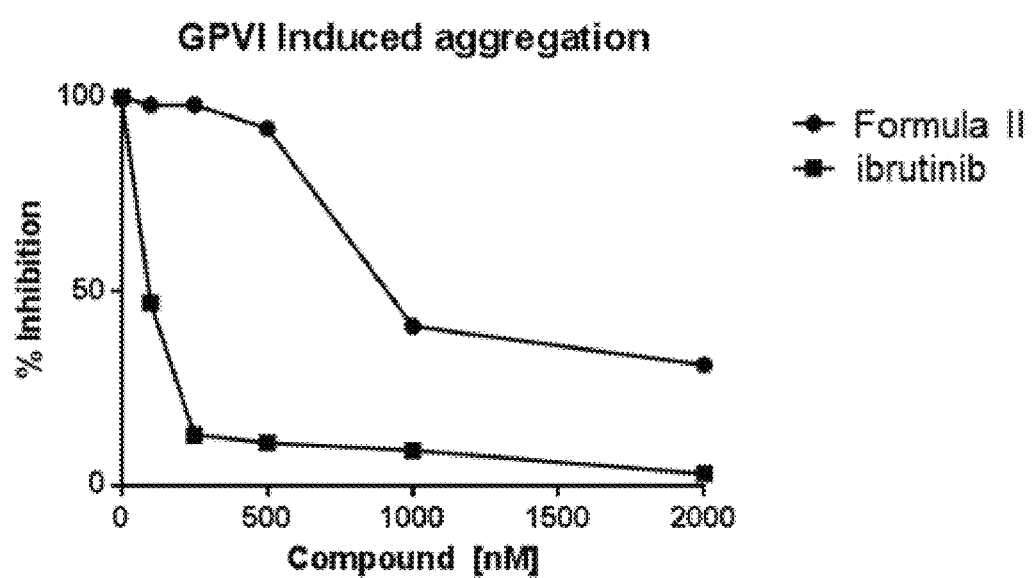
FIG. 17 illustrates the results of GPVI platelet aggregation studies of Formula (II) and ibrutinib.

In FIG. 17, the results of CVX-induced (250 ng/mL) human platelet aggregation results before and 15 minutes after administration of the BTK inhibitors to 6 healthy individuals are shown.

Figure 16:
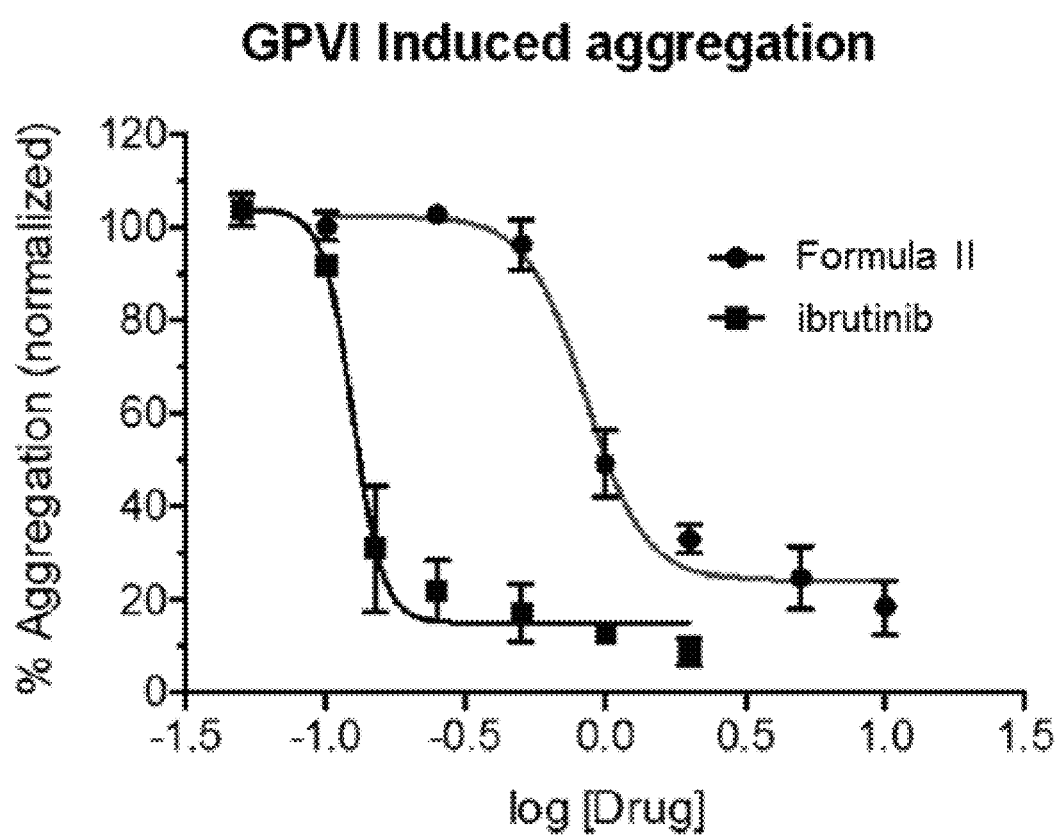
FIG. 16 illustrates the results of platelet collagen receptor glycoprotein VI (GPVI) platelet aggregation studies of Formula (II) ($IC_{50}$=1.15 µM) and ibrutinib ($IC_{50}$=0.13 µM).

The results depicted in FIG. 16 and FIG. 17 indicate that the BTK inhibitor ibrutinib significantly inhibits GPVI platelet aggregation, while the BTK inhibitor of Formula (II) does not, further illustrating the surprising benefits of the latter compound.

---

We claim:

1. A method of treating chronic lymphocytic leukemia (CLL) in a human subject suffering therefrom, comprising: orally administering to the human subject a dose of 100 mg twice daily of a Bruton's tyrosine kinase (BTK) inhibitor, wherein the BTK inhibitor is a compound of Formula (II):

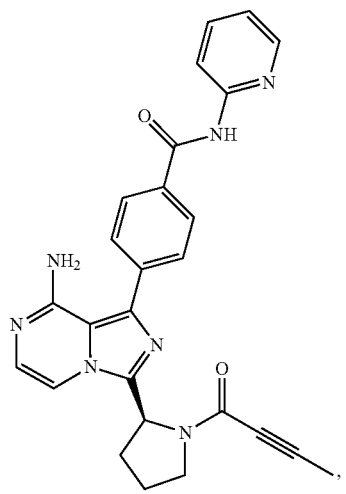

or a pharmaceutically acceptable salt thereof; and intravenously administering obinutuzumab to the human subject.

2. The method of claim 1, wherein the BTK inhibitor is administered before obinutuzumab.

3. The method of claim 1, wherein the BTK inhibitor is administered after obinutuzumab.

4. The method of claim 1, wherein obinutuzumab is administered at a dose selected from the group consisting of about 100 mg, about 200 mg, about 300 mg, about 400 mg, about 500 mg, about 600 mg, about 700 mg, about 800 mg, about 900 mg, about 1000 mg, about 1100 mg, about 1200 mg, about 1300 mg, about 1400 mg, about 1500 mg, about 1600 mg, about 1700 mg, about 1800 mg, about 1900 mg, and about 2000 mg.

5. The method of claim 1, wherein the obinutuzumab is administered at a dose of 100 mg.

6. The method of claim 1, wherein the obinutuzumab is administered at a dose of 900 mg.

7. The method of claim 1, wherein the obinutuzumab is administered at a dose of 1000 mg.

8. The method of claim 1, wherein the BTK inhibitor is administered to the human subject for a period selected from the group consisting of about 8 days, about 14 days, about 28 days, and about 56 days.

9. The method of claim 1, wherein the BTK inhibitor is the compound of Formula (II):

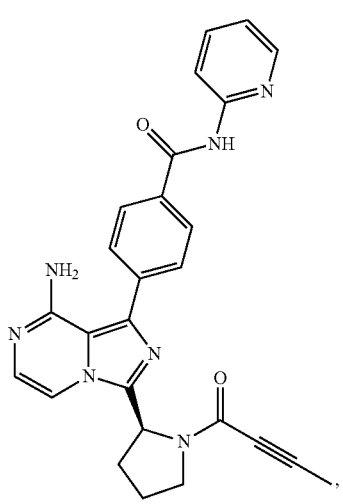

administered to the human subject.

10. The method of claim 1, wherein the BTK inhibitor is the pharmaceutically acceptable salt of the compound of Formula (II):
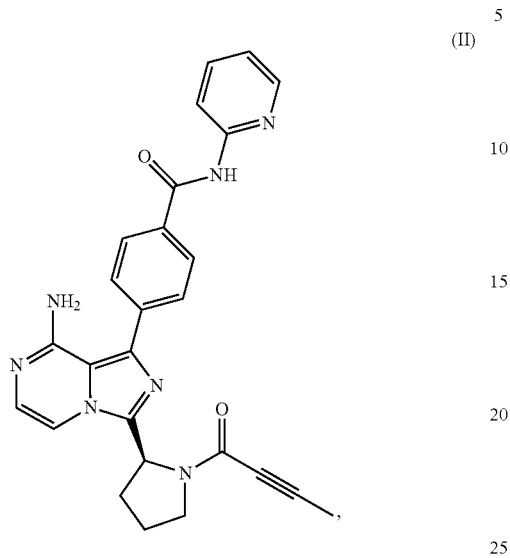
(II)
administered to the human subject.
11. The method of claim 1, wherein the BTK inhibitor is administered at an interval of about twelve hours.
12. The method of claim 1, wherein the human subject has a 17p13.1 (17p) deletion.
* * * * *

UNITED STATES PATENT AND TRADEMARK OFFICE
CERTIFICATE OF CORRECTION

| | | |
|---|---|---|
| PATENT NO. | : 11,771,696 B2 | Page 1 of 1 |
| APPLICATION NO. | : 17/370778 | |
| DATED | : October 3, 2023 | |
| INVENTOR(S) | : Ahmed Hamdy et al. | |

It is certified that error appears in the above-identified patent and that said Letters Patent is hereby corrected as shown below:

In the Specification

Please insert the following paragraph after the title.
--The subject matter disclosed herein was developed and the claimed invention was made by or on behalf of the following parties to a joint research agreement: Covalution Pharma B.V. (a/k/a Acerta Pharma B.V.) and MSD Oss B.V. (a predecessor-in-interest to Merck Sharp & Dohme B.V.).--

Signed and Sealed this
Twenty-sixth Day of March, 2024

*Katherine Kelly Vidal*

Katherine Kelly Vidal
*Director of the United States Patent and Trademark Office*

SEQUENCE LISTING

```
<160> NUMBER OF SEQ ID NOS: 14

<210> SEQ ID NO 1
<211> LENGTH: 451
<212> TYPE: PRT
<213> ORGANISM: Artificial Sequence
<220> FEATURE:
<223> OTHER INFORMATION: Heavy chain amino acid sequence of the anti-
      CD20 monoclonal antibody rituximab.

<400> SEQUENCE: 1

Gln Val Gln Leu Gln Gln Pro Gly Ala Glu Leu Val Lys Pro Gly Ala
1               5                   10                  15

Ser Val Lys Met Ser Cys Lys Ala Ser Gly Tyr Thr Phe Thr Ser Tyr
                20                  25                  30

Asn Met His Trp Val Lys Gln Thr Pro Gly Arg Gly Leu Glu Trp Ile
            35                  40                  45

Gly Ala Ile Tyr Pro Gly Asn Gly Asp Thr Ser Tyr Asn Gln Lys Phe
        50                  55                  60

Lys Gly Lys Ala Thr Leu Thr Ala Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95
```

Ala Arg Ser Thr Tyr Tyr Gly Gly Asp Trp Tyr Phe Asn Val Trp Gly
              100                 105                 110

Ala Gly Thr Thr Val Thr Val Ser Ala Ala Ser Thr Lys Gly Pro Ser
        115                 120                 125

Val Phe Pro Leu Ala Pro Ser Ser Lys Ser Thr Ser Gly Gly Thr Ala
130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365

Leu Thr Cys Leu Val Lys Gly Phe Tyr Pro Ser Asp Ile Ala Val Glu
370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450

<210> SEQ ID NO 2
<211> LENGTH: 213
<212> TYPE: PRT
<213> ORGANISM: Artificial sequence
<220> FEATURE:
<223> OTHER INFORMATION: Light chain amino acid sequence of the anti-
      CD20 monoclonal antibody rituximab.

<400> SEQUENCE: 2

```
Gln Ile Val Leu Ser Gln Ser Pro Ala Ile Leu Ser Ala Ser Pro Gly
1               5                   10                  15

Glu Lys Val Thr Met Thr Cys Arg Ala Ser Ser Ser Val Ser Tyr Ile
            20                  25                  30

His Trp Phe Gln Gln Lys Pro Gly Ser Ser Pro Lys Pro Trp Ile Tyr
        35                  40                  45

Ala Thr Ser Asn Leu Ala Ser Gly Val Pro Val Arg Phe Ser Gly Ser
    50                  55                  60

Gly Ser Gly Thr Ser Tyr Ser Leu Thr Ile Ser Arg Val Glu Ala Glu
65                  70                  75                  80

Asp Ala Ala Thr Tyr Tyr Cys Gln Gln Trp Thr Ser Asn Pro Pro Thr
                85                  90                  95

Phe Gly Gly Gly Thr Lys Leu Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 3
<211> LENGTH: 449
<212> TYPE: PRT
<213> ORGANISM: Artificial sequence
<220> FEATURE:
<223> OTHER INFORMATION: Heavy chain amino acid sequence of the anti-
      CD20 monoclonal antibody obinutuzumab.

<400> SEQUENCE: 3

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ala Phe Ser Tyr Ser
            20                  25                  30

Trp Ile Asn Trp Val Arg Gln Ala Pro Gly Gln Gly Leu Glu Trp Met
        35                  40                  45

Gly Arg Ile Phe Pro Gly Asp Gly Asp Thr Asp Tyr Asn Gly Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asn Val Phe Asp Gly Tyr Trp Leu Val Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
```

```
                130               135               140
Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
                180                 185                 190

Ser Ser Leu Gly Thr Gln Thr Tyr Ile Cys Asn Val Asn His Lys Pro
                195                 200                 205

Ser Asn Thr Lys Val Asp Lys Lys Val Glu Pro Lys Ser Cys Asp Lys
210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
                260                 265                 270

Pro Glu Val Lys Phe Asn Trp Tyr Val Asp Gly Val Glu Val His Asn
                275                 280                 285

Ala Lys Thr Lys Pro Arg Glu Glu Gln Tyr Asn Ser Thr Tyr Arg Val
                290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
                340                 345                 350

Leu Pro Pro Ser Arg Asp Glu Leu Thr Lys Asn Gln Val Ser Leu Thr
                355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
                420                 425                 430

Ala Leu His Asn His Tyr Thr Gln Lys Ser Leu Ser Leu Ser Pro Gly
                435                 440                 445

Lys

<210> SEQ ID NO 4
<211> LENGTH: 219
<212> TYPE: PRT
<213> ORGANISM: Artificial sequence
<220> FEATURE:
<223> OTHER INFORMATION: Light chain amino acid sequence of the anti-
      CD20 monoclonal antibody obinutuzumab.

<400> SEQUENCE: 4

Asp Ile Val Met Thr Gln Thr Pro Leu Ser Leu Pro Val Thr Pro Gly
1               5                   10                  15

Glu Pro Ala Ser Ile Ser Cys Arg Ser Ser Lys Ser Leu Leu His Ser
                20                  25                  30

Asn Gly Ile Thr Tyr Leu Tyr Trp Tyr Leu Gln Lys Pro Gly Gln Ser
```

```
                35                  40                  45
Pro Gln Leu Leu Ile Tyr Gln Met Ser Asn Leu Val Ser Gly Val Pro
 50                  55                  60

Asp Arg Phe Ser Gly Ser Gly Ser Gly Thr Asp Phe Thr Leu Lys Ile
65                   70                  75                  80

Ser Arg Val Glu Ala Glu Asp Val Gly Val Tyr Tyr Cys Ala Gln Asn
                 85                  90                  95

Leu Glu Leu Pro Tyr Thr Phe Gly Gly Gly Thr Lys Val Glu Ile Lys
                100                 105                 110

Arg Thr Val Ala Ala Pro Ser Val Phe Ile Phe Pro Pro Ser Asp Glu
            115                 120                 125

Gln Leu Lys Ser Gly Thr Ala Ser Val Val Cys Leu Leu Asn Asn Phe
        130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
210                 215

<210> SEQ ID NO 5
<211> LENGTH: 122
<212> TYPE: PRT
<213> ORGANISM: Artificial sequence
<220> FEATURE:
<223> OTHER INFORMATION: Variable heavy chain amino acid sequence of
      the anti-CD20 monoclonal antibody ofatumumab.

<400> SEQUENCE: 5

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asn Asp Tyr
            20                  25                  30

Ala Met His Trp Val Arg Gln Ala Pro Gly Lys Gly Leu Glu Trp Val
        35                  40                  45

Ser Thr Ile Ser Trp Asn Ser Gly Ser Ile Gly Tyr Ala Asp Ser Val
    50                  55                  60

Lys Gly Arg Phe Thr Ile Ser Arg Asp Asn Ala Lys Lys Ser Leu Tyr
65                  70                  75                  80

Leu Gln Met Asn Ser Leu Arg Ala Glu Asp Thr Ala Leu Tyr Tyr Cys
                85                  90                  95

Ala Lys Asp Ile Gln Tyr Gly Asn Tyr Tyr Tyr Gly Met Asp Val Trp
            100                 105                 110

Gly Gln Gly Thr Thr Val Thr Val Ser Ser
        115                 120

<210> SEQ ID NO 6
<211> LENGTH: 107
<212> TYPE: PRT
<213> ORGANISM: Artificial sequence
<220> FEATURE:
<223> OTHER INFORMATION: Variable light chain amino acid sequence of
      the anti-CD20 monoclonal antibody ofatumumab.
```

<400> SEQUENCE: 6

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
                20                  25                  30

Leu Ala Trp Tyr Gln Gln Lys Pro Gly Gln Ala Pro Arg Leu Leu Ile
            35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Ile
                85                  90                  95

Thr Phe Gly Gln Gly Thr Arg Leu Glu Ile Lys
                100                 105
```

<210> SEQ ID NO 7
<211> LENGTH: 222
<212> TYPE: PRT
<213> ORGANISM: Artificial Sequence
<220> FEATURE:
<223> OTHER INFORMATION: Fab fragment of heavy chain amino acid
      sequence of the anti-CD20 monoclonal antibody ofatumumab.

<400> SEQUENCE: 7

```
Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asn Asp Tyr
                20                  25                  30

Ala Met His Trp Val Arg Gln Ala Pro Gly Lys Gly Leu Glu Trp Val
            35                  40                  45

Ser Thr Ile Ser Trp Asn Ser Gly Ser Ile Gly Tyr Ala Asp Ser Val
    50                  55                  60

Lys Gly Arg Phe Thr Ile Ser Arg Asp Asn Ala Lys Lys Ser Leu Tyr
65                  70                  75                  80

Leu Gln Met Asn Ser Leu Arg Ala Glu Asp Thr Ala Leu Tyr Tyr Cys
                85                  90                  95

Ala Lys Asp Ile Gln Tyr Gly Asn Tyr Tyr Tyr Gly Met Asp Val Trp
                100                 105                 110

Gly Gln Gly Thr Thr Val Thr Val Ser Ser Ala Ser Thr Lys Gly Pro
            115                 120                 125

Ser Val Phe Pro Leu Ala Pro Gly Ser Ser Lys Ser Thr Ser Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Lys Val Glu Pro
    210                 215                 220
```

<210> SEQ ID NO 8
<211> LENGTH: 211

```
<212> TYPE: PRT
<213> ORGANISM: Artificial Sequence
<220> FEATURE:
<223> OTHER INFORMATION: Fab fragment of light chain amino acid
      sequence of the anti-CD20 monoclonal antibody ofatumumab.

<400> SEQUENCE: 8

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Ile
                85                  90                  95

Thr Phe Gly Gln Gly Thr Arg Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg
    210

<210> SEQ ID NO 9
<211> LENGTH: 451
<212> TYPE: PRT
<213> ORGANISM: Artificial Sequence
<220> FEATURE:
<223> OTHER INFORMATION: Heavy chain amino acid sequence of the anti-
      CD20 monoclonal antibody veltuzumab.

<400> SEQUENCE: 9

Gln Val Gln Leu Gln Gln Ser Gly Ala Glu Val Lys Lys Pro Gly Ser
1               5                   10                  15

Ser Val Lys Val Ser Cys Lys Ala Ser Gly Tyr Thr Phe Thr Ser Tyr
            20                  25                  30

Asn Met His Trp Val Lys Gln Ala Pro Gly Gln Gly Leu Glu Trp Ile
        35                  40                  45

Gly Ala Ile Tyr Pro Gly Met Gly Asp Thr Ser Tyr Asn Gln Lys Phe
    50                  55                  60

Lys Gly Lys Ala Thr Leu Thr Ala Asp Glu Ser Thr Asn Thr Ala Tyr
65                  70                  75                  80

Met Glu Leu Ser Ser Leu Arg Ser Glu Asp Thr Ala Phe Tyr Tyr Cys
                85                  90                  95
```

```
Ala Arg Ser Thr Tyr Tyr Gly Gly Asp Trp Tyr Phe Asp Val Trp Gly
            100                 105                 110

Gln Gly Thr Thr Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Arg Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450

<210> SEQ ID NO 10
<211> LENGTH: 213
<212> TYPE: PRT
<213> ORGANISM: Artificial Sequence
<220> FEATURE:
<223> OTHER INFORMATION: Light chain amino acid sequence of the anti-
      CD20 monoclonal antibody veltuzumab.

<400> SEQUENCE: 10
```

```
Asp Ile Gln Leu Thr Gln Ser Pro Ser Ser Leu Ser Ala Ser Val Gly
1               5                   10                  15

Asp Arg Val Thr Met Thr Cys Arg Ala Ser Ser Val Ser Tyr Ile
            20                  25                  30

His Trp Phe Gln Gln Lys Pro Gly Lys Ala Pro Lys Pro Trp Ile Tyr
            35                  40                  45

Ala Thr Ser Asn Leu Ala Ser Gly Val Pro Val Arg Phe Ser Gly Ser
50                  55                  60

Gly Ser Gly Thr Asp Tyr Thr Phe Thr Ile Ser Ser Leu Gln Pro Glu
65                  70                  75                  80

Asp Ile Ala Thr Tyr Tyr Cys Gln Gln Trp Thr Ser Asn Pro Pro Thr
                85                  90                  95

Phe Gly Gly Gly Thr Lys Leu Glu Ile Lys Arg Thr Val Ala Ala Pro
            100                 105                 110

Ser Val Phe Ile Phe Pro Pro Ser Asp Glu Gln Leu Lys Ser Gly Thr
            115                 120                 125

Ala Ser Val Val Cys Leu Leu Asn Asn Phe Tyr Pro Arg Glu Ala Lys
            130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
            195                 200                 205

Asn Arg Gly Glu Cys
    210

<210> SEQ ID NO 11
<211> LENGTH: 447
<212> TYPE: PRT
<213> ORGANISM: Artificial Sequence
<220> FEATURE:
<223> OTHER INFORMATION: Heavy chain amino acid sequence of the anti-
      CD20 monoclonal antibody tositumomab.

<400> SEQUENCE: 11

Gln Ala Tyr Leu Gln Gln Ser Gly Ala Glu Leu Val Arg Pro Gly Ala
1               5                   10                  15

Ser Val Lys Met Ser Cys Lys Ala Ser Gly Tyr Thr Phe Thr Ser Tyr
            20                  25                  30

Asn Met His Trp Val Lys Gln Thr Pro Arg Gln Gly Leu Glu Trp Ile
            35                  40                  45

Gly Ala Ile Tyr Pro Gly Asn Gly Asp Thr Ser Tyr Asn Gln Lys Phe
50                  55                  60

Lys Gly Lys Ala Thr Leu Thr Val Asp Lys Ser Ser Thr Ala Tyr
65                  70                  75                  80

Met Gln Leu Ser Ser Leu Thr Ser Glu Asp Ser Ala Val Tyr Phe Cys
                85                  90                  95

Ala Arg Val Val Tyr Tyr Ser Asn Ser Tyr Trp Tyr Phe Asp Val Trp
            100                 105                 110

Gly Thr Gly Thr Thr Val Thr Val Ser Gly Pro Ser Val Phe Pro Leu
            115                 120                 125

Ala Pro Ser Ser Lys Ser Thr Ser Gly Gly Thr Ala Ala Leu Gly Cys
```

```
              130                 135                 140
Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
            195                 200                 205

Thr Lys Val Asp Lys Lys Ala Glu Pro Lys Ser Cys Asp Lys Thr His
            210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
                260                 265                 270

Val Lys Phe Asn Trp Tyr Val Asp Gly Val Glu Val His Asn Ala Lys
            275                 280                 285

Thr Lys Pro Arg Glu Glu Gln Tyr Asn Ser Thr Tyr Arg Val Val Ser
            290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
                340                 345                 350

Pro Ser Arg Asp Glu Leu Thr Lys Asn Gln Val Ser Leu Thr Cys Leu
            355                 360                 365

Val Lys Gly Phe Tyr Pro Ser Asp Ile Ala Val Glu Trp Glu Ser Asn
            370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
                420                 425                 430

His Asn His Tyr Thr Gln Lys Ser Leu Ser Leu Ser Pro Gly Lys
            435                 440                 445

<210> SEQ ID NO 12
<211> LENGTH: 210
<212> TYPE: PRT
<213> ORGANISM: Artificial Sequence
<220> FEATURE:
<223> OTHER INFORMATION: Light chain amino acid sequence of the anti-
      CD20 monoclonal antibody tositumomab.

<400> SEQUENCE: 12

Gln Ile Val Leu Ser Gln Ser Pro Ala Ile Leu Ser Ala Ser Pro Gly
1               5                   10                  15

Glu Lys Val Thr Met Thr Cys Arg Ala Ser Ser Ser Val Ser Tyr Met
            20                  25                  30

His Trp Tyr Gln Gln Lys Pro Gly Ser Ser Pro Lys Pro Trp Ile Tyr
            35                  40                  45
```

-continued

```
Ala Pro Ser Asn Leu Ala Ser Gly Val Pro Ala Arg Phe Ser Gly Ser
    50                  55                  60

Gly Ser Gly Thr Ser Tyr Ser Leu Thr Ile Ser Arg Val Glu Ala Glu
65                  70                  75                  80

Asp Ala Ala Thr Tyr Tyr Cys Gln Gln Trp Ser Phe Asn Pro Pro Thr
                85                  90                  95

Phe Gly Ala Gly Thr Lys Leu Glu Leu Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg
    210

<210> SEQ ID NO 13
<211> LENGTH: 443
<212> TYPE: PRT
<213> ORGANISM: Artificial Sequence
<220> FEATURE:
<223> OTHER INFORMATION: Heavy chain amino acid sequence of the anti-
      CD20 monoclonal antibody ibritumomab.

<400> SEQUENCE: 13

Gln Ala Tyr Leu Gln Gln Ser Gly Ala Glu Leu Val Arg Pro Gly Ala
1               5                   10                  15

Ser Val Lys Met Ser Cys Lys Ala Ser Gly Tyr Thr Phe Thr Ser Tyr
            20                  25                  30

Asn Met His Trp Val Lys Gln Thr Pro Arg Gln Gly Leu Glu Trp Ile
        35                  40                  45

Gly Ala Ile Tyr Pro Gly Asn Gly Asp Thr Ser Tyr Asn Gln Lys Phe
    50                  55                  60

Lys Gly Lys Ala Thr Leu Thr Val Asp Lys Ser Ser Ser Thr Ala Tyr
65                  70                  75                  80

Met Gln Leu Ser Ser Leu Thr Ser Glu Asp Ser Ala Val Tyr Phe Cys
                85                  90                  95

Ala Arg Val Val Tyr Tyr Ser Asn Ser Tyr Trp Tyr Phe Asp Val Trp
            100                 105                 110

Gly Thr Gly Thr Thr Val Thr Val Ser Ala Pro Ser Val Tyr Pro Leu
        115                 120                 125

Ala Pro Val Cys Gly Asp Thr Gly Ser Ser Val Thr Leu Gly Cys
130                 135                 140

Leu Val Lys Gly Tyr Phe Pro Glu Pro Val Thr Leu Thr Trp Asn Ser
145                 150                 155                 160

Gly Ser Leu Ser Ser Gly Val His Thr Phe Pro Ala Val Leu Gln Ser
                165                 170                 175

Asp Leu Tyr Thr Leu Ser Ser Ser Val Thr Val Thr Ser Ser Thr Trp
            180                 185                 190
```

```
Pro Ser Gln Ser Ile Thr Cys Asn Val Ala His Pro Ala Ser Ser Thr
            195                 200                 205

Lys Val Asp Lys Lys Ile Glu Pro Arg Gly Pro Thr Ile Lys Pro Cys
    210                 215                 220

Pro Pro Cys Lys Cys Pro Ala Pro Asn Leu Leu Gly Gly Pro Ser Val
225                 230                 235                 240

Phe Ile Phe Pro Pro Lys Ile Lys Asp Val Leu Met Ile Ser Leu Ser
                245                 250                 255

Pro Ile Val Thr Cys Val Val Val Asp Val Ser Glu Asp Asp Pro Asp
            260                 265                 270

Val Gln Ile Ser Trp Phe Val Asn Asn Val Glu Val His Thr Ala Gln
        275                 280                 285

Thr Gln Thr His Arg Glu Asp Tyr Asn Ser Thr Leu Arg Val Val Ser
    290                 295                 300

Ala Leu Pro Ile Gln His Gln Asp Trp Met Ser Gly Lys Glu Phe Lys
305                 310                 315                 320

Cys Lys Val Asn Asn Lys Asp Leu Pro Ala Pro Ile Glu Arg Thr Ile
                325                 330                 335

Ser Lys Pro Lys Gly Ser Val Arg Ala Pro Gln Val Tyr Val Leu Pro
            340                 345                 350

Pro Pro Glu Glu Glu Met Thr Lys Lys Gln Val Thr Leu Thr Cys Met
        355                 360                 365

Val Thr Asp Phe Met Pro Glu Asp Ile Tyr Val Glu Trp Thr Asn Asn
    370                 375                 380

Gly Lys Thr Glu Leu Asn Tyr Lys Asn Thr Glu Pro Val Leu Asp Ser
385                 390                 395                 400

Asp Gly Ser Tyr Phe Met Tyr Ser Lys Leu Arg Val Glu Lys Lys Asn
                405                 410                 415

Trp Val Glu Arg Asn Ser Tyr Ser Cys Ser Val Val His Glu Gly Leu
            420                 425                 430

His Asn His His Thr Thr Lys Ser Phe Ser Arg
        435                 440

<210> SEQ ID NO 14
<211> LENGTH: 209
<212> TYPE: PRT
<213> ORGANISM: Artificial Sequence
<220> FEATURE:
<223> OTHER INFORMATION: Light chain amino acid sequence of the anti-
      CD20 monoclonal antibody ibritumomab.

<400> SEQUENCE: 14

Gln Ile Val Leu Ser Gln Ser Pro Ala Ile Leu Ser Ala Ser Pro Gly
1               5                   10                  15

Glu Lys Val Thr Met Thr Cys Arg Ala Ser Ser Ser Val Ser Tyr Met
            20                  25                  30

His Trp Tyr Gln Gln Lys Pro Gly Ser Ser Pro Lys Pro Trp Ile Tyr
        35                  40                  45

Ala Pro Ser Asn Leu Ala Ser Gly Val Pro Ala Arg Phe Ser Gly Ser
    50                  55                  60
```

```
Gly Ser Gly Thr Ser Tyr Ser Leu Thr Ile Ser Arg Val Glu Ala Glu
 65              70                  75                  80

Asp Ala Ala Thr Tyr Tyr Cys Gln Gln Trp Ser Phe Asn Pro Pro Thr
             85                  90                  95

Phe Gly Ala Gly Thr Lys Leu Glu Leu Lys Arg Ala Asp Ala Ala Pro
            100                 105                 110

Thr Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
        130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn
```